United States Patent [19]

Floyd, Jr. et al.

[11] 4,107,441
[45] Aug. 15, 1978

[54] NOVEL 16 HYDROXY 15-DEOXY-5-CIS-PROSTENOIC ACIDS AND ESTERS

[75] Inventors: Middleton Brawner Floyd, Jr., Suffern, N.Y.; Martin Joseph Weiss, Oradell, N.J.; William James McGahren, Demarest, N.J.; Robert Eugene Schaub, Upper Saddle River, N.J.

[73] Assignee: American Cyanamid Company, Stamford, Conn.

[21] Appl. No.: 607,867

[22] Filed: Aug. 26, 1975

Related U.S. Application Data

[63] Continuation-in-part of Ser. No. 370,256, Jun. 15, 1973, abandoned.

[51] Int. Cl.$^2$ ........................................... C07C 177/00
[52] U.S. Cl. ..................... 560/121; 260/345.7 P; 260/345.8 P; 260/395; 260/408; 260/410.9 R; 260/413; 260/448.8 R; 260/514 D; 424/305; 424/317; 542/426; 560/32; 560/62; 560/84; 560/85; 568/873
[58] Field of Search ....... 260/408 D, 514 D, 514 CY, 260/410.9 R, 413, 395

[56] References Cited

U.S. PATENT DOCUMENTS 3,965,143  6/1976  Collins et al. ...................... 260/408

Primary Examiner—Robert Gerstl
Attorney, Agent, or Firm—Denis A. Polyn

[57] ABSTRACT

This disclosure describes certain hydroxy substituted 15-deoxy-5-cis-prostenoic acids and esters useful as hypotensive agents, anti-ulcer agents, bronchodilators, anti-microbial agents, anticonvulsants, or as intermediates.

62 Claims, No Drawings

NOVEL 16 HYDROXY 15-DEOXY-5-CIS-PROSTENOIC ACIDS AND ESTERS

CROSS REFERENCE TO RELATED APPLICATION

This application is a continuation-in-part of our co-pending application Ser. No. 370,256, filed June 15, 1973 now abandoned.

BRIEF SUMMARY OF THE INVENTION

This invention relates to novel hydroxy substituted 15-deoxy-5-cis-prostenoic acids and esters as well as to intermediates and processes for their preparation. The novel compounds of this invention embrace all the possible optical isomers, diastereomers and enantiomers, racemates, and racemic mixtures represented by the following general formula:

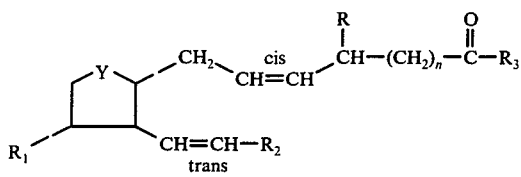

wherein n is an integer from 1 to 5, inclusive; R is selected from the group consisting of hydrogen and lower alkyl groups having up to three carbon atoms; $R_1$ is selected from the group consisting of hydrogen, hydroxy, tetrahydropyranyloxy, and tri(lower alkyl) silyloxy groups; $R_2$ is a moiety selected from the group consisting of those of the formulae:

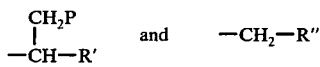

and

wherein P is an hydroxy or triphenylmethoxy group, R' is a straight chain alkyl or alkenyl group having from 3 to 10 carbon atoms, or a straight chain alkyl or alkenyl group having from 3 to 7 carbon atoms and having one or two branched alkyl groups each of from 1 to 3 carbon atoms, and R" is a straight chain alkyl or alkenyl group having from 3 to 10 carbon atoms optionally substituted with an hydroxy or triphenylmethoxy group, or a straight chain alkyl or alkenyl group having from 3 to 7 carbon atoms and having one or two branched alkyl groups of from 1 to 3 carbon atoms and optionally substituted with an hydroxy or triphenylmethoxy group, and a straight chain ω-haloalkyl group having from 2 to 7 carbon atoms; with the proviso that when R" is alkenyl then hydroxy or triphenylmethoxy substitution is restricted to saturated carbon atoms; $R_3$ is selected from the group consisting of hydroxy, alkoxy having from 1 to 12 carbon atoms, tetrahydropyranyloxy, and lower trialkylsilyloxy groups; Y is a divalent radical selected from the group consisting of those of the formulae:

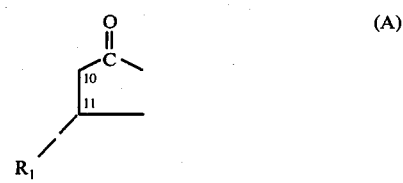

and the moiety of the formula:

may be the divalent radical of the formula:

with the proviso that when (A) is not (B) then at least one of $R_1$ and $R_2$ embraces an oxygen function.

Also embraced within the scope of the present invention are the non-toxic, pharmaceutically acceptable salts of the novel compounds of the present invention when $R_3$ is hydroxy. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine), procaine, and the like.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di, and triethylamolamine, ethyldiethanolamine, N-butylethanolamine, 2-amino-1-butanol, 2-amino-2-ethyl-1,3-propanediol, 2-amino-2methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds of this invention are administered in various ways for various purposes, e.g., intravenously, intramuscularly, subcutaneously, orally, intravaginally, rectally, buccally, sublingually, topically and in the form of sterile implants for prolonged action.

For intravenous injection or infusion, sterile aqueous isotonic solutions are preferred. For that purpose, it is preferred because of increased water solubility that $R_3$ by hydroxy or a salt with a pharmacologically accceptable cation. For subcutaneous or intramuscular injection, sterile solutions or suspensions of the acid, salt, or ester form in aqueous or non-aqueous media are used. Tablets, capsules, and liquid preparations such as syrups, elixers, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as α-cyclodextrin.

The novel compounds of the present invention are obtainable as oils having characteristic absorption spectra. They are relatively insoluble in water but are relatively soluble in common organic solvents such as ethanol, ethyl acetate, dimethylformamide, and the like. The cationic salts of the compounds when $R_3$ is hydrogen are, in general, white to yellow crystalline solids having characteristic melting points and absorption spectra. They are relatively soluble in water, methanol, and ethanol but are relatively insoluble in benzene, diethyl ether, and petroleum ether.

DETAILED DESCRIPTION OF THE INVENTION

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals. See Bergström et al., J. Biol. Chem. 238, 3555 (1963) and Horton, Experientia 21, 113 (1965) and references cited therein. All of the so-called natural prostaglandins are derivatives of prostanoic acid:

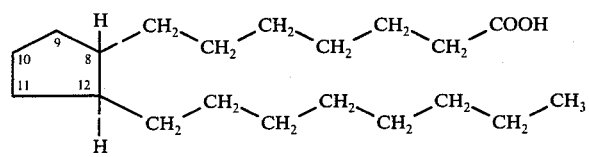

The hydrogen atoms attached to C-8 and C-12 are in trans configuration. The natural prostaglandins represent only one of the possible optical isomers. The compounds of this invention include all possible optical isomers and racemates.

The novel compounds of the present invention may be readily prepared from certain cyclopentenone intermediates which may be represented by the following general formula:

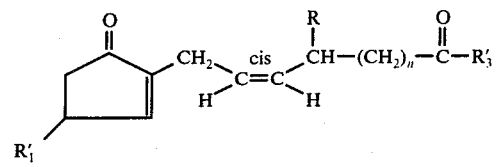

wherein R and n are as hereinabove defined; $R'_1$ has all the possibilities hereinabove defined for $R_1$ except hydroxy; and $R'_3$ embraces all the possibilities hereinabove defined for $R_3$ except hydroxy. The preparation of the 4-oxycyclopentenone intermediates is illustrated in Flowsheet A, which follows.

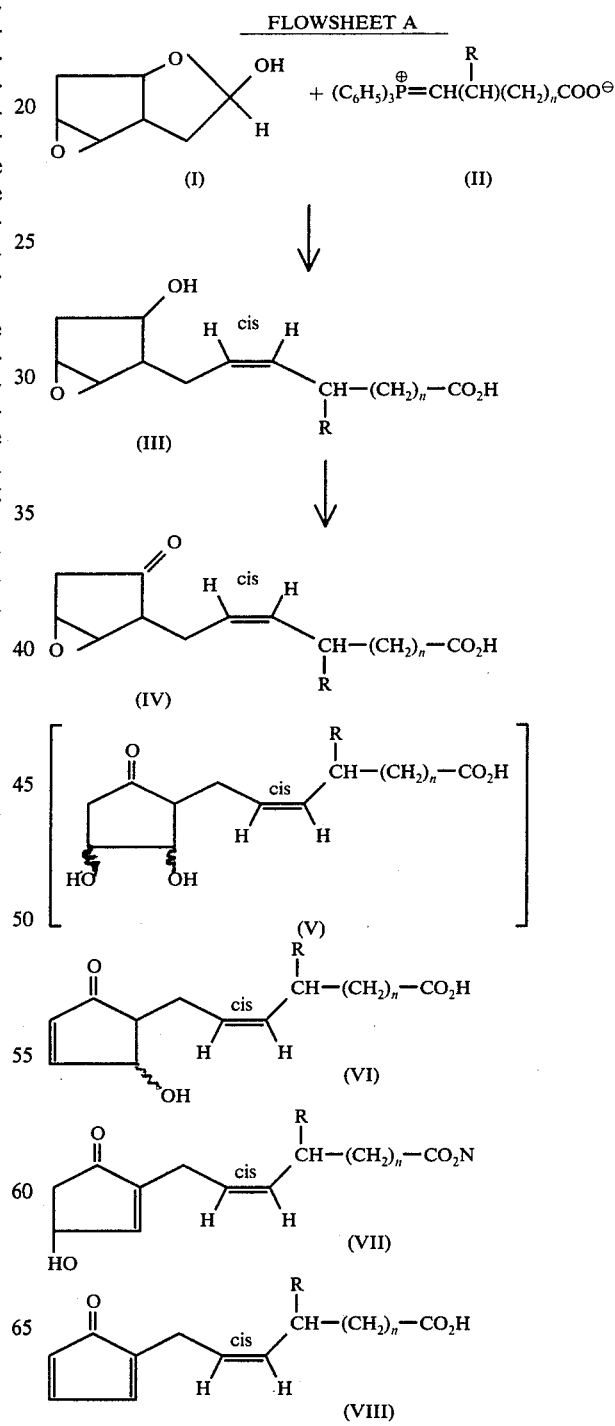

-continued
FLOWSHEET A

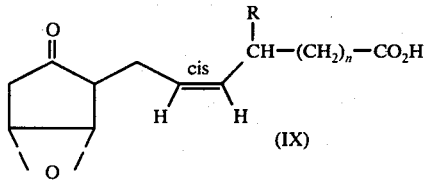

(IX)

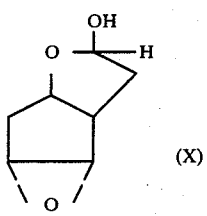

(X)

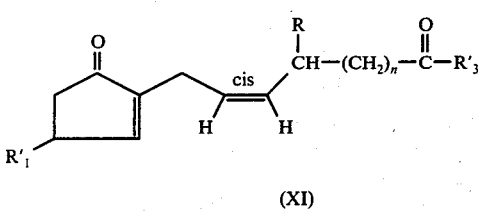

(XI)

FLOWSHEET B

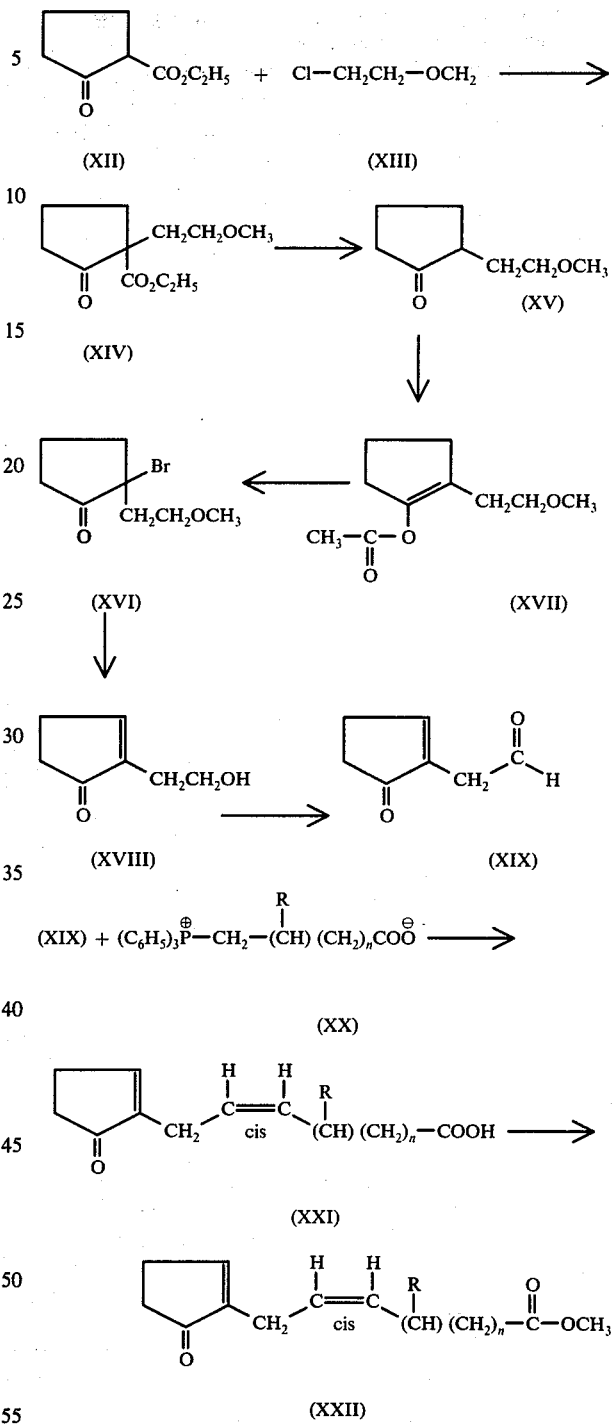

In accordance with the above reaction scheme the 3,4-epoxylactol (I) [E. J. Corey and R. Noyori, Tetrahedron Letters, 311 (1970)] is treated with the ylide (II) to give the 3,4-epoxycyclopentanol (III). Oxidation (for example with $H_2CrO_4 \cdot H_2SO_4$-ether or Jones reagent) of (III) provides the epoxy ketone (IV), mild base treatment of which results in the initial formation of the 4-hydroxycyclopent-2-en-1one (VII) and the isomeric 3-hydroxycyclopent-4-en-1-one (VI) as a mixture. Further treatment of this mixture with dilute base under mild conditions results in the isomerization of the 3-hydroxy isomer (VI) to the desired (VII). The transformation of the epoxy ketone (IV) to the hydroxycyclopentenones (VI) and (VII) and the isomerization of (VI) to (VII) may take place through the intermediacy of the 3,4-diol (V). It is also conceivable that isomerization of (VI) to (VII) procedes via the epoxy derivative (IV) or the corresponding α-epoxide (IX); it is further conceivable that (IV) procedes to (VI) and (VII) directly without the intermediacy of (V). Another possible intermediate for the isomerization of (VI) to (VII) is the corresponding diene (VIII). The preparation of (VII) is also possible via the α-epoxide series from (IX) prepared via the α-epoxide corresponding to (I) and (III) such as (X) or most conveniently via a mixture of the α and β epoxides. The hydroxy and acid function in the 4-hydroxycyclopentenones (VII) are then appropriately blocked to give (XI, $R'_1 \neq$ hydrogen). Appropriate blocking groups are tetrahydropyranyl, trimethylsilyl, dimethyl-isopropylsilyl, dimethyl-t-butylsilyl, and the like.

The preparation of the requisite 4-unsubstituted cyclopentenone intermediates can be accomplished by the sequences illustrated below in Flowsheets B and C, wherein R and n are as hereinabove defined.

In the above Flowsheet B, the sequence wherein 2-carbethoxycyclopentenone (XII) is transformed to 2-(β-hydroxyethyl)cyclopent-2-en-1-one (XVIII) is carried out in the manner described in Belgium Pat. No. 786,215 (granted and laid open to inspection on Jan. 15, 1973). Methyl ether cleavage of the corresponding 2-(β-methoxymethyl)cyclopentenone is achieved by treating with boron tribromide. Oxidation of the alcohol (XVIII) with Collins reagent, (chromium trioxide-pyridine complex in methylene chloride) under anhydrous conditions [J. C. Collins, W. W. Hess, and F. J. Frank, Tetrahedron Letters, 3363 (1968)], provides the aldehyde (XIX), which is then treated in anhydrous dimethylsulfoxide with the ylid prepared from an (ω-carboxyalkyl)triphenyl phosphonium betaine (XX) and sodium hydride in dimethylsulfoxide(dimsyl sodium). The use of dimethylsulfoxide as a solvent for this reaction leads to the predominant formation of the desired cis double bond derivative (XXI). The acid function in (XXI) can be esterified in the usual fashion; with diazomethane, the methyl ester (XXII) is obtained.

An alternative procedure is illustrated below in Flowsheet C, wherein R and n are hereinabove defined.

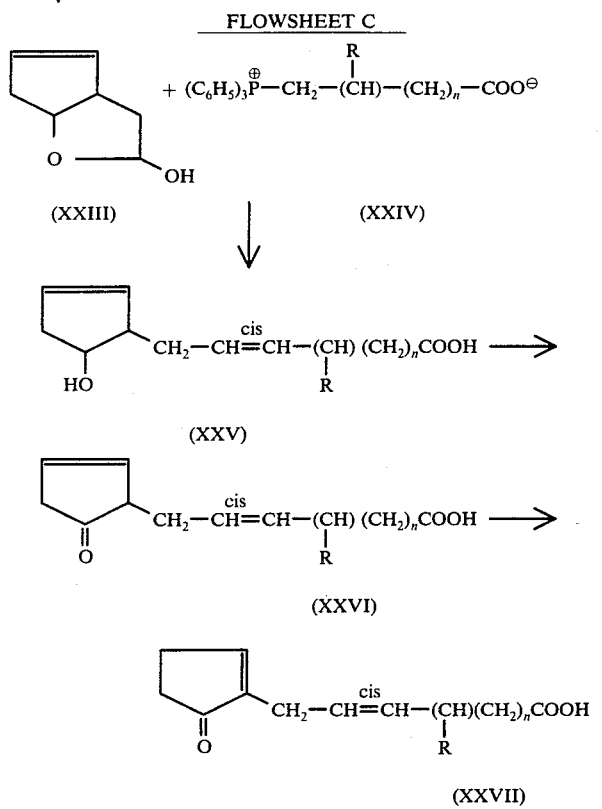

In Flowsheet C above, the bicyclic hemiacetal (XXIII) [P.A. Grieco, Journ. Org. Chem., 37, 2363 (1972)] is treated in dimethylsulfoxide with the ylid prepared from the triphenylphosphonium betaine (XXIV) and sodium hydride in dimethylsulfoxide (dimsyl sodium) to give the 1-hydroxy-3-cyclopentene (XXV). Oxidation with Jones reagent gives the corresponding ketone (XXVI), which on base treatment furnishes the required cyclopentenone (XXVII), which can then be esterified in the usual manner; e.g. to (XXII).

The trans-1-alkenyl side-chain is introduced into the molecule by a novel 1,4-conjugate addition procedure involving treatment of the ether-ester blocked 4-oxycyclopentenone (XI) of Flowsheet A or the 4-unsubstituted cyclopentenone ester (XXII) of Flowsheet B with a lithio alanate reagent, such as (XXXI) or (XXXIV), prepared as illustrated below in Flow-sheet D. In this Flowsheet R, R'$_1$, R'$_3$ and n are as hereinabove described; R"$_1$ is hydrogen or hydroxy, R$_5$ is a lower alkyl group (in (R$_5$)$_3$Al each value of R$_5$ is not necessarily the same); R'$_2$ is a moiety selected from the group consisting of

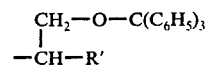

and

—CH$_2$-R''', wherein
R' is as hereinabove defined, and R''' is a straight chain alkyl or alkenyl group having from 3 to 10 carbon atoms optionally substituted with a triphenylmethoxy group, or a straight chain alkyl or alkenyl group having from 3 to 7 carbon atoms and having one or two branched alkyl groups each of from 1 to 3 carbon atoms, and optionally substituted with a triphenylmethoxy group, or other appropriately blocked hydroxy group, such as tri-lower alkylsilyloxy, and with the proviso that when R''' is alkenyl the oxy function is substituted on a saturated carbon atom, or a straight chain ω-halo alkyl group having from 2 to 7 carbon atoms; R"$_3$ is hydroxy or an alkoxy group having from 1 to 12 carbon atoms; and R"$_2$ embraces all the values defined hereinabove for R$_2$ except that it does not include triphenylmethoxy.

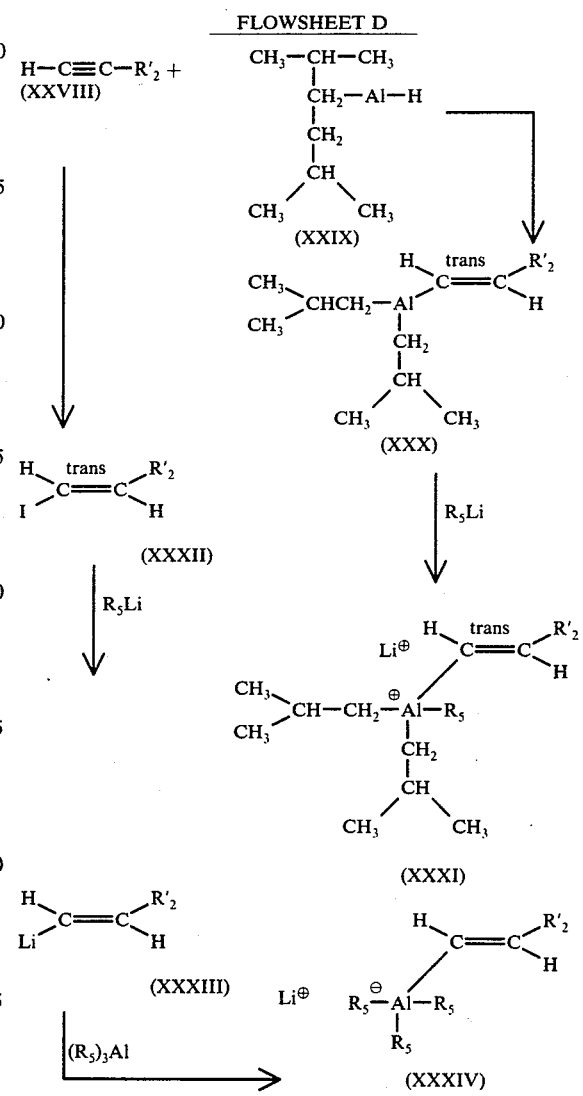

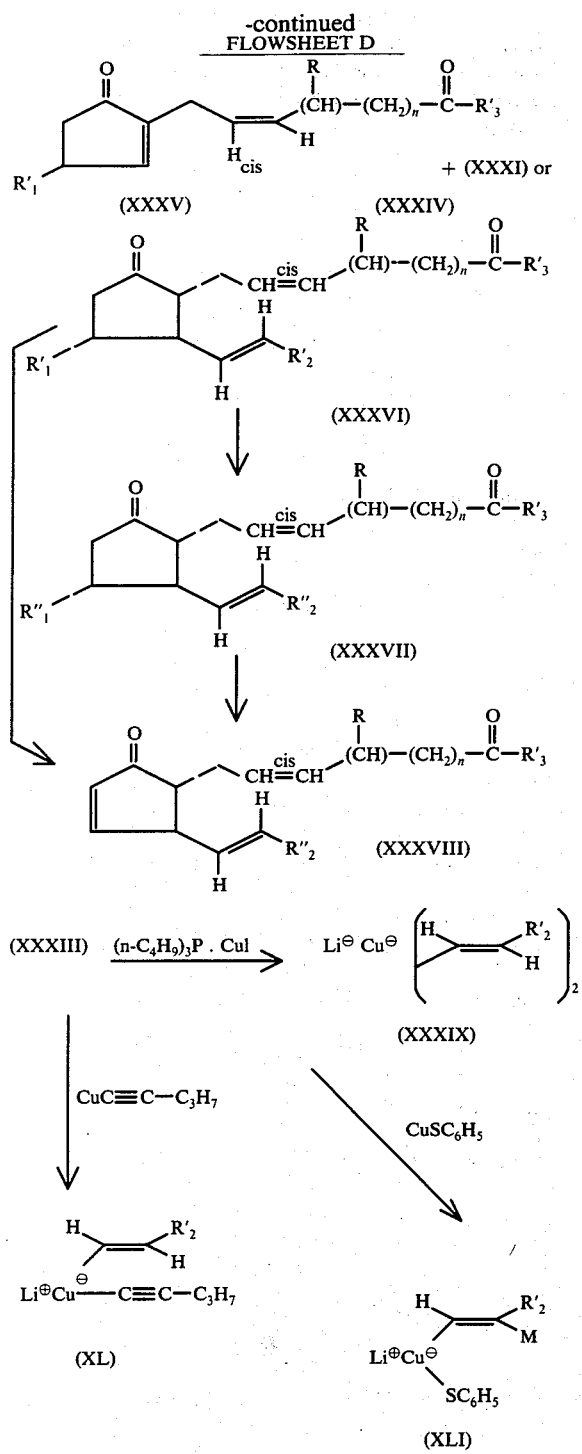

ous conditions, usually treating at about 70°–75° C. for about eighteen hours. The subsequent reaction with methyl or n-butyl lithium ($R_5$-Li) to give lithio alanate (XXXI) is preferably carried out in a mixture of the above solvents with an ether-type solvent such as diethyl ether, dibutyl ether, tetrahydrofuran, and the like. This reaction is rapid and is preferably carried out at 0° – 10° C. with cooling.

In an alternative procedure the acetylene (XXVIII) is treated without isolation of intermediates, with one equivalent of disiamylborane (prepared in situ from diborane and 2-methyl-2-butene) and then with excess anhydrous trimethylamine oxide followed by treatment with an aqueous solution of excess sodium hydroxide and a tetrahydrofuran solution of excess iodine to give the trans-1-alkenyl-1-iodide (XXXII). Treatment of (XXXII) at low temperatures, preferably at about −30° to −78° C., in an inert solvent, e.g., hexane, ether, or toluene, with an alkyl lithium ($R_5$-Li), e.g., n-butyl lithium or t-butyl lithium provides the trans-1-alkenyl lithium reagent (XXXIII). Treatment of this lithio derivative with a tri-alkyl aluminum, preferably trimethyl aluminum, furnishes the lithio trans-alkenyl trialkyl alanate (XXXIV).

The conjugate 1,4-addition of the lithio alanate, (XXXIV) or (XXXI), to the blocked cyclopent-2-en-1-one (XXXV) is preferably carried out at ambient temperatures for a period of 12 to 24 hours. This reaction is best carried out in an anhydrous ether-type solvent such as diethyl ether and the like; or in a solvent system such as benzene-hexane-diethyl ether. The intermediate alanate-enolate adduct is then carefully hydrolyzed in situ with dilute hydrochloric acid with cooling, and the products (XXXVI) are isolated in the usual manner well known in the art. Removal of tetrahydropyranyl or trialkylsilyl blocking groups and, if present, of the triphenylmethyl blocking group can then be accomplished by treating with weak acid. A preferred procedure involves heating at 45° C. for 3.5 hours in a solvent system consisting of acetic acid:tetrahydrofuran:water in the proportion of 4:2:1. If (XXXVI) is a tetrahydropyranyl or trialkylsilyl ester, there is then obtained the prostenoic acid (XXXVII, $R'_3$ = hydroxy). Alkyl esters are not usually hydrolyzed by this procedure. In the 11-oxy-9-oxo series saponification cannot be accomplished chemically, but can be achieved by enymatic means, for instance with Baker's yeast in the usual manner. In the 11-deoxy series ($R'_1$ = hydrogen) or in the 9-hydroxy series chemical saponifiis readily achieved.

Deblocking of the bis-tetrahydropyranyl blocked product ($R'_1$ = $R'_3$ = tetrahydropyranyloxy) under milder conditions then those cited above, for example with a 6:5:2 mixture of acetic acid-tetrahydrofuran-water at room temperature for two hours, selectively hydrolizes the tetrahydropyranyl ester but not the tetrahydropyranyl ether or triphenylmethoxy ethers, if present, to give (XXXV) wherein $R'_3$ is hydroxy and $R'_1$ is tetrahydropyranyloxy. These partially deblocked intermediates are useful for effecting transformations of the free acid function. The conditions cited hereinabove for selective hydrolysis also serves to selectively hydrolyze the trimethylsilyl ether and trimethylsilyl ester functions, if present.

An alternative conjugate 1,4-addition procedure for the preparation of the products of this invention involves the use of trans-1-alkenyl lithio cuprate which In accordance with the reaction scheme of Flowsheet D, the requisite lithio alanate intermediates, e.g., (XXXI) or (XXXIV), are prepared from the 1-alkyne (XXVIII) by one of two procedures. In one procedure, the 1-alkyne (XXVIII) is treated with diisobutylaluminum hydride (XXIX). This reaction of the 1-alkyne (XXVIII) with diisobutylaluminum hydride (XXIX) provides the alane (XXX) containing the trans-double bond and is carried out in an inert solvent such as benzene, toluene, and the like at temperatures in the range of 40° – 60° C. for several hours. It can also be carried out in a solvent such as tetrahydrofuran, usually in an approximate 2:1 mixture with benzene or hexane; in which case the reaction requires somewhat more vigorcan be prepared from the corresponding vinyl lithium derivative (XXXIII).

For the preparation of the asymmetrical lithio cuprate (XL) or the like, a solution of one molar equivalent of copper (I)-1-alkyne, preferably copper (I)-1-pentyne is anhydrous hexamethylphosphorous triamide, preferably three to five molar equivalents, and anhydrous ether is added to one molar equivalent of the aforementioned vinyl lithium (XXXIII) solution cooled to about −78° C. After about one hour at this temperature, a molar equivalent of the requisite cyclopentenone (XXXV) is added. After several hours at −15° C. to 0° C., the reaction mixture is quenched with aqueous ammonium chloride solution and the blocked product (XXXV) is isolated in the usual manner. The deblocking of this product to give (XXXVII) is then carried out in the manner as described hereinabove.

It is also possible to effect conjugate 1,4-addition with the asymmetrical lithio cuprate (XLI) derived from vinyl lithium (XXXIII) and cuprous thiophenoxide. A solution of vinyl lithium (XXXIII) is ether at 31 78° C. is reacted with an equimolar amount of a reagent prepared by admixture, in ether at a temperature of 0° to 78° C., of equimolar amounts of cuprous thiophenoxide and copper (I) iodide tributylphosphonium complex. After about 30 minutes at this temperature, the lithio cuprate (XLI) is treated with the requisite cyclopentenone (XXXV) as described hereinabove for the conjugate addition with 1alkynyl lithio cuprate (XL).

For the preparation of the symmetrical lithio cuprate (XXXIX) one molar equivalent of copper (I) iodide tributylphosphine complex, dissolved in anhydrous ether, is added at about −78° C. to two molar equivalents of the aforementioned vinyl iodide (XXXIII) solution in hexanes, cooled to −78° C. After about one hour at this temperature, the lithio cuprate (XXXIX) is treated with the requisite cyclopentenone (XXXV) as described hereinabove for the conjugate addition with the 1-alkynl lithio cuprate (XL).

The procedures for conjugate addition involving organocopper reagents are well known in the art, see for example C. J. Sih, et al., J. Amer. Chem. Soc., 97, 865 (1975).

In the cases where $R'_1$ = trimethylsilyloxy in cyclopentenone (XXXV), the conjugate addition is performed at −78° to −40° C. The reaction is quenched by addition of an ether solution of acetic acid. Removal of blocking groups is then carried out as described hereinabove.

All available evidence leads us to believe that the —CH═CH—$R'_2$ function introduced by the alanate process (see XXXVI) occupies a position trans to the 11-oxy function. Similarly, we are lead to the conclusion that in the product (XXXVII) the two side-chains attached to $C_8$ and $C_{12}$ are trans to each other. However, we are not certain of this configurational relationship in product (XXXVI) as it is obtained directly from the alanate process. These products may have the side-chains in a trans- or cis-relationship or they may be a mixture containing both the trans- and cis-isomers. This is indicated in the nomenclature of the compounds involved by the designation 8 ξ. In order to ensure a trans-relationship in (XXXVI) these products can be submitted to conditions known in the literature to equilibrate the cis-8-iso-PGE$_1$ to a mixture containing about 90% of the trans product. These conditions involve treatment with potassium acetate in aqueous methanol for 96 hours at room temperature.

The triphenylmethoxy substituted lithio alanate reagent of type (XXXIV) and its precursors are novel and useful compounds which are also embraced by this invention. They may be defined by generic formulae A and B.

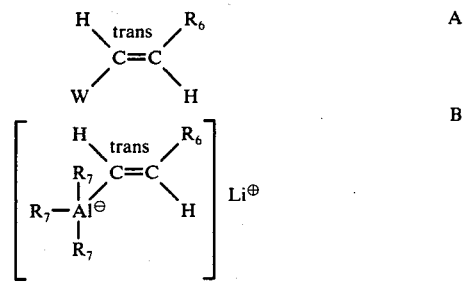

In A and B $R_6$ is selected from the moieties consisting of

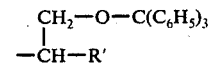

and

wherein R' is a straight chain alkyl or alkenyl group having from 3 to 10 carbon atoms, or a straight chain alkyl or alkenyl group having from 3 t0 7 carbon atoms and having one branched alkyl group of from 1 to 3 carbon atoms; and $R_8$ is a straight chain alkyl or alkenyl group having from 3 to 10 carbon atoms and substituted with one triphenylmethoxy group, or a straight chain alkyl or alkenyl group having from 3 to 7 carbon atoms and having one or two branched alkyl groups of from 1 to 3 carbon atoms and substituted with a triphenylmethoxy group, with the proviso that when $R_8$ is alkenyl the triphenylmethoxy group is substituted on a saturated carbon atom; $R_7$ is a straight chain lower alkyl group not necessarily the same for each use, and W is selected from the group consisting of iodine and lithium atoms.

Although the triphenylmethyl (or substituted triphenylmethyl), is essential for the ultimate introduction of a hydroxy substituted $R_2$ moiety via lithio alanates prepared by the sequence (XXVIII) + (XXIX)→ (XXX)→ (XXXI), other blocking groups, e.g., tetrahydropyranyl, tri-alkylsilyl, α-ethoxy-lower alkyl, t-butyl, etc., are also useful in the sequence: (XXVIII)→ (XXXII)→ (XXXIII)→ (XXXIV). For the introduction of a t-hydroxy group or a hydroxy group adjacent to two lower alkyl groups a trialkylsilyl, particularly trimethylsilyl, blocking groups is preferred.

When the 11-hydroxy derivatives (XXXVII, R″$_1$ Δ hydroxy) or the 11-oxy derivatives embraced by (XXXVI), are treated with dilute acid it is possible to effect elimination and the formation of the corresponding $\Delta^{10}$ derivative (XXXVIII), prostaglandins of the A type. A preferred procedure involves treatment in tetrahydrofuran-water (2:1) solvent 0.5N in hydrochloric acid for about seventy hours at ambient temperatures. Under these conditions a tetrahydropyranyl or trialkylsilyl ester will undergo hydrolysis. (See Flowsheet D, above).

The 11-oxy-9-keto derivatives, e.g., (XLI), of this invention can be converted to the corresponding 9- hydroxy derivatives. If this conversion is effected with sodium borohydride, the product is a mixture of 9α-and 9β-hydroxy derivatives (XLII) and (XLIII), respectively, as set forth in the following reaction scheme; wherein R, R″$_1$, R″$_2$, R″$_3$ and n are as hereinabove defined.

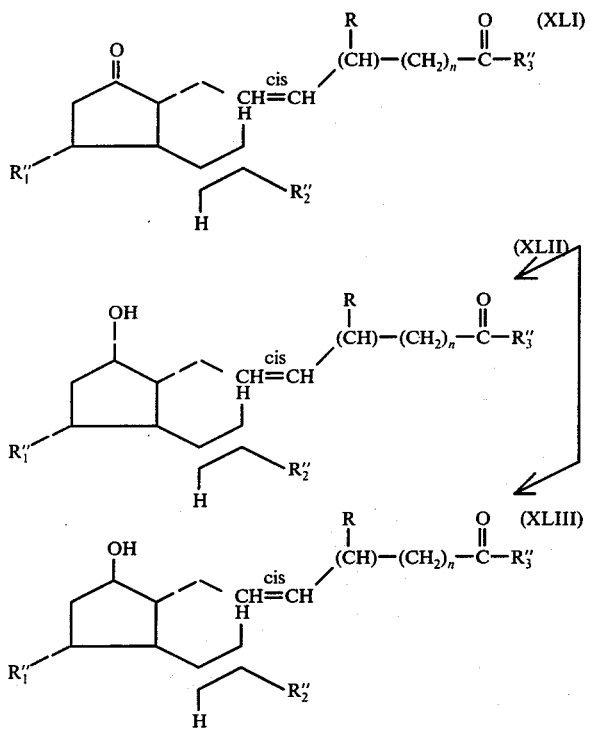

When the reaction is carried out with lithium perhydro-9b-boraphenylyl hydride [H. C. Brown and W. C. Dickason, Journ. Amer. Chem. Soc., 92, 709 (1970)] or lithium tris-(t-butyl)-borohydride [H. C. Brown and S. Krishnamurthy, ibid., 94, 7159 (1972)] the product is at least predominantly the 9α-hydroxy derivative (XLII), wherein the 9-hydroxy group is cis to the side-chain attached to C$_8$ and to the 11-oxy function, if present. In accordance with accepted convention, an α-substituent at the 8-, 9-, 11-or 12-positions is behind the plane of the paper whereas a β-substituent at these positions is in front of the plane of the paper. This is usually represented by a - - - bond for an α-substituent, a ⌇ bond for a β-substituent, and a   bond where both are indicated.

The carboxylic acids of this invention can be readily converted to the various alkyl esters of this invention by treatment in the usual manner with the appropriate diazoalkane. The preparation of diazoalkanes by various procedures are well-described in the art, see for example C. D. Gutsche, Organic Reactions, VIII, 389 (1954). Certain of the esters of this invention can also be obtained directly by use of the appropriate cyclopentenone ester (see XXXV). The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° to 15° C. with a molar equivalent of a tri-alkylamine, preferably triethylamine, tributylamine and the like, and then a molar equivalent of isobutyl chlorocarbonate or the like. The resulting mixed anhydrides is then treated with the appropriate alcohol to give the derivatized product. (For a pertinent literature analogy see Prostaglandins, 4, 738 (1973).)

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy see U.S. Pat. No. 3,821,279, June 28, 1974). A third procedure involves use of dicyclohexylcarbodiimide in the usual manner; for a pertinent literature analogy see German Offen. 2,365,205 (July 11, 1974); Chem. Abst., 81, 120098 g. (1974).

The esterified alcohol derivatives of this invention are also prepared in the usual manner by procedures well-known in the art from the appropriate alkanoic acid anhydride or acid chloride.

When the compounds of this invention are prepared from racemic starting compounds two racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19-27 (August, 1973) as well as references cited therein. Additional information concerning high speed liquid chromatography and the instruments necessary for its application is available from Waters Associate, Inc., Maple St., Milford, Mass.]

It is also possible to prepare the individual enantiomers via the conjugate addition procedure discussed above by starting with a resolved 4-oxycyclopentenone (see XXXV) and a resolved β-chain precursor (see XXVIII or XXXII).

In the following formulae Z has the value

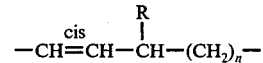

wherein R and n are as hereinabove defined.

The 4-hydroxycyclopentenone racemates may be resolved into their component enantiomers (L) and (LI) by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride (to give LII), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (L) and (LI). A useful procedure for the resolution of a 4-hydroxycyclopentenone racemate via an oxime such as (LII) is described in the art [R. Pappo, P. Collins and C. Jung, Tetrahedron Letters, 943 (1973)].

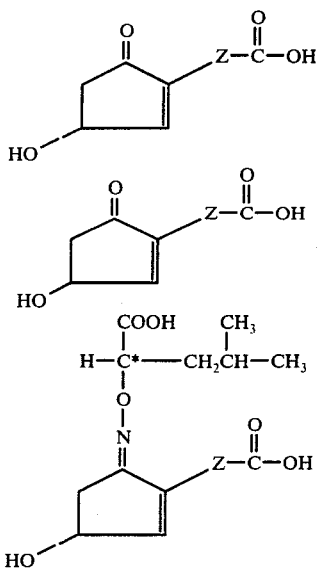

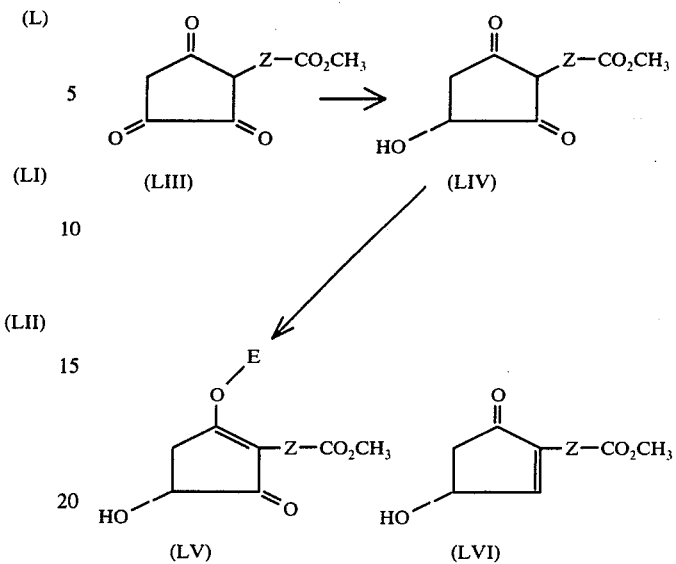

An alternative procedure for the preparation of the 4(R)-hydroxycyclopentenone enantiomers such as (L) involves as a key step the selective microbiological or chemical reduction of trione (LIII) to the 4(R)-hydroxycyclopentanedione (LIV). A wide variety of microorganisms are capable of accomplishing this asymmetric reduction, one of the most useful being *Dipodascus unincleatus*.

Conversion of hydroxycyclopentanedione (LIV) to an enol ether or enol ester, (LV, E = alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° to −15° C. Reduction of (LV) with excess sodium bis(2-methoxyethoxy)aluminum hydride in a solvent such as tetrahydrofuran or toluene at low temperatures, such as −60° to −78° C., followed by mild acid hydrolysis (representative conditions; aqueous dilute hydrochloric acid, pH 2.5; or oxalic acid, sodium oxalate in chloroform) at ambient temperatures from 1 to 3 hours provides the 4(R)-hydroxycyclopentenone ester (LVI). The ester (LVI), after blocking the hydroxy function as described hereinabove, can be subjected to conjugate addition reactions also as described hereinabove. The conjugate addition product, after deblocking the 11- and 15-hydroxy groups, will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih et al., Journ. Amer. Chem. Soc., 95 1676 (1973); J. B. Heather et al., Tetrahedron Letters, 2213 (1973); R. Pappo and P. W. Collins, Tetrahedron Letters, 2627 (1972); R. Pappo, P. Collins and C. Jung, Ann. N.Y. Acad. Sci., 180, 64 (1971); C. J. Sih, et al., Journ. Amer. Chem. Soc., 97, 865 (1975). For a descriptive of the baker's yeast procedure see C. J. Sig et al., Journ. Amer. Chem. Soc., 94 3643 (1972).

Procedures for the preparation of the requisite cyclopentanetriones (LIII) are well-established in the art and generally involve the treatment of an ω-1 oxo long chain ester (LVII) with methy or ethyl oxalate and a base such as sodium methoxide in methanol, followed by treatment with dilute hydrochloric acid in aqueous methanol to effect the dealkoxalylation of the intermediate (LXVIII). See J. Kutsube and M. Matsui, Agr. Biol. Chem., 33, 1078 (1969); P. Collins, C. J. Jung and R. Pappo, Israel Journal of Chemistry, 6, 839 (1968); R. Pappo, P. Collins and C. Jung, Ann. N.Y. Acad. Sci., 180, 64(1971); C. J. Sih et al., Journ. Amer. Chem. Soc., 95, 1676 (1973) (see reference 7); and J. B. Heather et al., Tetrahedron Letters, 2313 (1973) for pertinent background literature.

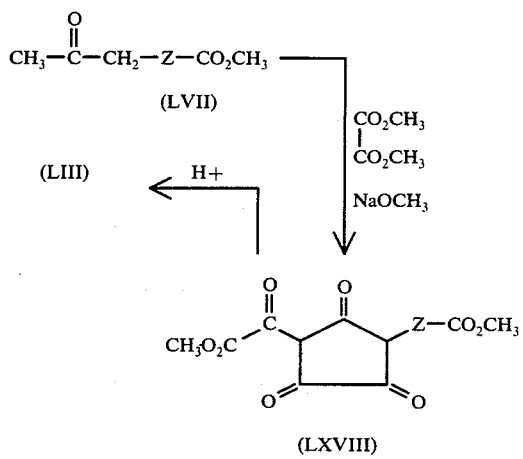

The intermediate keto esters (LVII) may be prepared by a variety of methods known to the art. One useful procedure is outlined below and involves alkylation of ethyl acetoacetate sodium salt (LIX) in the usual manner with the appropriate side-chain precursor (LX, X=Cl, Br, I, preferably Br or I) followed by decarbethoxylation and reesterification, all in the usual manner.

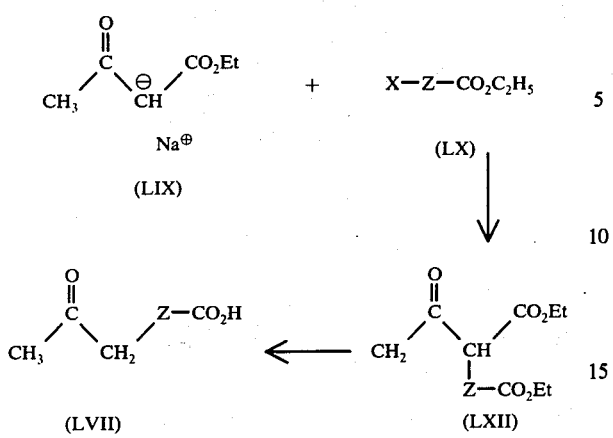

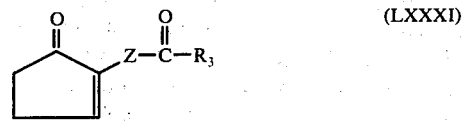

It is also possible to resolve the 4-hydroxycyclopentenone racemate (LXXVI) by microbiological means. Thus, treatment of the 4-O-alkanoyl or aroyl derivatives (LXXVII), $R_{12}$ = aryl or alkyl) of racemate (LXXVI) (preferably the 4-O-acetyl and 4-O-propionyl derivatives) with an appropriate microorganism preferably a Saccharomyces species, e.g. 1375-143, affords preferential de-O-acylation of the 4(R)-enantiomer to give (LXXVIII), which is then separated from the unreacted 4-(S)-O-acyl enantiomer (LXXIX) by chromatographic procedures. After separation, mild hydrolysis of the 4(S) derivative (LXXIX) provides the 4(S)-hydroxycyclopentenone (LXXX) [See N. J. Marscheck and M. Miyano, Biochimica et Biophysica Acta, 316, 363 (1973) for related examples.]

ported; for a literature example, see S. Kurozumi, T. Tora and S. Ishimoto, Tetrahedron Letters, 4959 (1973). Other organisms can also accomplish this hydroxylation.

An alternate resolution procedure involves derivatization of the alcohol function of the racemic hydroxycyclopentenone to give ester-acid derivatives such as (LXXXII) wherein $R''_3$ is hydrogen or an alkoxy group, $n'$ is zero or two and Z is as hereinabove defined.

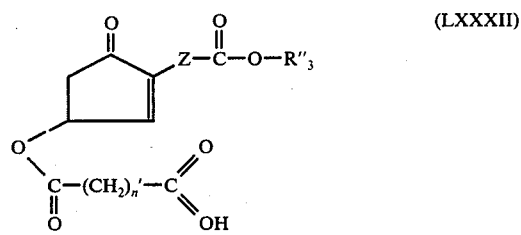

Such derivatives may be obtained from the corresponding free hydroxycyclopentenone by treatment in the usual manner with oxalyl chloride, succinyl chloride, succinic anhydride and the like. Treatment of the resulting acid or diacid ($R''_3$= hydrogen) with optically active amines e.g., 1-(−)-α-methylbenzylamine, d-(+)-α-methylbenzylamine, brucine, dehydroabietylamine,

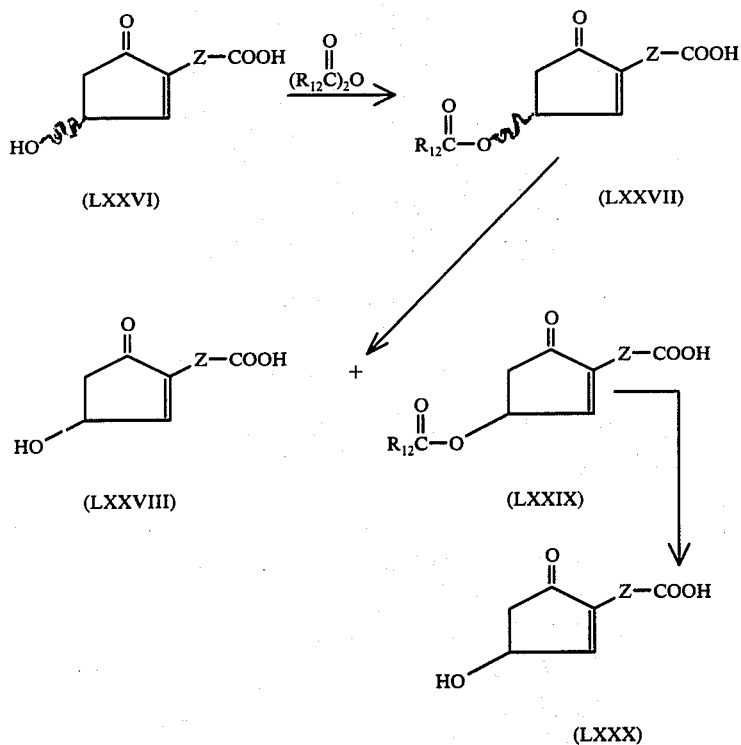

It is also possible to prepare the individual 4-hydroxycyclopentenones (LXXVIII) and (LXXX) directly by selective microbial hydroxylations of the corresponding 4-unsubstituted cyclopentenone (LXXXI). For example, with *Aspergillus niger* ATCC 9142; a selective 4(R)-hydroxylation of (LXXXI) [Z = $(CH_2)_6$] has been reported;

strychnine, quinine, cinchonine, quinidine, ephedrine, (+)-α-amino-1-butanol and the like, and fractional recrystallization of the resulting diastereomeric mixtures, followed by cleavage of the 4-oxy ester function in each of the individually isolated diastereomers provides the individual 4(S)- and 4(R)-hydroxycyclopentenone enantiomers (L) and (LI) or their respective esters. Cleavage of the oxalate acid ester (LXXXII, n = 0) can be accomplished by treatment with lead tetraacetate in pyridine solution. For an example of a similar use of oxalate acid-esters see J. G. Molotkovsky and L. D. Bergelson, Tetrahedron Letters, 4791 (No. 50, 1971); for an example of the use of succinate acid-ester see B. Goffinet, Ger. Offen. 2,263,880; Chem. Abstracts, 79, 78215$_2$ (1973).

The racemic β-chain precursors can be resolved at either the acetylenic alcohol stage (XXVIII, Flowsheet D) or the trans-vinyl iodide stage (XXXII), Flowsheet D) by a variety of methods well-known in the art. These methods will be illustrated below with the acetylenic alcohol (LXXXIII), but they apply equally well to the trans-vinyl iodide (LXXXIV). Furthermore, the resolved acetylenic alcohols corresponding to (LXXXIII) can be converted to the trans-vinyl iodides corresponding to (LXXXIV) or its derivatives as described hereinabove without racemization [see for an example, A. F. Kluge, K. G. Untch and J. H. Fried, Journ. Amer. Chem. Soc., 94, 7827 (1972)].

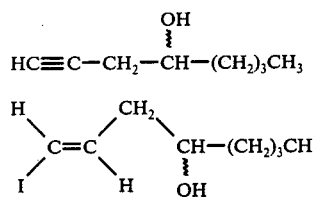

(LXXXIII)

(LXXXIV)

Racemates (LXXXIII) or (LXXXIV) can be resolved by reverse phase and absorption chromatography on an optically active support system or by selective transformation of one isomer by microbiological or enzymatic procedures.

A more generally applicable procedure involves conversion of the racemic alcohol to a mixture of diastereomers by derivatization of the hydroxy function with an optically active reagent, followed by separation of the diastereomers by fractional crystallization or chromatographic procedures, as discussed hereinabove. Regeneration of the alcohol function from the individual diastereomer then provides the individual enantiomeric alcohols, e.g., (LXXXV) and (LXXXVI).

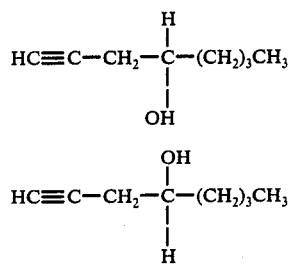

(LXXXV)

(LXXXVI)

Useful derivatives for resolution purposes include the salts of the phthalate half acid ester (LXXXVII) with an optically active amine (e.g., 1-(−)-α-methylbenzylamine, d-(+)-α-methylbenzylamine, brucine, dehydroabietylamine, strychnine, quinine, cinchonine, cinchonidine, quinidine, ephedrine, deoxyephedrine, amphetamine, (+)-2-amino-1-butanol, (−)-2-amino-1-butanol and the like).

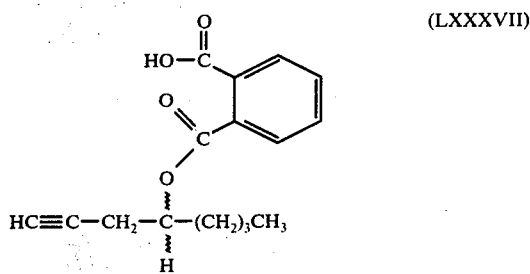

(LXXXVII)

For the resolution in the art of the related 3-hydroxy-1-octyne by this procedure see J. Fried et al., Annals of the N.Y. Acad. of Sci., 180, 38 (1971), and of the related 1-iodotrans-1-octen-3-ol see A. F. Kluge, K. G. Untch and J. H. Fried, Journ. Amer. Chem. Soc., 94, 7827 (1972).

Other useful derivatives are the diastereomeric carbamates (LXXXVIII) obtained by treatment of racemate (LXXXIII) with an optically active isocyanate (e.g., (+)-1-phenylethylisocyanate and (−)-1-phenylethylisocyanate).

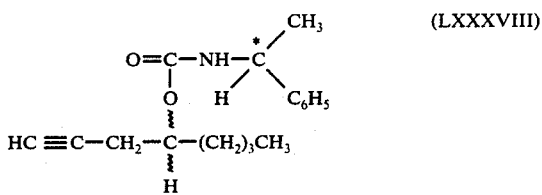

(LXXXVIII)

Various esters of racemate (LXXXIII) with optically active acids are also useful for resolution purposes. Among the optically active acids which can be used in this connection are ω-camphoric acid, menthoxyacetic acid, 3α-acetoxy-Δ$^5$-etianic acid, 3α-acetoxy-5,16-etiadienoic acid, (−)-α-methoxy-α-trifluoromethylphenylacetic acid (see LXXXIX), (+)-α-methoxy-α-trifluoromethylphenylacetic acid, and the like.

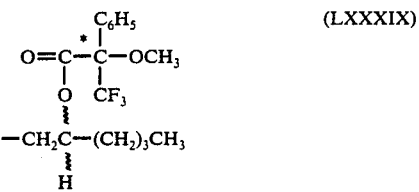

(LXXXIX)

The resolution of the related 1-octyne-3-ol with 3β-acetoxy-Δ$^5$-etianic acid and 3β-acetoxy-5,16-etiadienoic acid has been described in the art [see R. Pappo, P. Collins, and C. Jung, Annals of the N.Y. Acad. of Sci., 180, 64 (1971)].

The preparation of the enantiomeric acetylenic alcohols or 4-hydroxy-trans-vinyl iodides can also be accomplished by microbial techniques, involving a selective de-esterification of 4-O-alkanoyl or aroyl derivatives (XC) followed by chromatographic separation to the individual enantiomers and hydrolysis of the non de-esterified ester. Useful microorganisms for this purpose are Rhizopus arrhizus and Rhizopus nigricans (ATCC 6227b).

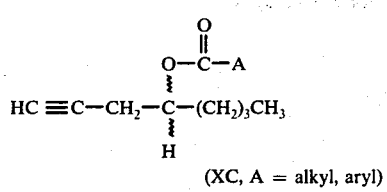

(XC, A = alkyl, aryl)

Alternatively, it is possible to effect selective microbial reduction of the corresponding 4-keto derivatives (XCI) and (XCII) to a single enantiomer; useful microorganisms for this purpose are *Penicillium decumbens* and *Aspergillus ustus*. Ketones (XCI) and (XCII) are readily obtainable by oxidation under mild conditions of the corresponding alcohols. For pertinent literature examples see J. B. Heather et al., Tetrahedron Letters, 2313 (1973). It is also possible to effect optically selective reduction of ketones

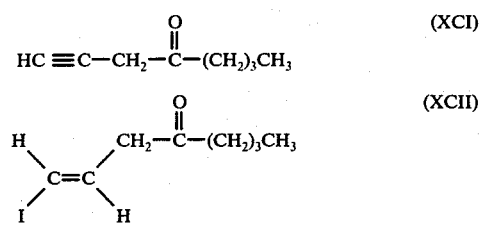

(XCI) or (XCII) by the use of an optically active reducing agent such as tri(+S-2-methylbutyl)aluminum etherate, lithium aluminum hydride-3-O-benzyl-1,2-O-cyclohexyldiene-α-D-glucofuranose complex, and lithium hydrodipinan-3α-ylborate. For pertinent references to this procedure see R. A. Kretchmer, Journ. Org. Chem. 37, 801 (1972); S. A. Landor et al., Journ. Chem. Soc. (C) 1822, 2280 (1966), ibid. 197 (1967); M. F. Grundon et al., ibid., 2557 (1971); and J. D. Morrison and H. S. Mosher, "Assymetric Organic Reactions," pp. 160-218, Prentice-Hall, Englewood Cliffs, N.J. (1971).

It is to be noted that use of only one resolved precursor, ether the β-chain or the 4-hydroxycyclopentenone, in the conjugate addition process will lead to the formation of two diastereomers, which, at least in appropriate instances, can then be separated by chromatographic and other procedures (as described above for the corresponding racemate) into the individual components.

For the particular case involving the preparation of optically active acetylenic alcohols wherein the hydroxy group occupies the 4-position of the chain, advantage may be taken of a well-known and general microbiological reduction process, depicted in Flowsheet E. According to this process, a 1-hydroxy-2-oxalkene (XCV) is added to the fermenting mixture obtained from sucrose and baker's yeast (see P. A. Levene and A. Walti, Org. Synthesis, Coll. Vol. II, p. 545 and J. P. Anette and N. Spassky, Bull. Soc. Chim. France, 1972, 4217, for appropriate examples). The reductase of this system stereospecifically provides the (R)-1,3-dihydroxyalkanes (XCVII). The glycol thus prepared is converted stereospecifically to the (R)-1,2-epoxyalkane (XCVI) by one of several procedures known in the art (see B. T. Golding et al., Journ. Chim. Soc. Perkin I. 1973, 1214 and M. S. Newman and C. M. Chen, Journ. Amer. Chem. Soc., 95, 278 (1973) for appropriate examples). The stereospecific conversion of this epoxide to the (R)-4-hydroxy-1-alkyne (XCVIII) may be accomplished by displacement with lithium acetylide-ethylenediamine complex in dimethyl sulfoxide (see E. Casadevall, et al., Compt. Rind. C, 265, 839 for pertinent literature).

The (R)-1,2-dihydroxyalkane (XCVII) obtained from the yeast fermentation may also be used for the preparation of the (S)-4-hydroxy-1-alkyne (CII). Preferential triphenylmethylation of the primary alcohol group provides the monoether (IC) (see L. J. Stegerhoek and P. E. Verkade, Rec. Trav. Chim. 74, 143 (1955) for pertinent literature). The remaining alcohol group is esterified with a sulfonyl halide such as p-toluenesulfonyl chloride to provide the sulfonate ester (CI). Catalytic hydrogenolysis of the trityl group followed by treatment of the resulting free primary alcohol with a strong base, e.g. potassium hydroxide in methyl alcohol, provides the epoxide of the opposite configuration, a (S)-1,2-epoxyalkane (CIII) (see J. Fried, et al. Journ. Amer. Chem. Soc., 94, 4343 (1972) and J. W. Cornforth et al. Journ. Chem. Soc., 1959, 112, for pertinent literature). This substance is reacted with lithium acetylide-ethylenediamine complex to provide the (S)-4-hydroxy-1-alkyne (CII).

Alternatively the (R)-4-hydroxy-1-alkyne (XCVIII) may be converted to a sulfonate ester (C), and the sulfonate function of the latter may be displaced by hydroxy to provide the (S)-4-hydroxy-1-alkyne (CII) see R. Baker, et al., Journ. Chem. Soc. C. 1969, 1605 for pertinent literature).

The (R)- or (S)-4-hydroxy-1-alkynes are converted via either the vinyl iodide (XCIII) or the alane (XCIV) to 16-hydroxyprostaglandins of the (16R)- and (16S)-series respectively by the procedure outlined hereinabove.

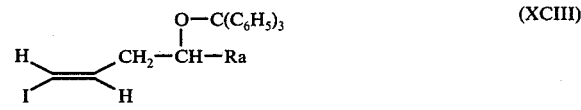

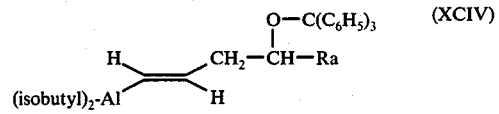

The starting 1-hydroxy-2-oxoalkanes for this procedure may be prepared in a variety of ways well-known to the literature [see P. A. Levene and M. L. Maller, Journ. Biol. Chem., 79, 475 (1928) and I. Forgo and J. Buchi, Pharm. Acta Helv., 45, 227 (1970)]. In Flowsheet J which follows Ra is an alkyl group of 3 to 10 carbon atoms optionally substituted with 1 or 2 lower alkyl groups each of from 1 to 3 carbon atoms.

FLOWSHEET E

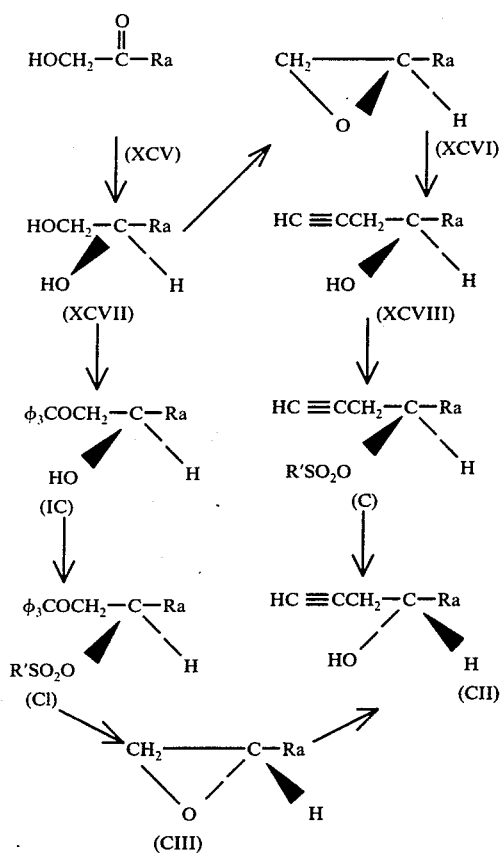

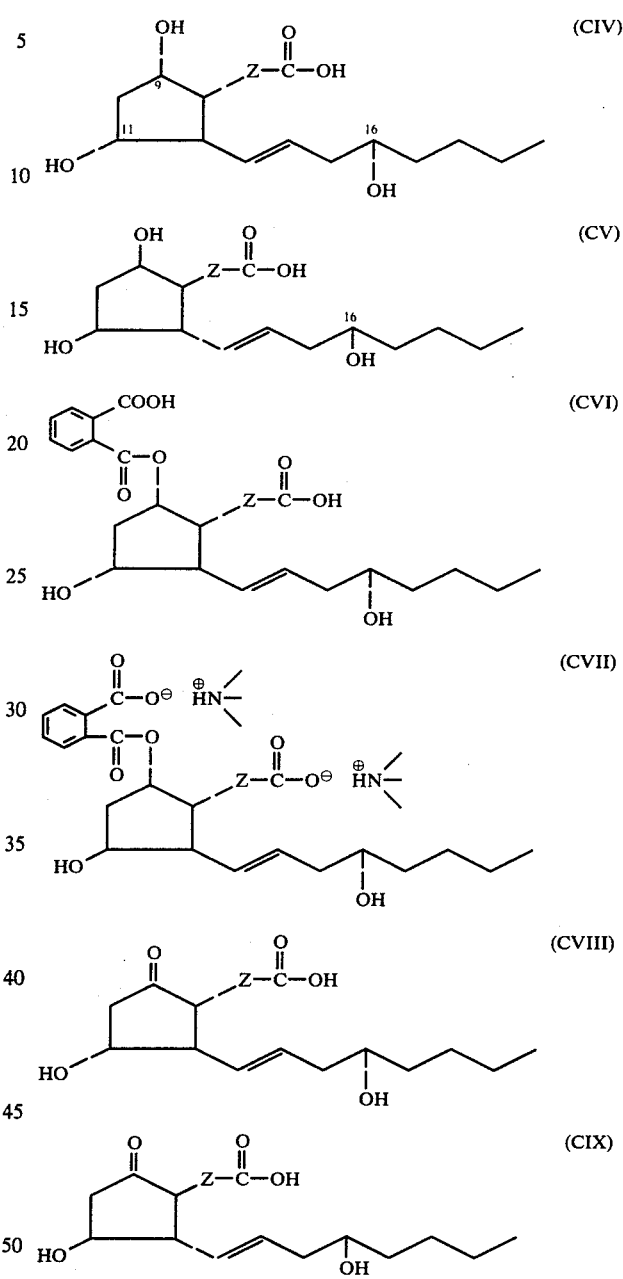

Additional procedures, well-understood in the literature, for effecting the resolution of racemic prostenoic acids and esters of this invention are described below.

In these procdures a 9-oxo-11α,16(S)-dihydroxy-5-cis, 13-trans-prostadienoic acid and its 9α-hydroxy derivative are used for illustrative purposes, it being understood, however, that the procedures are general and have applicability to the other products of this invention, particularly to those derivatives wherein the 11-position is not substituted with an oxy function.

Conversion of a 9α-hydroxy racemate (the component enantiomers are illustrated by CIV and CV below) wherein the $C_{11}$ and $C_{16}$ hydroxy functions have first been preferentially blocked by tetrahydropyranyl or trialkylsilyl groups, to the corresponding phthalate half acid-ester, deblocking the $C_{11}$ and $C_{16}$ hydroxy functions and conversion of the diacid (e.g., CVI) to a bis salt (e.g., CVII) with an optically active amine (e.g., 1-(−)-α-methylbenzylamine, D-(+)-α-methylbenzylamine, brucine, dehydroaebietylamine, styrychnine, quinine, cinchonine, cinchonindine, quinidine, ephedrine, deoxyephedrine, amphetamine, (+)-2-amino-1-butanol, (−)-2-amino-1-butanol and the like). The resulting diastereomers are then separated by fractional crystallization and the individual components are then converted by acidification and saponification to the individual optically active parent 9α-hydroxy enantiomers (CIV) and (CV), oxidation of which after preferential blocking of the $C_{11}$ and $C_{16}$ hydroxy functions with tetrahydropyranyl or trialkylsilyl groups, provides the corresponding individual 9-oxo enantiomers (CVIII) and (CIX). (For an appropriate literature procedure see E. W. Yankee, C. H. Lin and J. Fried, Journ. Chem. Soc., 1972, 1120).

Another procedure involves conversion of the 9α-hydroxy racemate (as the prostenoic acid ester and with the $C_{11}$ and $C_{16}$ alcohol functions preferentially blocked as tetrahydropyranyl or trialkylsilyl ethers) to the diastereomeric carbamates with an optically active isocyanate, e.g., (+)-1-phenylethylisocyanate or (−)-1-phenylethylisocyanate, followed by deblocking. Separation of the diastereomers, for example (CX) and (CXI) can be accomplished by fractional crystallization or by the usual chromatographic procedures, or if necessary by high speed liquid chromatography involving, if necessary, recycling techniques. Base-treatment of the individual diastereomeric carbamates affords the individual diastereomeric alcohols, for example (CIV) and (CV).

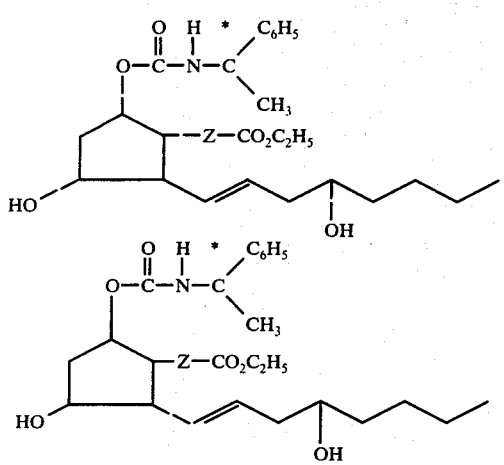

It is also possible to effect resolution of a 9α-hydroxy racemate, preferably as the prostenoate esters, by esterification of the 9α-hydroxy function (prior preferential blocking of $C_{11}$ and $C_{16}$ hydroxy functions as tetrahydropyranyl or trialkylsilyl ethers) with an optically active acid, via its acid chloride followed by deblocking the $C_{11}$ and $C_{16}$ alcohol groups. Suitable optically active acids include ω-camphoric acid, menthoxyacetic acid, 3α-acetoxy-Δ⁵-etianic acid, (−)-α-methoxy-α-trifluoromethylphenylacetic acid and (+)-α-methoxy-α-trifluoromethylphenylacetic acid, and the like. The resulting diastereomeric esters, for example (CXII) and (CXIII), are then separated by fractional crystallization or by chromatographic techniques including, if necessary, the use of high speed liquid chromatography. Saponification of the individual diastereomers then provides the individual 9α-hydroxyprostenoic acid enantiomers (CIV) and (CV).

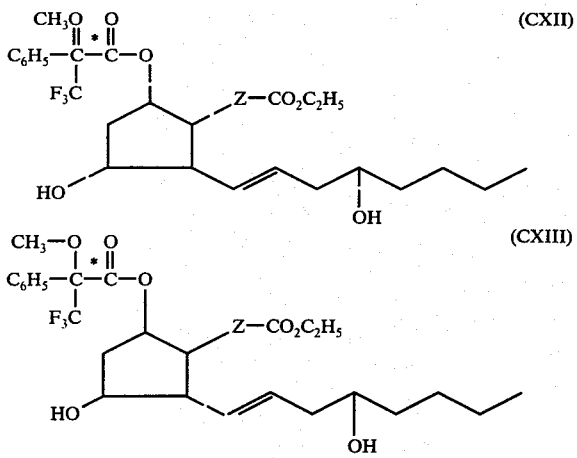

Another resolution procedure, less useful than the methods described above based on the 9α-hydroxy derivative but particularly applicable to 11-unsubstituted compounds of this invention, involves derivatization of the keto function of a racemic 9-oxoprostenoic acid or ester illustrated by (CVIII and CIX) with the usual type of ketone derivatizing agent bearing an optically active center. The resulting mixture of diastereomeric derivatives can then be separated by fractional crystallization or by chromatography or, if necessary, by high speed liquid chromatography. The individual diastereomeric keto derivatives, for example (CXIV) and (CXV), are then convertable to the individual 9-oxo enantiomers (CVIII) and (CIX) by any of the usual cleavage techniques, provided that they are sufficiently mild so as not to disturb the sensitive 11-hydroxy-9-keto system. (This latter point is not a problem with 11-unsubstituted derivatives.) Ketone reduction of the 9-oxo-enantiomer as described hereinabove then provides the corresponding 9α-hydroxy or 9β-hydroxy enantiomer. Among the optically active reagents useful for ketone derivatization are 1-α-aminoxy-α-methylpentanoic acid hydrochloride [E. Testa et al., Helv. Chimica Acta, 47 (3), 766 (1973)], menthylhydrazine, and 4-α-methylbenzylsemicarbazide. A useful procedure for the cleavage of oximes such as (CXIV) and (CXV) involves treatment of the oxime at about 60° C. for about 4 hours in 1:2 aqueous-tetrahydrofuran buffered with ammonium acetate and containing titanium trichloride.

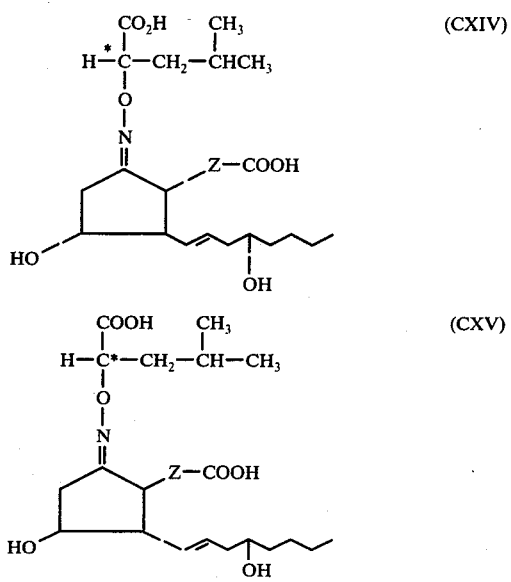

Other useful ketone derivatizing agents are optically active 1,2-glycols, e.g., D(−)-2,3-butanediol, or 1,2-dithiols, e.g., L(+)-2,3-butanedithiol. These are used to convert the 9-oxo derivative to 9,9-alkylenedioxa or 9,9-alkylenedithia derivatives, separation of diastereomers by chromatographic procedures followed by regeneration of the individual 9-oxo diastereomer by ketal cleavage all by procedures well-known in the art. Both ketalization and deketalization would have to be accomplished by procedures which would not disrupt the 11-oxo-9-keto system, which of course, is not a problem in the 11-unsubstituted series.

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various non-steroidal antiinflammatory agents (e.g., indomethacin, aspirin, and phenylbutasone), bronchodilators, anti-microbial agents, abortifacients, agents for the induction of labor, agents for the induction of menses, fertility-controlling agents oestrus regulators for the use in animal husbandry with cattle and other domestic animals and central nervous system regulatory agents. Certain of the novel compounds of this invention possess utility as intermediates for the preparation of other of the novel compounds of this invention.

The ring system of certain of the novel compounds of this invention allow them to be characterized as follows:

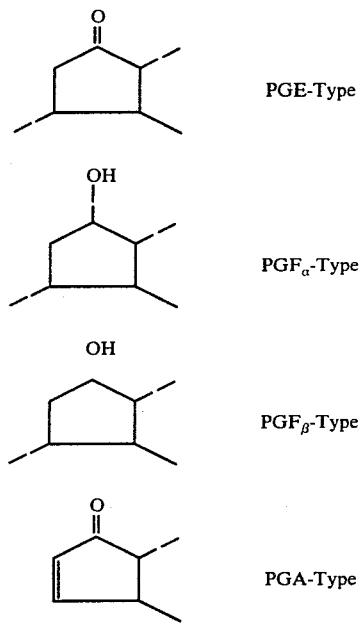

PGE-Type

PGF$_\alpha$-Type

PGF$_\beta$-Type

PGA-Type

The novel compounds of this invention possess the pharmacological activity described below as associated with the appropriate above-described prostaglandin type.

The known PGE, PGF$_\alpha$, PGF$_\beta$, and PGA compounds are all potent in causing multiple biological responses even at low doeses. For example, PGE$_1$ and PGE$_2$ are extremely potent in causing vasodepression and smooth muscle stimulation, and also are potent as antilipolytic agents. Moreoever, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandins analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

The 11-deoxy-PGE, PGF$_\alpha$and PGF$_\beta$compounds are additionally selective in that they are at most relatively very weak stimulants of smooth muscle. The 11-deoxy PGE compounds have a further advantage in that they are much more stable and have a longer "shelf-life" than the corresponding 11-hydroxy derivatives as described more fully hereinbelow.

Another advantage of the novel compounds of this invention, compared with the known prostaglandins, is that these novel compounds are administered effectively, orally, sublingually, intravaginally, buccally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGE$_1$, PGE$_2$, PGE$_3$, and dihydro-PGE$_1$, and the corresponding PGF$_\alpha$, PGF$_\beta$, and PGA, compounds, and their esters and pharmacologicallly acceptable salts, are extremely potent in causing various biological responses. For that reason, these compounds are useful for pharmacological purposes. See, for example, Bergstron et al., Pharmacol. Rev. 20, 1 (1968), and references cited therein. A few of those biological responses are systemic arterial blood pressure lowering in the case of the PGE, PGF$_\beta$, and PGA compounds as measured, for example, in anesthetized (phenobarbital sodium) pentolinium-treated rats with indwelling aortic and right heart cannulas; pressor activity, similarly measured, for the PGF$_\alpha$compounds; stimulation of smooth muscle as shown, for example, by tests on strips of guinea pig ileum, rabbit duodenum, or gerbil colon; potentiation of other smooth muscle stimulants; antilopolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli; e.g., arterial injury, and various biochemical stimuli, e.g., ADP, ATP, serotonin, thrombin, and collagen; and in the case of the PGE compounds, stimulation of epidermal proliferation and keratinization as shown when applied in culture to embryonic chick and rat skin segments.

Because of these biological responses, these known prostaglandins are useful to study, prevent, control, or alleviate a wide variety of disease and undesirable physiologically conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE and PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The $PGE_1$ compounds are useful whenever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg. per kg. of body weight per day are used, the exact dose depending on the age, weight, and condition of the patient or animal, and on the frequency and route of adminstration.

11α-Hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, $PGE_2$, for example, is useful in place of or in combination with less than usual amounts of these known smooth muscle stimulators, for example, to relieve the symptoms of paralytic ileus, or to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range of 0.01 to 2 mg. per kg. of body weight per day, the exact dose depending on the age, weight, and condition of the patient or animal.

The PGE, PGFβ and PGA compounds are useful as hypotensive agents to reduce blood pressure in mammals including man. For this purpose, the compounds are administered by intravenous infusion at the rate about 0.01 to about 50 μg per kg. of body weight per minute, or in a single or multiple doses of about 25 to 2500 μg. per kg. of body weight total per day.

The PGE, PGFα, and PGFβ compounds are useful in place of oxytoxin to induce labor in pregnant female animals, including man, cows, sheep, pigs, at or near term or in pregnant animals with intrauterine death of the fetus from about 20 weeks to term. For this purpose, the compound is infused intravenously at a dose 0.01 to 50 μg. per kg. of body weight per minute until or near the terminatin of the second stage of labor, i.e., expulsion of the fetus. These compounds are especially useful when the female is one or more weeks postmature and natural labor has not started, or 12 to 60 hours after the membranes have ruptured and natural labor has not yet started.

The PGEm PGFα, and PGFβ compounds are useful for controlling the reproductive cycle in ovulating female mammals, including humans and other animals. For that purpose, $PGF_2α$, for example, is administered systemically at a dose level in the range of 0.01 mg. to about 20 mg. per kg. of body weight, advantageously during a span of time starting approximately at the time of ovulation and ending approximately at the time of menses or just prior to menses. Additionally, expulsion of an embryo or fetus is accomplished by similar administration of the compound during the first third or the second third of the normal mammalian gestation period. Accordingly, they are useful as abortifacients. They are also useful for induction of menses during approximately the first two weeks of a missed menstrual period and accordingly are useful as contaceptive anti-fertility agents.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of several impaired renal blood flow, for example, the hepaorena syndrom and early kidney transplant rejection. In case of excessive or inappropriate ADH (antidiuretic hormone vasporessin) secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substituents thereof. Alternative routes of administration are subcutaneous or intramuscular near the site, oral, sublinqual, buccal, rectal, or vaginal. The exact dose depends on such factors as the route of adminstration, and the age, weight, and condition of the subject. To illustrate a wet dressing for topical application to second and/or third degree burns of skin area 5 to 25 square centimeters would advantageously involve use of an isotonic aqueous solution containing 2 to 2000 μg/ml. of the PGE compound. Esecially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steriods, for example, hydrocortisone, prednisolone, methylprednisolone, and fluoroprednisoline, each of those being used in the combination at the usual concentration suitable for its use alone.

The novel compounds of this invention induce the biological responses described hereinabove as associated with its particular prostaglandin type. These novel compounds are accordingly used for the above-described corresponding purposes in the same manner as described above.

The novel PGE, PGF$\beta$ and PGA compounds of this invention are also useful as bronchodilators for the treatment of asthma and chronic bronchitis; as such they may be conveniently administered by inhalation of aerosol sprays prepared in a dose range of about 10 $\mu$g. to about 10 mg. per ml. of a pharmacologically suitable liquid vehicle.

The protection against the ulcerogenic properties of indomethancin was determined in the following manner. Rats were starved for 48 hours (water was given ad libitum). Indomethacin (20 mg./kg. of body weight) was administered by the subcutaneous route and one-half the dose of the test compound was administered by gavage at the same time. After three hours, the second half of the test compound was administered also by gavage. Five hours after the administration of indomethacin the animals were decapitated snd the stomachs removed. The stomachs were washed with distilled water, blotted on gauze, cut along the larger curvature, and the contents rinsed with distilled water. The stomachs were spread out, pinned on a cork and visualized under magnifying glass for ulcers. The criteria for scoring of ulcers was as previously reported [Abdel-Galil et al. Brit. J. Pharmac. Chemotherapy 33:1-14 (1968)].

Score

0 — Normal stomach
1 — Petechial hemorrhage or pin point ulcer
2 — 1 or 2 small ulcers
3 — Many ulcers, a few large
4 — Many ulcers, mainly large A difference of at least 0.7 unit between the scores for control animals (treated with indomethacin but not test compound) and animals treated with indomethacin and test compound is considered indicative of activity from the test compound. (Control animals treated with neither indomethacin nor test compound give scores of about 0.5-0.8.) The results obtained in this assay with a typical compound of the present invention are set forth in Table I below.

TABLE I

| Compound | Total oral dose; mg./kg. of body weight | Score treated | control |
|---|---|---|---|
| 9-oxo-11$\alpha$,16-dihydroxy-5-cis,13-trans-prostadienoic acid | 0.78 | 1.0 | 3.0 |
| | 0.39 | 2.0 | 3.0 |

The novel compounds of the present inventon are also effective inhibitors of gastric acid secretion and of ulcer development in experimental animals, and thus are potentially valuable as agents for the control of gastric acid secretion and of gastric erosion and as anti-ulcer agents. Gastric acid secretion inhibitory action is usually measured by the "Shay rat" procedures ([1,2]) with some modifications as follows.

[1]Shay et al., Gastroenterology, 5, 43 (1954). [2]Shay et al., Gastroenterology, 26, 906 (1954).

The rats (male, CFE strain) were starved for 48 hours (water was given *ad libitum*) to permit evacuation of stomach contents. On the morning of the experiment, under either anesthia, the abdominal region was shaved and a midline incision (1-1½ inch) was made with a scapel. With the help of a closed curved hemostate the duodenum was picked up. Upon getting the duodenum into view, fingers were used to pull the stomach through the opening, the stomach was then gently manipulated with fingers to rid stomach of air and residual matter which were pushed through the pylorus. Two-5 inch sutures were drawn under the pyloric-duodenal puncture. A ligature, at the juncture, was formed with one of the threads. The second ligature was also formed but not tightened.

The test compound or the vehicle, usually 1 m./100 g. body weight, were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips. (Ocassionally, instead of an intraduodenal injection, animals were dosed by the oral or subcutaneous route. In the latter case, dosing was done at 0 and at 2 hours and the animals were sacrificed at 4 hours.)

Three hours later, the rats were decapitated and exanguinated, taking care that clood did not drain into the esophagus. The abdominal cavity was exposed by cutting with scissors and the esophagus close to the stomach was clamped off with a hemostat, the stomach was removed by cutting above the hemostat (the esophagus was cut) and between the two sutures. Extraneous tissue was removed, the stomach washed with saline and blotted on gauze. A slit was carefully made in the stomach which was held over a funnel and the contents were collected in a centrifuge tube. The stomach was further cut along the outside edge and turned inside out. Two ml. H$_2$O were used to wash the stomach contents into the respective centrifuge tube. The combined stomach contents and wash were then centrifuged for 10 minutes in the International Size 2 Centrifuge (setting at 30). The supernatant was collected, volume measured and recorded, 2 drops of a phenolphthalein indicator (1% in 95% ethanol) were added and the solution was titrated with 0.02N NaOH (or with 0.04N NaOH when large volumes of stomach contents were encountered( to pH 8.4 (because of usual coloring of the stomach contents, phenolphthalein was only used to permit visual indication that the end point was near) and the amount of acid present was calculated.

Compounds inducing inhibition of gastric acid secretion of 20% or more were considered active. In a representative operation, and merely be way of illustration, the results obtained with this assay with a typical compound of the present invention are given in Table II below.

TABLE II

| Compound | Subcutaneous dose, mg./kg. of body weight | Percent Inhibition |
|---|---|---|
| 9-oxo-11$\alpha$,16-dihydroxy-5-cis,13-trans-prosta-dienoic acid | 1.6 | 48 |
| | 0.8 | 44 |
| | 0.4 | 35 |

Inhibition of basal gastric acid secretion can be determined by the following procedure. Female Sprague-Dawley rats weighting 140-160 grams are fastened in individual cages for 18-24 hours. The rats are then lightly anesthetized with ether and their front teeth extracted to avoid destruction of the plastic cannula. A midline incision is then made and the stomach and duodenum exposed. A flanged polyvinyl tube is inserted into the fundic portion of the stomach and secured with a purse string suture line using 4-0 Mersilene. The rat is then dosed by injection of the compound into the duodenum (1.0 ml. per 100 gram body weight). After dosing, the abdominal wall and skin are closed using metal wound clips. The rat is replaced in a cage containing a longitudinal slit to allow the polyvinyl tube to hang freely. An 8 ml. plastic collecting tube is attached to the flanged cannula and hangs freely below the cage. The first 30 minute sample is discarded designating this time as zero. The collecting tube is attached again and samples removed at the end of 60 and/or 120 minutes. The hourly samples are then transferred to a 15 ml. centrifuge and centrifuged for 5-10 minutes. Total and sediment volume are then recorded with supernatent volume being used as volume of secretion. A 1 ml. or less aliquot is then removed and placed in a 50 ml. beaker containing 10 ml. of distilled water. This sample is then titrated using 0.01N to Na H to pH 7.0 using a Beckman zeromatic pH meter. Volume, titratable acidity (meq/L) and total acid output (μeq/hour) are recorded. Percent inhibition is determined by comparison with the appropriate control. Groups of three rats are used for preliminary testing, and groups of six rats are used for dose-response evaluations. All compounds are administered in a vehicle consisting of 0.5% methocel, 0.4% tween 80, and saline at a constant volume of 1 ml./100 gram rat. Samples are dispersed by sonification. Percent inhibition is calculated on basis of concurrent vehicle control.

In Table III which follows is given the effect on total acid output after 60 minutes of a 10 mg./kg. intraduodenal dose of representative compounds of this invention.

TABLE III

Inhibition of Gastric Acid Secretion in the Acute Gastric Fistula Rat

| Compound | Intraduodenal dose, mg./kg. of body weight | % Inhibition of Total Acid or Output |
|---|---|---|
| 9-oxo-11α,16-dihydroxy-5-cis,13-trans-prostadienoic acid | 10 | 69 |
|  | 2.5 | 42 |
| methyl 9-oxo-11α,16-dihydroxy-5-cis,13-trans-prostadienoate | 10 | 100 |
|  | 1.25[b] | 75 |
|  | 0.625[b] | 51 |
| decyl 9-oxo-11α,16-dihydroxy-5-cis,13-trans-prostadienoate | 10 | 60 |
| 9-oxo-11α-tetrahydropyranyloxy-16-triphenylmethoxy-5-cis,13-trans-prostadienoic acid | 10 | 68 |
| 9-oxo-11α,16-dihydroxy-20-methyl-5-cis,13-trans-prostadienoic acid | 10 | 42 |
| 9-oxo-11α,16-dihydroxy-20-methyl-5-cis,13-trans,17-trans-prostatrienoic acid | 10 | 44 |
| 9-oxo-11α-hydroxy-15-hydroxymethyl-5-cis,13-trans-prostadienoic acid | 10 | 50 |
| 9-oxo-11α,16-dihydroxy-17-methyl-5-cis,13-trans-prostadienoic acid | 10 | 93 |
|  | 10[b] | 89 |
|  |  | 85[c] |
| methyl 9-oxo-11α,16-dihydroxy-17-methyl-5-cis,13-trans-prostadienoate | 10 | 76 |
| 9α,11α,16-trihydroxy-17-methyl-5-cis,13-trans-prostadienoic acid | 10 | 96 |
|  |  | 98[c] |
|  | 2.5 | 66 |
|  |  | 62[c] |
|  | 0.63 | 55 |
|  |  | 47[c] |
| 9-oxo-16-hydroxy-5-cis,10,13-trans-prostatrienoic acid | 10 | 44 |
| 9-oxo-16-hydroxy-5-cis,10,13-trans,17-trans-prostatetraenoic acid | 10 | 83 |
|  | 10[b] | 43 |

Footnotes - Table III
[a]After 60 minutes.
[b]Oral dose.
[c]After 120 minutes.

The compounds of this invention are useful as bronchodilators for the treatment of asthma and chronic bronchitis. Bronchodilator activity is determined in guinea pigs against bronchospasms elicited by intravenous injections of 5-hydroxytryptamine, histamine or acetylcholine by the Konzett procedure. [See J. Lullling, P. Lievens, F. El Sayed and J. Prignot, Arzneimittel-Forschung, 18, 955 (1968).]

In Table IV which follows bronchodilator activity for representative compounds of this invention against one or more of three spasmogenic agents is expressed as an $ED_{50}$ determined from the results obtained with three logarithmic cummulative intravenous doses. In this assay, these compounds of this invention provide an effect of longer duration than does natural 1-PGE$_1$ or 1-PGE$_2$.

TABLE IV

Bronchodilator Activity (Konzett Assays)

| | $ED_{50}$, mg./kg. Spasmogenic Agent | | |
|---|---|---|---|
| Compound | 5-hydroxytryptamine | histamine | Acetylcholine |
| 9-oxo-11α,16-dihydroxy-5-cis,13-trans-prostadienoic acid | 0.0036 | 0.0021 | 0.0173 |
| 9-oxo-11α,16-dihydroxy-20-methyl-5-cis,13-trans-prostadienoic acid | 0.00032 | 0.00029 | 0.00072 |
| 9-oxo-11α,16-dihydroxy-17-methyl-5-cis,13-trans-prosta- | | | |

TABLE IV-continued

| | Bronchodilator Activity (Konzett Assays) | | |
|---|---|---|---|
| | ED$_{50}$, mg./kg. Spasmogenic Agent | | |
| Compound | 5-hydroxytryptamine | histamine | Acetylcholine |
| dienoic acid | 0.0019 | 0.00049 | 0.003 |
| 9-oxo-11α,16-dihydroxy-20-methyl-5-cis,13-trans,17-trans-prostatrienoic acid | 0.0012 | 0.0022 | 0.004 |
| 9-oxo-16-hydroxy-20-methyl-5-cis,10,13-trans,17-trans-prostatetraenoic acid | 0.625 | 0.369 | 2.28 |
| 9-oxo-16-hydroxy-5-cis,10,13-trans-prostatrienoic acid | 0.125 | 0.081 | 1.54 |

The novel compounds of the present invention are useful as hypotensive agents and their hypotensive activity was demonstrated in the following test procedure. This procedure is a modification of the techniques described by Pike et al., Prostaglandins, Nobel Symposium 2, Stockholm, June, 1966; P. 165.

Male Wistar strain rats (Royal Hart Farms) averaging approximately 250 grams in weight were fastened to rat boards in a supine position by means of canvas vests and limb ties. The femoral area was infiltrated subcutaneously with lidocaine and the iliac artery and vein were exposed and cannulated. Arterial blood pressure (systolic/diastolic) was recorded using a Statham P$_{23}$ Db pressure transducer-Offner dynograph system. To obtain a stable blood pressure, the animals were anethetized before use with pentobarbital, 30 mg./kg. of body weight intravenously, and also were given hexamethoxium bitartrate, 2 mg./kg. of body weight intravenously. The test compounds were prepared by ultrasonic dispersion in a Saline-Tween 80 ® vehicle. A constant intravenous dose volume of 0.5 ml. was administered and test doses ranged from 0.1 to 10.0 mg./kg. of body weight.

In Table V below are recorded the per-cent decrease from normal of mean arterial blood pressure induced by given doses of representative compounds of this invention.

TABLE V

| | Hypotensive Response (normotensive rat) | |
|---|---|---|
| Compound | Dose, mg./kg. of Body Weight | % Decrease in Mean Arterial Blood Pressure |
| 9-oxo-11α,16-dihydroxy-5-cis,13-trans-prostadienoic acid | 2.1 | 27 |
| 9-oxo-11α,16-dihydroxy-17-methyl-5-cis,13-trans-prostadienoic acid | 1.0 | 42 |
| methyl 9-oxo-11α,16-dihydroxy-17-methyl-5-cis,13-trans-prostadienoate | 1.2 | 42 |
| 9β,11α,16-trihydroxy-5-cis,13-trans-prostadienoic acid | 2.1 | 24 |

In the examples which follow, unless otherwise specified, the products include all possible optical isomers.

EXAMPLE 1

Preparation of all cis-2-(6-carboxy-2-cis-hexenyl)-3,4-oxidocyclopentanol

A solution of 1.42 g. (10.0 moles) of all-cis-5-hydroxy-2,3-oxidocyclopentylacetaldehyde-γ-lactol (E. J. Corey and R. Noyori, Tetrahedron Letters, 1970, 311) in 5 ml. of DMSO is added to a stirred solution of the Wittig reagent [E. J. Corey et al., JACS, 91 5675 (1969)] prepared from 13.3 g. (0.30 moles) of 4-carboxybutyltriphenylphosphonium bromide (Example 8) 2.52 g. (0.60 moles) of 57% sodium hydride dispersion, and 70 ml. of DMSO at 16° C. during 1 minute.

The solution is stirred at ambient temperature for 20 hours and poured into a stirred mixture of methylene chloride, ice, and hydrochloric acid. The organic phase is separated, and the aqueous phase is extracted with methylene chloride, saturated with sodium chloride, and extracted with ether. The combined organic extracts are partitioned with sodium bicarbonate. The aqueous basic extract is acidified with dilute HCl, saturated with sodium chloride, and extracted with ethyl acetate. The extract is washed with brine, dried over magnesium sulfate, and concentrated to give the crude title compound as an orange oil.

EXAMPLE 2

Preparation of all-cis-2-(6-carboxy-2-cis-hexenyl)-3,4-oxidocyclopentanone

To a stirred solution of ca. 1.6 moles of crude all-cis-2-(6-carboxy-2-cis-hexenyl)-3,4-oxidocyclopentanol (Example 1) in 1.6 ml. of ether is added 1.6 ml. of 4.0 N chromic acid in 4N sulfuric acid at 0° C. during 9 minutes. After stirring for 5 minutes at 0° C. the solution is diluted with brine, ether, and ethyl acetate. The organic phase is treated with isopropanol, washed with brine and dried over magnesium sulfate. Evaporation of the solvent gives the subject compound as an oil.

EXAMPLE 3

Preparation of 2-(6-carboxy-2-cis-hexenyl)-4-hydroxycyclopent-2-en-1-one

A solution of 1.0 mmole of all-cis-(6-carboxy-2-cis-hexenyl)-3,4-oxidocyclopentanone (Example 2) and 3.0 mmoles of sodium carbonate in 15 ml. of water is allowed to stand at room temperature for 3 hours. The solution is acidified with HCl, saturated with sodium chloride, and extracted with ether. The extract is washed with brine, dried over magnesium sulfate, and concentrated to give a mixture of the title compound and the isomeric compound, 2-(6-carboxy-2-cis-hexenyl)-3-hydroxycyclopent-4-en-1-one. Further treatment of this mixture with N/10 sodium hydroxide at room temperature for 30 minutes causes the rearrangement of the latter isomer to the title compound, which is isolated from basic solution as above.

EXAMPLE 4

Preparation of
2-(6-carboxy-2-cis-hexenyl)-4-hydroxycyclopent-2-en-1-one

Treatment of cis-anti-cis-5-hydroxy-2,3-oxidocylopentylacetaldehyde-γ-lactol (E. J. Corey and R. Noyori Tetrahedron Letters, 1970, 311), prepared from the corresponding lactone and diisobutylaluminum hydride as described for the preparation of the corresponding cis-syn-cis lactol, with 4-carboxybutyltriphenylphosphonium bromide as described in Example 1 is productive of 2β-(6-carboxy-2-cis-hexenyl)-3α,-4α-oxidocyclopentan-1β-ol which on oxidation by the method of Example 2 provides 2β-(6-carboxy-2-cis-hexenyl)-3α,4α-oxidocyclopentanone, which in turn on treatment with aqueous base by the procedure of Example 3 furnishes the subject compound.

EXAMPLE 5

Preparation of
2-(6-carboxy-2-cis-hexenyl)-3,4-oxidocyclopentanol

A solution of 5.0 g. (35 mmoles) of 5-hydroxy-2,3-oxidocyclopentylacetaldehyde- -lactol (isomeric mixture: E. J. Corey and R. Noyori, Tetrahedron Letters, 1970 311) in 25 ml. of DMSO is added during 0.5 minute at 20° C. to a stirred solution of the Wittig reagent [E. J. Corey et al., JACS, 91, 5675 (1969); also Example 6] and dimsyl sodium prepared from 23.5 g. (53 mmoles) of 4-carboxybutyltriphenylphosphonium bromide, 6.1 g. (140 mmoles) of 57% sodium hydride dispersion, and 230 ml. of DMSO (dimethylsulfoxide).

The solution is stirred at ambient temperatures for 2 hours and poured into a stirred mixture of methylene chloride, ice, and hydrochloric acid. The reaction mixture is worked up as described in Example 1, and the crude product is purified by dry column chromatography on silica gel to provide the title compound (mixture of two stereoisomers) as an oil, IR (film) 3450, 1710, and 832 cm$^{-1}$.

EXAMPLE 6

Preparation of
2-(6-carboxy-2-cis-hexenyl)-3,4-oxidocyclopentanone

A stirred solution of 2.98 g. (13.2 mmoles) of 2-(6-carboxy-2-cis-hexenyl)-3,4-oxidocyclopentanol (Example 5) in 66 ml. of acetone is treated dropwise with 3.30 ml. of 8N chromic acid in 8N $M_2SO_4$ during 20 minutes at −10° to −5° C. The solution is stirred at −5° C. for 10 minutes and treated successively with a few drops of isopropanol and 12 ml. of water. The mixture is filtered, and the filtrate is concentrated, saturated with sodium chloride, and extracted with ethyl acetate. The extract is washed with brine, dried over $MgSO_4$, and evaporated to give an oil, IR (film) 1740, 1710, and 840 cm$^{-1}$.

EXAMPLE 7

Preparation of
2-(6-carboxy-2-cis-hexenyl)-4-hydroxycyclopent-2-en-1-one

A solution (pH of 10.2–10.5) of 2.42 g. (10.8 mmoles) of 2-(6-carboxy-2-cis-hexenyl)-3,4-oxidocyclopentanone (Example 6), 4.58 g. (43.2 mmoles) of sodium carbonate, and 216 ml. of water is allowed to stand at room temperatures under nitrogen for 24 hours. The solution is acidified at 15° C. with hydrochloric acid and extracted with ethyl acetate. The extract is washed with brine, dried over $MgSO_4$, and evaporated to give an oil; IR (film) 1700 (carbonyl groups) and 1630 cm$^{-1}$ (conjugated olefin); NMR 7.11 (1), 5.54 (2), and 495 (1)δ.

EXAMPLE 8

Preparation of 4-carboxybutyltriphenylphosphonium bromide

A mixture of 103 g. of 5-bromovaleric acid and 152 g. of triphenylphosphine in 400 ml. of acetonitrile is refluxed for 48 hours, cooled, diluted with 100 ml. of benzene and allowed to crystallize. The crystals are filtered, washed with benzene and ether, to yield colorless material, m.p. 207°–209° C.

EXAMPLES 9–15

Treatment of the indicated ω-bromoalkanoic acids of Table 1 below with triphenylphosphine by the method described in Example 8 produces the phosphonium bromides of the table.

TABLE 1

| Example | Starting ω-bromo-alkanone acid | Product Phosphonium bromide |
| --- | --- | --- |
| 9 | 4-bromo-n-butyric acid | 3-carboxypropyltriphenylphosphonium bromide |
| 10 | 6-bromo-n-hexanoic acid | 5-carboxypentyltriphenylphosphonium bromide |
| 11 | 7-bromo-n-heptanoic acid | 6-carboxyhexyltriphenylphosphonium bromide |
| 12 | 5-bromo-4-methyl-n-pentanoic acid | (2-methyl-4-carboxybutyl)triphenylphosphonium bromide |
| 13 | 5-bromo-4(R)-methyl-n-pentanoic acid[1] | (2[R]-methyl-4-carboxybutyl)triphenylphosphonium bromide |
| 14 | 5-bromo-4-ethyl-n-pentanoic acid | (2-ethyl-4-carboxybutyl)triphenylphosphonium bromide |
| 15 | 5-bromo-4-propyl-n-pentanoic acid | (2-propyl-4-carboxybutyl)triphenylphosphonium bromide |

[1] J. S. Dalby, G. W. Kenner and R. C. Sheppard, J. Chem. Soc., 4387 (1962).

EXAMPLES 16–22

Treatment of 5-hydroxy-2,3-oxidocyclopentylacetaldehyde-γ-lactol (isomeric mixture) with the Wittig reagent prepared from the indicated phosphonium bromides of Table 2 below, all by the procedures of Examples 1 and 5, is productive of the product compounds of the table.

TABLE 2

| Example | Reagent phosphonium bromide of Example | Product 3,4-oxidocyclopentanol (isomeric mixture) |
| --- | --- | --- |
| 16 | 9 | 2-(5-carboxy-2-cis-pentenyl)-3,4-oxidocyclopentan-1-ol |
| 17 | 10 | 2-(7-carboxy-2-cis-heptenyl)-3,4-oxidocyclopentan-1-ol |
| 18 | 11 | 2-(8-carboxy-2-cis-octenyl)-3,4-oxidocyclopentan-1-ol |
| 19 | 12 | 2-(6-carboxy-4-methyl-2-cis-hexenyl)-3,4-oxidocyclopentan-1-ol |
| 20 | 13 | 2-(6-carboxy-4(R)-methyl-2-cis-hexenyl)-3,4-oxidocyclopentan-1-ol |
| 21 | 14 | 2-(6-carboxy-4-ethyl-2-cis-hexenyl)-3,4-oxidocyclopentan-1-ol |
| 22 | 15 | 2-(6-carboxy-4-propyl- |

TABLE 2-continued

| Example | Reagent phosphonium bromide of Example | Product 3,4-oxidocyclopentanol (isomeric mixture) |
| --- | --- | --- |
|  |  | 2-cis-hexenyl)-3,4-oxidocyclopentan-1-ol |

EXAMPLES 23–29

Oxidation of the cyclopentanols indicated in Table 3 below by the method described in Example 6 furnishes the corresponding product 3,4-oxidocyclopentanones of the table.

TABLE 3

| Example | Starting cyclopentan-1-ol of Example | Product 3,4-oxidocyclopentan-1-one |
| --- | --- | --- |
| 23 | 16 | 2-(5-carboxy-2-cis-pentenyl)-3,4-oxidocyclopentan-1-one |
| 24 | 17 | 2-(7-carboxy-2-cis-heptenyl)-3,4-oxidocyclopentan-1-one |
| 25 | 18 | 2-(8-carboxy-2-cis-octenyl)-3,4-oxidocyclopentan-1-one |
| 26 | 19 | 2-(6-carboxy-4-methyl-2-cis-hexenyl)-3,4-oxidocyclopentan-1-one |
| 27 | 20 | 2-(6-carboxy-4(R)-methyl-2-cis-hexenyl)-3,4-oxidocyclopentan-1-one |
| 28 | 21 | 2-(6-carboxy-4-ethyl-2-cis-hexenyl)-3,4-oxidocyclopentan-1-one |
| 29 | 22 | 2-(6-carboxy-4-propyl-2-cis-hexenyl)-3,4-oxidocyclopentan-1-one |

EXAMPLES 30–36

Alkaline treatment of the 3,4-oxidocyclopentanones of Table 4 below by the process described in Example 7 is productive of the 4-hydroxycyclopentenones of the table.

TABLE 4

| Example | Starting 3,4-oxidocyclopentanone of Example | Product 4-hydroxycyclopent-2-en-1-one |
| --- | --- | --- |
| 30 | 23 | 2-(5-carboxy-2-cis-pentenyl)-4-hydroxycyclopent-2-en-1-one |
| 31 | 24 | 2-(7-carboxy-2-cis-heptenyl)-2-hydroxycyclopent-2-en-1-one |
| 32 | 25 | 2-(8-carboxy-2-cis-octenyl)-4-hydroxycyclopent-2-en-1-one |
| 33 | 26 | 2-(6-carboxy-4-methyl-2-cis-hexenyl)-4-hydroxycyclopent-2-en-1-one |
| 34 | 27 | 2-(6-carboxy-4(R)-methyl-2-cis-hexenyl)-4-hydroxycyclopent-2-en-1-one |
| 35 | 28 | 2-(6-carboxy-4-ethyl-2-cis-hexenyl)-4-hydroxycyclopent-2-en-1-one |
| 36 | 29 | 2-(6-carboxy-4-propyl-2-cis-hexenyl)-4-hydroxycyclopent-2-en-1-one |

EXAMPLE 37

Preparation of 4-tetrahydropyranyloxy-2-(6-carbotetrahydropyranyloxy-2-cis-hexenyl)cyclopent-2-en-1-one A vigorously stirred, ice-cold solution of 9.45 g. (42.5 mmoles) of 2-(6-carboxy-cis-2-hexenyl)-4-hydroxycyclopent-2-en-1-one (Example 7) and 14.3 g. (170 mmoles of dihydropyran in 212 ml. of methylene chloride is treated with 81 mg. (0.425 mmoles) of p-toluenesulfonic acid monohydrate. After stirring for 5 minutes at 0° C. and 60 minutes at 25° C. the solution is poured into a stirred mixture of 40 ml. of saturated brine, 40 ml. of saturated sodium bicarbonate and 80 ml. of water. The organic phase is washed with brine, dried over magnesium sulfate, and concentrated to give an oil, $\nu$ max (film) 1730 (ester carbonyl), 1710 (ketone carbonyl), and 1030 cm$^{-1}$ (tetrahydropyranyloxy groups.

EXAMPLES 38–44

Treatment of the 4-hydroxycyclopent-2-en-1-ones listed in Table 5 below with dihydropyran in the manner of Example 37 is productive of the corresponding bis-tetrahydropyranyl ether-esters of the table.

TABLE 5

| Example | Starting 4-hydroxycyclopent-2-en-1-one of Example | Product bis-tetrahydropyranyl ether-ester |
| --- | --- | --- |
| 38 | 30 | 4-tetrahydropyranyloxy-2-(5-carbotetrahydropyranyloxy-2-cis-pentenyl)cyclopent-2-en-1-one |
| 39 | 31 | 4-tetrahydropyranyloxy-2-(7-carbotetrahydropyranyloxy-2-cis-heptenyl)-cyclopent-2-en-1-one |
| 40 | 32 | 4-tetrahydropyranyloxy-2-(8-carbotetrahydropyranyloxy-2-cis-octenyl)-cyclopent-2-en-1-one |
| 41 | 33 | 4-tetrahydropyranyloxy-2-(6-carbotetrahydropyranyloxy-4-methyl-2-cis-hexenyl)-cyclopent-2-en-1-one |
| 42 | 34 | 4-tetrahydropyranyloxy-2-(6-carbotetrahydropyranyloxy-4(R)-4-methyl)-2-cis-hexenyl-cyclopent-2-en-1-one |
| 43 | 35 | 4-tetrahydropyranyloxy-2-(6-carbotetrahydropyranyloxy-4-ethyl-2-cis-hexenyl)-cyclopent-2-en-1-one |
| 44 | 36 | 4-tetrahydropyranyloxy-2-(6-carbotetrahydropyranyloxy-4-propyl-2-cis-hexenyl)cyclopent-2-en-1-one |

EXAMPLE 45

Preparation of 4-(trimethylsiloxy)-2-(6-carbotrimethylsiloxy-2-cis-hexenylcyclopent-2-en-1-one To a solution of 5 g. of 2-(6-carboxy-2-cis-hexenyl-4-hydroxy-cyclopent-2-en -1-one (Example 7) in 10 ml. of dry N,N-dimethylformamide is added 5.4 g. of trimethylsilyl chloride in a nitrogen atmosphere. To the resulting solution cooled in a tap water bath is added 5.05 g. of triethylamine in 10 ml. of N,N-diemthylformamide dropwise. The resulting mixture is stirred at 60° C. in an oil-bath for 2 hours, then at ambient temperatures for 18 hours. Triethylamine hydrochloride is removed by filtration and the filtrate is taken to dryness. The residual oil is further purified by distillation at high vacuum.

EXAMPLES 46-63

Treatment of the 4-hydroxycyclopent-2-en-1-ones listed in Table 6 below with the indicated trialkylsilyl chloride by the method described in Example 45 is productive of the bis-trialkylsilyl ether-esters of the table.

TABLE 6

| Example | Starting 4-hydroxy-cyclopentenone of Example | Trialkylsilyl-chloride | product bis-trialkylsilyl ether-ester |
|---|---|---|---|
| 46 | 30 | $(CH_3)_3SiCl$ | 4-trimethylsiloxy-2-(5-carbotrimethylsiloxy-2-cis-pentyl)cyclopent-2-en-1-one |
| 47 | 31 | $(CH_3)_3SiCl$ | 4-trimethylsiloxy-2-(7-carbotrimethylsiloxy-2-cis-heptenyl)cyclopent-2-en-1-one |
| 48 | 32 | $(CH_3)_3SiCl$ | 4-trimethylsiloxy-2-(8-carbotrimethylsiloxy-2-cis-octenyl)cyclopent-2-en-1-one |
| 49 | 7 | dimethyliso-propyl silyl chloride[a] | 4-dimethylisopropylsiloxy-2-(6-carbodimethyl-isopropylsiloxy-2-cis-hexenyl)cyclopent-2-en-1-one |
| 50 | 33 | $(CH_3)_3SiCl$ | 4-trimethylsilyloxy-2-(6-carbotrimethylsilyloxy-4-methyl-2-cis-hexenyl)cyclopent-2-en-1-one |
| 51 | 34 | $(CH_3)_3SiCl$ | 4-trimethylsilyloxy-2-(6-carbotrimethylsilyloxy-4(R)-methyl-2-cis-hexenyl)cyclopent-2-en-1-one |
| 52 | 35 | $(CH_3)_3SiCl$ | 4-trimethylsilyloxy-2-(6-carbotrimethylsilyloxy-4-ethyl-2-cis-hexenyl)cyclopent-2-en-1-one |
| 53 | 36 | $(CH_3)_3SiCl$ | 4-trimethylsilyloxy-2-(6-carbotrimethylsilyloxy-4-propyl-2-cis-hexenyl)cyclopent-2-en-1-one |

[a]E. J. Corey, R. K. Varma, J. Amer. Chem. Soc., 93, 7320 (1970).

EXAMPLE 54

Preparation of 1-oxa-2-hydroxy-bicyclo[3.3.0]oct-4-ene

A solution of 6.2 g. (50 mmole) of the lactone of cis-2-hydroxycyclopent-4-ene-1-acetic acid [P. A. Grieco, J. Org. Chem., 37, 2363 (1972)] in 350 ml. toluene (dried over molecular seieves) is cooled to 31 75° C. and treated dropwise under nitrogen with 84 ml. 0.89 m diisobutyl aluminum hydride (10.55 g., 74 mmole) over a period of about one hour maintaining the temperature at −74° ± 2° C. The resulting clear solution is stirred at −75° C. for two hours and poured with stirring into a mixture of 15 ml. of concentrated hydrochloric acid and 300 ml. of ice water. The mixture is stirred while warming to room temperature. The layers are separated and the aqueous layer is treated with salt and extracted with three small portions of ether. The combined organic portions are dried over sodium sulfate and evaporated at reduced pressure (75° C. water bath) to yield the product (homogeneous by thin layer chromatography) as a pale yellow mobile liquid.

EXAMPLE 55

Preparation of 1-hydroxy-2-(6-carboxy-2-cis-hexenyl)cyclopent-3-ene

A solution of the sodium salt of dimethyl sulfoxide is prepared by stirring under nitrogen a mixture of 160 ml. dry dimethyl sulfoxide (dried over molecular sieves and a few pellets of calcium hydride) with 6.0 g. (0.25 mole) of sodium hydride (prepared by washing 10.5 g. of 57% sodium hydride dispersion in mineral oil with two 30 ml. portions of hexane). The mixture is warmed with stirring at 75° C. (oil bath) for 2.5 hours.

This solution is added during about five minutes to a solution under nitrogen of 44 grams (0.1 mole) of 4-carboxybutyltriphenylphosphonium bromide (Example 8) in 180 ml. of dry dimethyl sulfoxide. The resulting dark reddish brown solution is stirred for ten minutes, cooled to room temperature and treated with a solution of crude 1-oxa-2-hydroxy-bicyclo[3.3.0]oct-4-ene (6.2 g., 50 mmole) (Example 54) in 20 ml. of anhydrous dimethyl sulfoxide. The resulting solution is stirred 16 hours and then treated with 250 ml. of ice water.

This brown solution is extracted with two portions of ether to remove neutral material then made strongly acidic with hydrochloric acid. The solution is extracted into four 100 ml. portions of methylene chloride. The combined methylene chloride extracts are washed with water, then extracted with four 100 ml. of portions of 5% sodium bicarbonate. The combined aqueous extracts are washed with methylene chloride and made acidic to Congo Red with concentrated hydrochloric acid. The mixture is extracted with three 100 ml. portions of methylene chloride. The organic extracts are combined, dried over sodium sulfate and the solvent is evaporated at reduced pressure. The residue (an oily solid) is extracted several times with ether and the ethereal extracts are combined and evaporated at reduced pressure to yield the crude product as a dark oil. The product is purified by chromatography on silica gel, eluting with ether. The product is a colorless liquid.

EXAMPLE 56

Preparation of 2-(6-carboxy-2-cis-hexenyl)cyclopent-3-en-1-one

A solution of 3.2 g of 1-hydroxy-2-(6-carboxy-2-cis-hexenyl)cyclopent-3-ene (Example 55) in 60 ml. of reagent acetone is treated dropwise with a total of 6 ml of 8N chromic acid in sulfuric acid at 0° C. The oxidation is rather slow. The resulting mixture is dissolved in 200 ml. of water and the solution is extracted with six 50 ml. portions of ether. The combined ethereal extracts are dried over sodium sulfate and the solvent is evaporated at reduced pressure to yield the product as a yellow oil.

EXAMPLE 57

Preparation of 2-(6-carboxy-2-cis-hexenyl)cyclopent-2-en-1-one

A solution of 3 g. of crude 2-(6-carboxy-2-cis-hexenyl)cyclopent-3-en-1-one (Example 56) in 100 ml. of aqueous sodium carbonate (pH: 10-11) is stirred at ambient temperatures under nitrogen for 4 hours. The solution is acidified to Congo Red and extracted into ether. The ethereal extracts are dried over sodium sulfate and evaporated at reduced pressure to afford the product.

See also P. A. Griesco and J. J. Reap, J. Org. Chem., 38, 3413 (1973).

EXAMPLES 58-64

Treatment of 1-oxa-2-hydroxy-bicyclo[3.3.0]oct-4-ene (Example 549 by the procedure described in Example 55 with the yields derived from the phosphonium bromides listed in Table 7 below furnishes the product 1-hydroxy-cyclopent-3-enes of the table.

TABLE 7

| Example | Starting phosphonium bromide of Example | Product 1-hydroxy-2-(ω-carboxy-2-cis-alkenyl)-cyclopent-3-enes |
|---|---|---|
| 58 | 9 | 1-hydroxy-2-(5-carboxy-2-cis-pentenyl)-cyclopent-3-ene |
| 59 | 10 | 1-hydroxy-2-(7-carboxy-2-cis-heptenyl)-cyclopent-3-ene |
| 60 | 11 | 1-hydroxy-2-(8-carboxy-2-cis-octenyl)-cyclopent-3-ene |
| 61 | 12 | 1-hydroxy-2-(6-carboxy-4-methyl-2-cis-hexenyl)cyclopent-3-ene |
| 62 | 13 | 1-hydroxy-2-(6-carboxy-4(R)-methyl-2-cis-hexenyl)cyclopent-3-ene |
| 63 | 14 | 1-hydroxy-2-(6-carboxy-4-ethyl-2-cis-hexenyl)cyclopent-3-ene |
| 64 | 15 | 1-hydroxy-2-(6-carboxy-4-propyl-2-cis-hexenyl)cyclopent-3-ene |

EXAMPLES 65-71

Oxidation of the 1-hydroxycyclopent-3-enes listed in Table 8 below by the procedure described in Example 56 is productive of the product cyclopent-3-en-1-ones of the table.

TABLE 8

| Example | Starting 1-hydroxycyclopent-3-ene of Example | Product 2-(ω-carboxy-2-cis-alkenyl)cyclopent-3-en-1-one |
|---|---|---|
| 65 | 58 | 2-(5-carboxy-2-cis-pentenyl)cyclopent-3-en-1-one |
| 66 | 59 | 2-(7-carboxy-2-cis-heptenyl)cyclopent-3-en-1-one |
| 67 | 60 | 2-(8-carboxy-2-cis-octenyl)cyclopent-3-en-1-one |
| 68 | 61 | 2-(6-carboxy-4-methyl-2-cis-hexenyl)cyclopent-3-en-1-one |
| 69 | 62 | 2-(6-carboxy-4(R)-methyl-2-cis-hexenyl)cyclopent-3-en-1-one |
| 70 | 63 | 2-(6-carboxy-4-ethyl-2-cis-hexenyl)cyclopent-3-en-1-one |
| 71 | 64 | 2-(6-carboxy-4-propyl-2-cis-hexenyl)cyclopent-3-en-1-one |

EXAMPLES 72-78

Base treatment according to the procedure described in Example 57 of the cyclopent-3-ene-1-ones listed in Table 9 below is productive of the product cyclopent-2-en-1-ones of the table.

TABLE 9

| Example | Starting 2-(ω-carboxy-2-cis-alkenyl)cyclopent-3-ene-1-one of Example | Product 2-(ω-carboxy-2-cis-alkenyl)cyclopent-2-en-1-one |
|---|---|---|
| 72 | 65 | 2-(5-carboxy-2-cis-pentenyl)cyclopent-2-en-1-one |
| 73 | 66 | 2-(7-carboxy-2-cis-heptenyl)cyclopent-2-en-1-one |
| 74 | 67 | 2-(8-carboxy-2-cis-octenyl)cyclopent-2-en-1-one |
| 75 | 68 | 2-(6-carboxy-4-methyl-2-cis-hexenyl)cyclopent-2-en-1-one |
| 76 | 69 | 2-(6-carboxy-4(R)-methyl-2-cis-hexenyl)cyclopent-2-en-1-one |
| 77 | 70 | 2-(6-carboxy-4-ethyl-2-cis-hexenyl)cyclopent-2-en-1-one |
| 78 | 71 | 2-(6-carboxy-4-propyl-2-cis-hexenyl)cyclopent-2-en-1-one |

EXAMPLES 79-86

Treatment of the listed 2-(ω-carboxy-2-cis-alkenyl)-cyclopent-2-en-1-one of Table 10 below with diazomethane in the usual manner (see procedure for Examples 560–586) is productive of the product methyl esters of the table.

TABLE 10

| Example | Starting carboxylic acid of Example | Product 2-(ω)-carbomethoxy-2-cis-alkenyl)cyclopent-2-en-1-one |
|---|---|---|
| 79 | 72 | 2-(5-carbomethoxy-2-cis-pentenyl)cyclopent-2-en-1-one |
| 80 | 73 | 2-(7-carbomethoxy-2-cis-heptenyl)cyclopent-2-en-1-one |
| 81 | 74 | 2-(8-carbomethoxy-2-cis-octenyl)cyclopent-2-en-1-one |
| 82 | 57 | 2-(6-carbomethoxy-2-cis-hexenyl)cyclopent-2-en-1-one |
| 83 | 75 | 2-(6-carbomethoxy-4-methyl-2-cis-hexenyl)-cyclopent-2-en-1-one |
| 84 | 76 | 2-(6-carbomethoxy-4(R)-methyl-2-cis-hexenyl)-cyclopent-2-en-1-one |
| 85 | 77 | 2-(6-carbomethoxy-4-ethyl-2-cis-hexenyl)-cyclopent-2-en-1-one |
| 86 | 78 | 2-(6-carbomethoxy-4-propyl-2-cis-hexenyl)-cyclopent-2-en-1-one |

EXAMPLE 87

Preparation of 1-octyn-4-ol

A suspension of 24.3 g. (1.0 mole) of magnesium in 90 ml. of dry ether is stirred at room temperature under nitrogen with 100 mg. of mercuric chloride. The reaction is initiated by the addition of 2 ml. of propargyl bromide and maintained by the dropwise addition of a solution of 119.5 g. (1.0 mole) of propargyl bromide and 107.7 g. (1.25 mole) of valenaldehyde in 300 ml. of dry ether. While the initial reaction is quite vigorous and is maintained at 30° only by cooling in an ice bath it may become necessary to heat the mixture to reflux temperature after about a third of the ether solution is added in order to maintain the reaction. After the addition is complete the reaction mixture is refluxed until most of the magnesium is dissolved (several hours) and the reaction mixture is decanted from excess magnesium into 1500 ml. of stirred ice-cold ammonium chloride solution. The ether layer is separated and the aqueous layer is extracted three times with 300 ml. portions of ether. The combined ether extract is washed with saturated sodium chloride solution, dried over magnesium sulfate and filtered. Evaporation of the ether under vacuum leaves about 115 g. of yellow oil, which is distilled through a 15 cm. Vigreaux column at 18 mm. The fraction boiling at 81°-82° is collected (36 g.) and the higher-boiling and lower-boiling distillates may be redistilled to yield additional product. The infrared absorption spectrum shows at most a trace of allene (5.1 $\mu$) and gas-liquid partition chromatography shows a purity of about 98% for the main fraction.

EXAMPLES 88-91

The product 1-alkyn-4-ols of Table 11 below are prepared by treatment of the aldehydes listed in Table 11 with propargyl magnesium bromide by the procedure described above in Example 87.

TABLE 11

| Example | Starting aldehyde | Product 1-alkyn-4-ol |
|---|---|---|
| 88 | n-hexaldehyde | 1-nonyn-4-ol |
| 89 | n-heptaldehyde | 1-decyn-4-ol |
| 90 | n-butyraldehyde | 1-heptyn-4-ol |
| 91 | 3-cis-hexenaldehyde* | 4-hydroxy-6-cis-ene-1-nonyne |

*M. Winter, Helv. Chim. Acta, 46, 1792 (1963).

EXAMPLE 92

Preparation of 1-Triphenylmethoxy-5-hexyne

A stirred mixture of 9.81 g. (0.10 moles) of 5-hexyn-1-ol, 33.5 g. (0.12 moles) of triphenylmethyl chloride, and 200 ml. of dry pyridine is refluxed for 60 minutes. The cooled mixture is poured into water and extracted with ether. The extract is washed successively with water, ice-cold N-hydrochloric acid, water, saturated sodium bicarbonate solution, and saturated sodium chloride solution. The extract is dried with magnesium sulfate. The crude product obtained after evaporation of the solvent is purified by chromatography on Florisil to give an oil, $\lambda$ max. 3290 (acetylenic hydrogen), 1600, 1072, and 705 cm$^{-1}$ (triphenylmethoxy group).

EXAMPLE 93

Preparation of 4-Triphenylmethoxy-1-Octyne

A mixture of 10 g. (0.08 moles) of 4-hydroxy-1-octyne [L. Crombie and A. G. Jacklin, J. Chem. Soc., 1632 (1937), also Example 87] and 30.75 g. (0.09 moles) of triphenylmethyl bromide in 85 ml. of dry pyridine is heated on the steam bath for 2 hours. The cooled mixture is treated with water and extracted with ether. The extract is washed successively with ice cold 2% hydrochloric acid, saturated sodium chloride solution, dried with magnesium sulfate, and taken to dryness. Column chromatography of the residue on Florisil affords an oil; $\lambda$max 3.01, 4.72 (acetylenic hydrogen), 6.28, 9.65 and 14.25 $\mu$ (triphenylmethoxy group).

EXAMPLE 94

Preparation of 4-Triphenylmethoxy-1-hexyne

A stirred solution of 9.81 g. (0.10 moles) of 4-hydroxy-1-hexyne and 33.5 g. (0.12 moles) of triphenylmethyl chloride in 100 ml. of dry pyridine is heated at reflux for 2 hours. The cooled mixture is treated with water and extracted with a hexane-ether mixture. The extract is washed successsively with water and saturated sodium chloride solution, dried over magnesium sulfate, and concentrated. Column chromatography of the residue on Florisil gives an oil, $\lambda$ mas. 3290 (acetylene hydrogen), 1600, 1030 and 705 cm$^{-1}$ (triphenylmethoxy group).

EXAMPLES 95-112

The triphenylmethoxy substituted 1-alkynes listed in the table below are prepared by the method of Example 93 from triphenylmethyl bromide and the corresponding hydroxy substituted 1-alkynes, appropriate literature references to which are provided in the table.

TABLE 12

| Example | Reference to starting hydroxy substituted 1-alkyne | Product triphenylmethoxy substituted 1-alkyne |
|---|---|---|
| 95 | Reference 1 | 4-triphenylmethoxy-1-pentyne |
| 96 | Reference 1 (Example 90) | 4-triphenylmethoxy-1-heptyne |
| 97 | Reference 1 | 4-triphenylmethoxy-5-methyl-1-hexyne |
| 98 | Reference 2 (Example 88) | 4-triphenylmethoxy-1-nonyne |
| 99 | Reference 3 (Example 89) | 4-triphenylmethoxy-1-decyne |
| 100 | Reference 4 | 5-triphenylmethoxy-1-pentyne |
| 101 | Reference 5 | 7-triphenylmethoxy-1-heptyne |
| 102 | Reference 6 | 9-triphenylmethoxy-1-nonyne |
| 103 | Reference 7 | 10-triphenylmethoxy-1-decyne |
| 104 | Reference 8 | 11-triphenylmethoxy-1-undecyne |
| 105 | Reference 9 | 5-triphenylmethoxy-1-hexyne |
| 106 | Reference 10 | 4-triphenylmethoxy-7-methyl-1-octyne |
| 107 | Reference 10 | 4-triphenylmethoxy-5-ethyl-1-heptyne |
| 108 | Reference 11 | 5-triphenylmethoxy-4-methyl-1-pentyne |
| 109 | Reference 11 | 5-triphenylmethoxy-4-ethyl-1-pentyne |
| 110 | Reference 11 | 5-triphenylmethoxy-4-methyl-1-hexyne |
| 111 | Reference 11 | 5-triphenylmethoxy-4-ethyl-1-hexyne |
| 112 | Example 91 | 4-triphenylmethoxy-6-cis-ene-1- |

TABLE 12-continued

| Example | Reference to starting hydroxy substituted 1-alkyne | Product triphenylmethoxy substituted 1-alkyne |
|---|---|---|
| | | nonyne |

References:
1. G. Fontaine et al., Bull. Soc. Chem. France, 1447 (1963).
2. S. Abe and K. Sato, Bull. Soc. Chem. Japan, 29, 88 (1956): Chem. Abstr., 50, 13737 (1956).
3. L. Crambie and A.G. Jacklin, J. Chem. Soc., 1622 (1957); 1740 (1955).
4. R. Paul and S. Tehelitcheff, Compt. rend., 232, 2230 (1951).
5. C. Crisan, Ann. Chim. (Paris), [13]1, 436 (1956).
6. R. Riemschneider, G. Kasang, and C. Boehme, Montashefte Chem., 96, 1766 (1965).
7. Ames, J. Chem. Soc. (C), 1556 (1967).
8. L.D. Bergel'son et al., Zh. Obschei Khim., 32, 58 (1962): Chem. Abstr., 57, 14930a (1962).
9. N.V. Egorov and A.S. Atavin, Chem. Abstr., 71, 61473u (1969).
10. Nobuharra Akio, Agr. Biol. Chem. (Tokyo), 32, 1016 (1968): Chem. Abstr., 70, 3219j (1969).
11. J. Colonge and R. Gelin, Bull. Soc. Chem., France, 799 (1954).

EXAMPLE 113

Preparation of 8-triphenylmethoxy-1-octyne

To a stirred suspension of f68.1 g. (0.18 moles) of 1-chloro-6-triphenylmethoxyhexane, prepared from 1-chloro-6-hydroxyhexane and triphenylmethyl chloride in the manner of Example 92, in 60 ml. of dimethylsulfoxide is added a solution of 19.9 g (0.216 moles) of lithium acetylideethylenediamine complex in 120 ml. of dimethylsulfoxide during 20 minutes. The temperature is maintained at 25° C. with an ice bath during the addition, after which the mixture is stirred at ambient temperature for 3.5 hours and then at 30° C. for 15 minutes. The mixture is diluted with 100 ml. of ether and treated dropwise with 150 ml. of water and ice bath cooling. The mixture is diluted with 400 ml. of water and 250 ml. of 2:1 ether-pet ether and acidified with 120 ml. of 4N hydrochloric acid in the ice bath. The phases are separated, and the aqueous phase is extracted with 3:1 ether-pet ether. The combined extracts are washed successively with water and saturated sodium chloride solution, dried over magnesium sulfate, and concentrated. Column chromatography of the residue on Florisil ® affords the subject compound as white crystals, m.p. 43°–45° C. after recrystallization from pet-ether, λ max 3300 (acetylenic hydrogen), 2360 (triple bond), 1600, 1068, and 706 cm$^{-1}$ (triphenylmethoxy group).

EXAMPLE 114

Preparation of 3-bromo-1-octyne

To a stirred suspension of 600 g. of triphenylphosphine in 2000 ml. of acetonitrile, under nitrogen atmosphere, is added dropwise 118 ml. of bromine at a temperature not exceeding 35° C. After stirring for an additional hour, the supernatant liquid is decanted and taken to dryness. The solid residue is combined with the previous solid with 1500 ml. of dimethylformamide. The suspension is stirred at −20° C. and a solution of 200 g. of 1-octyn-3-ol in 300 ml. of dimethylformamide is added in three portions. The temperature is allowed to warm up slowly to 20° C. After three hours the solution is extracted with three 1600 ml. portion of petroleum ether (b.p. 30°–60°). The combined extracts are washed with saturated sodium chloride solution, saturated sodium bicarbonate solution, and finally with saturated sodium chloride solution, dried with anhydrous magnesium sulfate and take to dryness (bath 30°–35° C.). The residual oil was distilled to give 117 g. (39%) of product, b.p. 66°–68°/9mm.

EXAMPLE 115

Preparation of 3-hydroxymethyl-1-octyne

To a suspension of 2.54 g. of magnesium in 15 ml. of ether containing a few crystals of mercuric chloride, under nitrogen atmosphere, is added a small portion of 3-bromo-1-octyne in 20 ml. of ether. When reaction has set in, the flask is cooled in a 15° C. water bath, and the remainder of the halide in ether is added dropwise over a period of about 1 hour. When all of the halide has been added, stirring is continued for 15 minutes. The flask is then fitted with a glass tube which reaches almost to, but not below, the surface of the liquid. This tube connects directly with a round bottom flask containing about 20 g. of paragormaldehyde which has been previously dried for two days in a vacuum desicator over phosphorous pentoxide. This flask contains an inlet tube for nitrogen. The reaction flask is immersed in an ice-bath, and the flask containing the paraformaldehyde is heated in an oil bath at 180°–200° C. The formaldehyde formed by depolymerization is carried over into the Grignard reagent by a slow current of dry nitrogen. At the end of 30–40 minutes formaldehyde addition is terminated and the reaction mixture stirred at room temperature for 18 hours.

The reaction mixture is then cooled in an icebath and saturated ammonium chloride is added, followed by water and then ether. The mixture is then acidified with 2M sulfuric acid. The organic phase is separated, washed with saturated sodium chloride solution, dried with anhydrous magnesium sulfate and the solvent removed in vacuo. The residue is distilled to give 4.4 g of product; b.p. 91°–93°/9mm.

EXAMPLES 116–118

Treatment of the 3-hydroxymethyl-1-alkynes, listed in Table 13 below, with triphenylmethyl bromide by the procedure described in Example 93 is productive of the 3-triphenylmethoxymethyl-1-alkynes of the Table.

TABLE 13

| Example | Starting 3-hydroxymethyl-1-alkyne | Product 3-triphenylmethoxymethyl-1-alkyne |
|---|---|---|
| 116 | 3-hydroxymethyl-1-hexyne[1] | 3-triphenylmethoxymethyl-1-hexyne |
| 117 | 3-hydroxymethyl-1-heptyne[1] | 3-triphenylmethoxymethyl-1-heptyne |
| 118 | 3-hydroxymethyl-1-octyne[1] (Ex. 115) | 3-triphenylmethoxymethyl-1-octyne |

[1]A. Schaap, L. Brandsma and J.F. Arens, Rec. trav. chim., 86, 393 (1967)

EXAMPLE 119

Preparation of 1-chloro-3-triphenylmethoxyhexane

A stirred solution of 27.3 g. (0.20 moles) of 1-chloro-3-hexanol, 77.6 g (0.24 moles) of triphenylmethyl bromide, 30.0 g. (0.28 moles of 2,6-lutidine, and 200 ml. of chlorobenzene is heated at 95° C. for 1 hours. The cooled mixture is treated with water, and the organic phase is washed successively with water and saturated sodium chloride solution. The solution is dried over magnesium sulfate and concentrated. Column chromatography of the residue on Florisil affords the subject compound as an oil, λ max. 1600, 1030, and 705 cm$^{-1}$ (triphenylmethoxy group).

EXAMPLE 120

Preparation of 5-triphenylmethoxy-1-octyne

To a stirred solution of 32.2 g. (85 moles) of 1-chloro-3-triphenylmethoxyhexane (Example 119) in 25 ml. of dimethylsulfoxide (DMSO) is added a solution of 9.4 g. (102 mmoles) of lithium acetylide-ethylene diamine complex in 60 ml. of DMSO during 10 minutes while maintaining a temperature of 25°–30° C. After 3.5 hours the mixture is diluted with ether and treated successively with water and 4N hydrochloric acid while cooling in an ice bath. The phases are separated, and the aqueous phase is extracted with ether-petroleum ether. The combined extracts are washed successively with water and saturated sodium chloride solution, dried over magnesium sulfate, and concentrated. The product is then purified by column chromatography of the residue on Florisil.

EXAMPLE 121

Preparation of cis-5-octen-1-yne

A 57% sodium hydride dispersion (9.66 g., 0.23 mole) is washed free of mineral oil in a nitrogen atmosphere with hexane. The hydride is heated at 75° C. with 220 ml. of dimethylsulfoxide for 45 minutes. The resulting green solution is cooled to 18° C. and treated with a solution of 4-pentynyl-triphenylphosphonium iodide (100 g., 0.22 mole) in 220 ml. of dimethylsulfoxide over a 25 minute period. The resulting red solution is stirred at ambient temperature for f45 minutes. To the solution is added a solution of freshly distilled propionaldehyde (14.0 g., 0.24 mole) in 10 ml. of dimethylsulfoxide over a 10 minute period at 25° C. After standing at room temperature, the reaction is quenched with half-saturated brine and brought to pH 4 with 4N HCl. The product is extracted with an ether-hexane mixture, and the extract is washed successively with water and brine, dried over MgSO$_4$, and concentrated. The crude product is fractionated with a spinning band column to give a colorless distillate, b.p. 121°–122° C., IR 3270, 2110 and 1645 cm$^{-1}$.

EXAMPLE 122

Preparation of 8-chloro-1-octyne

The subject compound is prepared by the method of W. J. Gensler and G. R. Thomas, J.A.C.S. 73, 4601 (1951).

EXAMPLE 123

Preparation of 1-iodo-4-triphenylmethoxy-trans-1-octene

To a stirred suspension of 1.78 g. (0.074 mole) of sodium borohydride in 200 ml. of dry glyme at −5° C. under nitrogen is added 15.8 g. (0.22 mole) of 2-methyl-2-butene and 16.2 g. (0.11 mole) of boron trifluoride etherate, and the mixture is stirred for 2 hours at −5°to 0° C. A solution of 37.5 g. (0.10 mole) of 4-trityloxy-1-octyne (Example 93) in 50 ml. of glyme is added to the cold solution during 5–10 minutes, and the solution is allowed to warm to 20° during 1.5 hours. The reaction mixture is cooled to 0° C., and 30 g. (0.4 mole) of dry trimethylamine-N-oxide is added during 5 minutes. On removing the cooling bath the temperature rises to 40° C., and the mixuture is kept between 30°–40° for 1.5 hours. The suspension is poured rapidly into 1 liter of ice cold 15% sodium hydroxide solution during good stirring and a solution of 80 g. of iodine in 200 ml. of tetrahydrofuran is added immediately. Stirring is continued for 30 minutes without further cooling and the organic layer is separated. The aqueous layer is extracted with three 200 ml. portions of ether and the combined organic layers are washed successively with water, 5% sodium thiosulfate solution and saturated sodium chloride, dried over magnesium sulfate, filtered and evaporated to yield 50 g. of yellow oil. The bulk of the oil is dissolved in hexane and, after decantantation from a gummy solid the hexane solution is percolated through a 5.1 cm diameter column of 1500 g. of alumina with additional hexane. Fractions containing the desired product are concentrated to a pale yellow oil (33 g.) which has n.m.r. and infrared spectra characteristics of the desired product.

EXAMPLES 124–148

Treatment of the triphenylmethoxy substituted 1-alkynes listed in Table 14 below with disiamylborane, prepared in situ from 2-methyl-2-butene, boron trifluoride and sodium borohydride, followed by trimethylamine N-oxide, and then sodium hydroxide and iodine - all by the procedure described in Example 123 above furnishes the product triphenylmethoxy substituted 1-iodo-1-trans-alkenes of the table.

TABLE 14

| Example | Starting triphenylmethoxy substituted 1-alkyne of Example | Product 1-iodo-triphenylmethoxysubstituted-1-trans-alkene |
|---|---|---|
| 124 | 92 | 1-iodo-6-triphenylmethoxy-1-trans-hexene |
| 125 | 94 | 1-iodo-4-triphenylmethoxy-2-trans-hexene |
| 126 | 95 | 1-iodo-4-triphenylmethoxy-1-trans-pentene |
| 127 | 96 | 1-iodo-4-triphenylmethoxy-1-trans-heptene |
| 128 | 97 | 1-iodo-4-triphenylmethoxy-5-methyl-1-trans-hexene |
| 129 | 98 | 1-iodo-4-triphenylmethoxy-1-trans-nonene |
| 130 | 99 | 1-iodo-4-triphenylmethoxy-1-trans-decene |
| 131 | 100 | 1-iodo-5-triphenylmethoxy-1-trans-pentene |
| 132 | 101 | 1-iodo-7-triphenylmethoxy-1-trans-heptene |
| 133 | 102 | 1-iodo-9-triphenylmethoxy-1-trans-nonene |
| 134 | 103 | 1-iodo-10-triphenylmethoxy-1-trans-decene |
| 135 | 104 | 1-iodo-11-triphenylmethoxy-1-trans-undecene |
| 136 | 105 | 1-iodo-5-triphenylmethoxy-1-trans-hexene |
| 137 | 106 | 1-iodo-4-triphenylmethoxy-7-methyl-1-trans-octene |
| 138 | 107 | 1-iodo-4-triphenylmethoxy-5-ethyl-1-trans-heptene |
| 139 | 108 | 1-iodo-5-triphenylmethoxy-4-methyl-1-trans-pentene |
| 140 | 109 | 1-iodo-5-triphenylmethoxy-4-ethyl-1-trans-pentene |
| 141 | 110 | 1-iodo-5-triphenylmethoxy-4-methyl-1-trans-hexene |

TABLE 14-continued

| Example | Starting triphenyl-methoxy substituted 1-alkyne of Example | Product 1-iodo-triphenylmethoxysubstituted-1-trans-alkene |
| --- | --- | --- |
| 142 | 111 | 1-iodo-5-triphenyl-methoxy-4-ethyl-1-trans-hexene |
| 143 | 112 | 1-iodo-4-triphenyl-methoxy-1-trans,6-cis-nonadiene |
| 144 | 113 | 1-iodo-8-triphenyl-methoxy-1-trans-octene |
| 145 | 116 | 1-iodo-3-triphenyl-methoxymethyl-1-trans-hexene |
| 146 | 117 | 1-iodo-3-triphenyl-methoxymethyl-1-trans-heptene |
| 147 | 118 | 1-iodo-3-triphenyl-methoxymethyl-1-trans-octene |
| 148 | 120 | 1-iodo-5-triphenyl-methoxy-1-trans-octene |

EXAMPLE 149

Preparation of 9-oxo-11a,16-dihydroxy-5-cis; 13-trans-prosta-dienoic acid

To a stirred solution of 26.8 g. (51 mmoles) of 1-iodo-4-triphenylmethoxy-trans-1-octene (Example 123) in 50 ml. of toluene is added 26.3 ml. of 1.9 M n-butyllithium in hexane at −70°. After the addition the solution is stirred for 60 minutes at −40°. This solution containing 4-triphenylmethoxy-trans-1-octenyl lithium is treated with 26.8 ml. of 1.45 M trimethylaluminum in hexane at −40°, and the resulting solution is stirred at 0° for 20 minutes.

To the above solution containing lithio trimethyl-(4-triphenylmethoxy-trans-1-octenyl)alanate is added a solution of 16.7 g. (42.5 mmoles) of 4-tetrahydropyranyloxy-2-(6-carbotetrahydropyranyloxy-2-cis-hexenyl)cyclopent-2-en-1-one (Example 37) in 60 ml. of ether at 0°–8°. The mixture is stirred at 0° for 1 hour and 25° for 20 hours, diluted with ether, and poured into a stirred mixture of ice and 20 ml. of 37% hydrochloric acid. The aqueous phase is separated and extracted with ether. The combined organic phases are washed successively with water and brine, dried over magnesium sulfate, and concentrated to give an oil.

The crude product is dissolved in 425 ml. of 4:2:1 acetic acid-tetrahydrofuran-water, and the resulting solution is heated at 45° for 4 hours. The solvents are removed in vacuo at 20° to give a mixture of oil and crystals.

The crude product is purified by partition chromatography on acid-washed silica gel using the conjugate phases from benzene-methanol-water (15:5:2). The prostadienoic acid is thereby obtained as an oil, $\nu$ max. (film) 330 (hydroxy), 1735 (cyclopentanone), 1705 (carboxylic acid), and 967 cm$^{-1}$ (trans-olefin).

EXAMPLES 150–203H

The product 9-oxo-11α-hydroxy-5-cis,13-trans-prostadienoic acids of Table 15 below are obtained by the procedure described in Example 149. In accordance with the process described therein, the starting triphenylmethoxy substituted 1-iodo-trans-1-alkenes listed in Table 15 are treated with butyl lithium providing the corresponding triphenylmethoxy substituted trans-1-alkenyl lithium derivative which on treatmeant with trimethylaluminum furnish the corresponding lithio trimethyl (triphenylmethoxy substituted trans-1-alkenyl)alanates, which in turn are treated with the 4-oxycyclopent-2-en-1-ones listed in the table. The resulting triphenylmethoxy substituted 9-oxo-11α-tetrahydropyranyloxy(or 11α-trialkylsilyloxy)-5-cis,13-trans-prostadienoic acid tetrahydropyranyl (or trialkylsilyl) ester is hydrolyzed to the listed products by treatment with acetic acid:tetrahydrofuran:water.

TABLE 15

| Example | Starting 4-oxy-cyclo-pent-2-en-1-one of Example | Starting triphenyl-methoxy-1-iodo-trans-1-alkene of Example | Product 9-oxo-11α-hydroxy-5-cis,13-trans-prostadienoic acid |
| --- | --- | --- | --- |
| 150 | 37 | 129 | 9-oxo-11α,16-dihydroxy-20-methyl-5-cis,13-trans-prostadienoic acid |
| 151 | 37 | 130 | 9-oxo-11α,16-dihydroxy-20-ethyl-5-cis,13-trans-prostadienoic acid |
| 152 | 37 | 127 | 9-oxo-11α,16-dihydroxy-20-nor-5-cis,13-trans-prostadienoic acid |
| 153 | 37 | 125 | 9-oxo-11α,16-dihydroxy-19,20-dinor-5-cis,13-trans-prostadienoic acid |
| 154 | 37 | 137 | 9-oxo-11α,16-dihydroxy-19-methyl-5-cis,13-trans-prostadienoic acid |
| 155 | 45 | 138 | 9-oxo-11α,16-dihydroxy-17-ethyl-20-nor-5-cis,13-trans-prostadienoic acid |
| 156 | 37 | 143 | 9-oxo-11α,16-dihydroxy-20-methyl-5-cis,13-trans,18-cis-prostadienoic acid |
| 157 | 37 | 126 | 9-oxo-11α,16-dihydroxy-18,19,20-trinor-5-cis,13-trans-prostadienoic acid |
| 158 | 37 | 147 | 9-oxo-11-60-hydroxy-15-hydroxymethyl-5-cis,13-trans-prostadienoic acid |
| 159 | 37 | 146 | 9-oxo-11α-hydroxy-15-hydroxymethyl-20-nor-5-cis,13-trans-prostadienoic acid |
| 160 | 37 | 148 | 9-oxo-11α,17-dihydroxy-5-cis,13-trans-prostadienoic acid |
| 161 | 45 | 124 | 9-oxo-11α,18-dihydroxy-19,20-dinor-5-cis,13-trans-prostadienoic acid |
| 162 | 37 | 132 | 9-oxo-11α,19-dihydroxy-20-nor-5-cis,13-trans-prostadienoic acid |
| 163 | 37 | 144 | 9-oxo-11α,20-dihydroxy-5-cis,13-trans-prostadienoic acid |
| 164 | 37 | 133 | 9-oxo-11α-hydroxy-20-hydroxymethyl-5-cis,13-trans-prostadienoic acid |
| 165 | 49 | 141 | 9-oxo-11α,17-dihydroxy-16-methyl-19,20-dinor-5-cis,13-trans-prostadienoic acid |
| 166 | 41 | 123 | 9-oxo-11α,16-dihydroxy-4-methyl-5-cis,13-trans-prostadienoic acid |
| 167 | 41 | 129 | 9-oxo-11α,16-dihydroxy-4,20-dimethyl-5-cis,13-trans-prostadienoic acid |

TABLE 15-continued

| Example | Starting 4-oxy-cyclo-pent-2-en-1-one of Example | Starting triphenyl-methoxy-1-iodo-trans-1-alkene of Example | Product 9-oxo-11α-hydroxy-5-cis,13-trans-prostadienoic acid |
|---|---|---|---|
| 168 | 50 | 140 | 9-oxo-11α,17-dihydroxy-4-methyl-16-ethyl-18,19,20-trinor-5-cis,13-trans-prostadienoic acid |
| 169 | 41 | 143 | 9-oxo-11α,16-dihydroxy-4,20-dimethyl-5-cis,13-trans,18-cis-prostatrienoic acid |
| 170 | 41 | 147 | 9-oxo-11α-hydroxy-15-hydroxymethyl-4-methyl-5-cis,13-trans-prostadienoic acid |
| 171 | 42 | 147 | 9-oxo-11α-hydroxy-15-hydroxymethyl-4(R)methyl-5-cis,13-trans-prostadienoic acid |
| 172 | 42 | 123 | 9-oxo-11α,16-dihydroxy-4(R)-methyl-5-cis,13-trans-prostadienoic acid |
| 173 | 42 | 130 | 9-oxo-11α,16-hydroxy-4(R)-methyl-20-ethyl-5-cis,13-trans-prostadienoic acid |
| 174 | 51 | 144 | 9-oxo-11α20,-dihydroxy-(R)-methyl-5-cis,13-trans-prostadienoic acid |
| 175 | 42 | 136 | 9-oxo-11α,17-dihydroxy-4(R)-methyl-19,20-dinor-5-cis,13-trans-prostasdienoic acid |
| 176 | 42 | 143 | 9-oxo-11α,16-dihydroxy-4(R),20-dimethyl-5-cis,13-trans,18-cis-prostatrienoic acid |
| 177 | 52 | 123 | 9-oxo-11α,16-dihydroxy-4-ethyl-5-cis,13-trans-prostadienoic acid |
| 178 | 43 | 128 | 9-oxo-11α,16-dihydroxy-4-ethyl-17-methyl-19,20-dinor-5-cis,13-trans-prostadienoic acid |
| 179 | 52 | 134 | 9-oxo-11α-hydroxy-4-ethyl-20-(β-hydroxyethyl)-5-cis,13-trans-prostadienoic acid |
| 180 | 43 | 147 | 9-oxo-11α-hydroxy-4-ethyl-15-hydroxymethyl-5-cis,13-trans-prostadienoic acid |
| 181 | 43 | 143 | 9-oxo-11α,16-dihydroxy-4-ethyl-20-methyl-5-cis,13-trans,18-cis-prostatrienoic acid |
| 182 | 44 | 123 | 9-oxo-11α,16-dihydroxy-4-propyl-5-cis,13-trans-prostadienoic acid |
| 183 | 53 | 142 | 9-oxo-11α,17-dihydroxy-4-propyl-16-ethyl-19,20-dinor-5-cis,13-trans-prostadienoic acid |
| 184 | 44 | 137 | 9-oxo-11α,16-dihydroxy-4-propyl-19-methyl-5-cis,13-trans-prostadienoic acid |
| 185 | 44 | 144 | 9-oxo-11α,20-dihydroxy-4-propyl-5-cis,13-trans-prostadienoic acid |
| 186 | 44 | 147 | 9-oxo-11α-hydroxy-15-hydroxymethyl-4-propyl-5-cis,13-trans-prostadienoic acid |
| 187 | 44 | 145 | 9-oxo-11α-hydroxy-15-hydroxymethyl-4-propyl-19,20-dinor-5-cis,13-trans-prostadienoic acid |
| 188 | 44 | 143 | 9-oxo-11α,16-dihydroxy-4-propyl-20-methyl-5-cis,13-trans,18-cis-prostatrienoic acid |
| 189 | 44 | 148 | 9-oxo-11α,17-dihydroxy-4-propyl-5-cis,13-trans-prostadienoic acid |
| 190 | 38 | 123 | 9-oxo-11α,16-dihydroxy-4-nor-5-cis,13-trans-prostadienoic acid |
| 191 | 38 | 127 | 9-oxo-11α,16-dihydroxy-4,20-dinor-5-cis,13-trans-prostadienoic acid |
| 192 | 46 | 141 | 9-oxo-11α,17-dihydroxy-4,19,20-trinor-16-methyl-5-cis,13-trans-prostadienoic acid |
| 193 | 38 | 132 | 9-oxo-11α,19-dihydroxy-4,20-dinor-5-cis,13-trans-prostadienoic acid |
| 194 | 38 | 147 | 9-oxo-11α-hydroxy-15-hydroxymethyl-4-nor-5-cis,13-trans-prostadienoic acid |
| 195 | 38 | 146 | 9-oxo-11α-hydroxy-15-hydroxymethyl-4,20-dinor-5-cis,13-trans-prostadienoic acid |
| 196 | 39 | 123 | 9-oxo-11α,16-dihydroxy-4a-homo-5-cis,13-trans-prostadienoic acid |
| 197 | 39 | 129 | 9-oxo-11α,16-dihydroxy-4a-homo-20-methyl-5-cis,13-trans-prostadienoic acid |
| 198 | 47 | 139 | 9-oxo-11α,17-dihydroxy-4a-homo-16-methyl-18,19,20-trinor-5-cis,13-trans-prostadienoic acid |
| 199 | 39 | 147 | 9-oxo-11α-hydroxy-4a-homo-15-hydroxymethyl-5-cis,13-trans-prostadienoic acid |
| 200 | 47 | 145 | 9-oxo-11α-hydroxy-4a-homo-15-hydroxymethyl-19,20-dinor-5-cis,13-trans-prostadienoic acid |
| 201 | 39 | 143 | 9-oxo-11α,16-dihydroxy-4a-homo-20-methyl-5-cis,13-trans,18-cis-prostatrienoic acid |
| 202 | 39 | 132 | 9-oxo-11α,19-dihydroxy-4a-homo-20-nor-5-cis,13-trans-prostadienoic acid |
| 203 | 40 | 123 | 9-oxo-11α,16-dihydroxy-4a,4b-bishomo-5-cis,13-trans-prostadienoic acid |
| 203A | 40 | 148 | 9-oxo-11α,17-dihydroxy-4a,4b-bishomo-5-cis,13-trans-prostadienoic acid |
| 203B | 40 | 130 | 9-oxo-11α,16-dihydroxy-4a,4b-bishomo-20-ethyl-5-cis,13-trans-prostadienoic acid |
| 203C | 40 | 131 | 9-oxo-11α,17-dihydroxy-4a,4b-bishomo-18,19,20-trinor-5-cis,13-trans-prostadienoic acid |
| 203D | 48 | 137 | 9-oxo-11α,16-dihydroxy-4a,4b-bishomo-19-methyl-5-cis,13-trans-prostadienoic acid |
| 203E | 48 | 135 | 9-oxo-11α-hydroxy-4a,4b-bishomo-20-(γ-hydroxypropyl)-5-cis,13-trans-prostadienoic acid |
| 203F | 40 | 143 | 9-oxo-11α,16-dihydroxy-4a,4b-bishomo-20-methyl-5-cis,13-trans,18-cis-prostatrienoic acid |
| 203G | 40 | 147 | 9-oxo-11α-hydroxy-15-hydroxymethyl-4a,4b-bishomo-5-cis,13-trans-prostadienoic acid |

TABLE 15-continued

| Example | Starting 4-oxy-cyclopent-2-en-1-one of Example | Starting triphenyl-methoxy-1-iodo-trans-1-alkene of Example | Product 9-oxo-11α-hydroxy-5-cis,13-trans-prostadienoic acid |
|---|---|---|---|
| 203H | 48 | 146 | 9-oxo-11α-hydroxy-15-hydroxymethyl-4a,4b-bis-homo-20-nor-5-cis,13-trans-prostadienoic acid |

EXAMPLE 204

Preparation of methyl 9-oxo-16-hydroxy-5-cis,13-transprostadienoate

Treatment by the procedure described in Example 149 of 2-(6-carbomethyoxy-2-cis-hexenyl)cyclopent-2-en-1-one (Example 82) with lithio trimethyl(4-triphenylmethoxy-trans-1-octenyl)alanate, prepared from 1-iodo-4-triphenyl-methoxy-trans-1-octene (Example 123) also as described in Example 149, is productive of methyl 9-oxo-16triphenyl-methoxy-5-cis,13-trans-prostadienoate, which on treatment as described in Example 149 with acetic acid-tetrahydrofuran-water provides the subject prostadienoate which is purified by chromatography on silica gel and further purified by liquid-liquid partition chromatography.

EXAMPLE 205

Preparation of 9-oxo-16-hydroxy-5-cis,13-trans-prostadienoic acid

A solution of 2 g. of methyl 9-oxo-16-hydroxy-5-cis,13-trans-prostadienoate (Example 104) in 32 ml. of methanolwater (1:1), containing 850 mg. of potassium hydroxide is stirred at ambient temperature for 18 hours. After acidification with 10% hydrochloric acid, the solution is extracted with ether several times. The combined ether extracts are washed with saturated sodium chloride solution, dried with anhydrous magnesium sulfate and taken to dryness to give an oil which is purified by chromatography on silica gel.

EXAMPLES 206–254

The product 9-oxo-5-cis,13-trans-prostadienoic acids of Table 16 below are prepared by treatment by the procedure described in Example 204 of the cyclopentenone methyl esters listed in Table 16 with the appropriate lithio trimethyl(triphenylmethoxysubstituted-1-trans-alkenyl)alanate prepared by the procedure described in Example 204 from the corresponding 1-iodo-1-trans alkene listed in Table 16 followed by di-O-tritylation of the intermediate triphenylmethoxy substituted methyl 9-oxo-5-cis,13-trans-prostadienoate followed by saponification by the procedure of Example 205 of the resulting hydroxy substituted methyl 9-oxo-5-cis,13-trans-prostadienoate.

TABLE 16

| Example | Starting cyclopentenone methyl ester of Example | Starting triphenylmethoxy substituted 1-iodo-1-trans-alkene of Example | Product 9-oxo-5-cis,13-trans-prostadienoic acid |
|---|---|---|---|
| 206 | 82 | 129 | 9-oxo-16-hydroxy-20-methyl-5-cis,13-trans-prostadienoic acid |
| 207 | 82 | 148 | 9-oxo-17-hydroxy-5-cis,13-trans-prostadienoic acid |
| 208 | 82 | 144 | 9-oxo-20-hydroxy-5-cis,13-trans-prostadienoic acid |
| 209 | 82 | 128 | 9-oxo-16-hydroxy-17-methyl-19,20-dinor-5-cis,13-trans-prostadienoic acid |
| 210 | 82 | 141 | 9-oxo-17-hydroxy-16-methyl-19,20-dinor-5-cis,13-trans-prostadienoic acid |
| 211 | 82 | 147 | 9-oxo-15-hydroxymethyl-5-cis,13-trans-prostadienoic acid |
| 212 | 82 | 146 | 9-oxo-15-hydroxymethyl-20-nor-5-cis,13-trans-prostadienoic acid |
| 213 | 82 | 143 | 9-oxo-16-hydroxy-20-methyl-5-cis,13-trans,18-cis-prostatrienoic acid |
| 214 | 83 | 123 | 9-oxo-16-hydroxy-4-methyl-5-cis,13-trans-prostadienoic acid |
| 215 | 83 | 132 | 9-oxo-19-hydroxy-4-methyl-20-nor-5-cis,13-trans-prostadienoic acid |
| 216 | 83 | 139 | 9-oxo-17-hydroxy-4,16-dimethyl-18,19,20-trinor-5-cis,13-trans-prostadienoic acid |
| 217 | 83 | 147 | 9-oxo-15-hydroxymethyl-4-methyl-5-cis,13-trans-prostadienoic acid |
| 218 | 84 | 123 | 9-oxo-16-hydroxy-4(R)-methyl-5-cis,13-trans-prostadienoic acid |
| 219 | 84 | 137 | 9-oxo-16-hydroxy-4(R),19-dimethyl-5-cis,13-trans-prostadienoic acid |
| 220 | 84 | 138 | 9-oxo-16-hydroxy-4(R)-methyl-17-ethyl-20-nor-5-cis,13-trans-prostadienoic acid |
| 221 | 84 | 129 | 9-oxo-16-hydroxy-4(R),20-dimethyl-5-cis,13-trans-prostadienoic acid |
| 222 | 84 | 147 | 9-oxo-15-hydroxymethyl-4(R)-methyl-5-cis,13-trans-prostadienoic acid |
| 223 | 84 | 143 | 9-oxo-16-hydroxy-4(R),20-dimethyl-5-cis,13-trans,18-cis-prostatrienoic acid |
| 224 | 85 | 143 | 9-oxo-16-hydroxy-4-ethyl-20-methyl-5-cis,13-trans,18-cis-prostatrienoic acid |
| 225 | 85 | 123 | 9-oxo-16-hydroxy-4-ethyl-5-cis,13-trans-prostadienoic acid |
| 226 | 85 | 130 | 9-oxo-16-hydroxy-4-ethyl-20-ethyl-5-cis,13-trans-prostadienoic acid |
| 227 | 85 | 127 | 9-oxo-16-hydroxy-4-ethyl-20-nor-5-cis,13-trans-prostadienoic acid |
| 228 | 85 | 147 | 9-oxo-15-hydroxymethyl-4-ethyl-5-cis,13-trans-prostadienoic acid |
| 229 | 85 | 134 | 9-oxo-20-(β-hydroxyethyl)-4-ethyl-5-cis,13-trans-prostadienoic acid |
| 230 | 85 | 142 | 9-oxo-17-hydroxy-4,16-diethyl-19,20-dinor-5-cis,13- |

TABLE 16-continued

| Example | Starting cyclo-pentenone methyl ester of Example | Starting triphenyl-methoxy substituted 1-iodo-1-trans-al-kene of Example | Product 9-oxo-5-cis,13-trans-prostadienoic acid |
|---|---|---|---|
| | | | trans-prostadienoic acid |
| 231 | 86 | 123 | 9-oxo-16-hydroxy-4-propyl-5-cis,13-trans-prostadienoic acid |
| 232 | 86 | 130 | 9-oxo-16-hydroxy-4-propyl-20-ethyl-5-cis,13-trans-prostadienoic acid |
| 233 | 86 | 125 | 9-oxo-16-hydroxy-4-propyl-19,20-dinor-5-cis,13-trans-prostadienoic acid |
| 234 | 86 | 140 | 9-oxo-17-hydroxy-4-propyl-16-ethyl-18,19,20-tri-nor-5-cis,13-trans-prostadienoic acid |
| 235 | 86 | 147 | 9-oxo-15-hydroxymethyl-4-propyl-5-cis,13-trans-prostadienoic acid |
| 236 | 86 | 143 | 9-oxo-16-hydroxy-4-propyl-20-methyl-5-cis,13-trans,18-cis-prostatrienoic acid |
| 237 | 79 | 143 | 9-oxo-16-hydroxy-4-nor-20-methyl-5-cis,13-trans,18-cis-prostatrienoic acid |
| 238 | 79 | 123 | 9-oxo-16-hydroxy-4-nor-5-cis,13-trans-prostadienoic acid |
| 239 | 79 | 127 | 9-oxo-16-hydroxy-4,20-dinor-5-cis,13-trans-prostadienoic acid |
| 240 | 79 | 136 | 9-oxo-17-hydroxy-4,19,20-trinor-5-cis,13-trans-prostadienoic acid |
| 241 | 79 | 146 | 9-oxo-15-hydroxymethyl-4,20-dinor-5-cis,13-trans-prostadienoic acid |
| 242 | 80 | 123 | 9-oxo-16-hydroxy-4a-homo-5-cis,13-trans-prostadienoic acid |
| 243 | 80 | 129 | 9-oxo-16-hydroxy-20-methyl-4a-homo-5-cis,13-trans-prostadienoic acid |
| 244 | 80 | 126 | 9-oxo-16-hydroxy-4a-homo-18,19,20-trinor-5-cis,13-trans-prostadienoic acid |
| 245 | 80 | 138 | 9-oxo-16-hydroxy-4a-homo-17-ethyl-20-nor-5-cis,13-trans-prostadienoic acid |
| 246 | 80 | 147 | 9-oxo-15-hydroxymethyl-4a-homo-5-cis,13-trans-prostadienoic acid |
| 247 | 80 | 143 | 9-oxo-16-hydroxy-4a-homo-20-methyl-5-cis,13-trans,18-cis-prostatrienoic acid |
| 248 | 81 | 123 | 9-oxo-16-hydroxy-4a,4b-bishomo-5-cis,13-trans-prostadienoic acid |
| 249 | 81 | 130 | 9-oxo-16-hydroxy-4a,4b-bishomo-20-ethyl-5-cis,13-trans-prostadienoic acid |
| 250 | 81 | 148 | 9-oxo-17-hydroxy-4a,4b-bishomo-5-cis,13-trans-prostadienoic acid |
| 251 | 81 | 137 | 9-oxo-16-hydroxy-4a,4b-bishomo-19-methyl-5-cis,13-trans-prostadienoic acid |
| 252 | 81 | 147 | 9-oxo-15-hydroxymethyl-4a,4b-bishomo-5-cis,13-trans-prostadienoic acid |
| 253 | 81 | 124 | 9-oxo-18-hydroxy-4a,4b-bishomo-19,20-dinor-5-cis,13-trans-prostadienoic acid |
| 254 | 81 | 143 | 9-oxo-16-hydroxy-4a,4b-bishomo-20-methyl-5-cis,13-trans,18-cis-prostatrienoic acid |

EXAMPLE 255

Preparation of
9-oxo-11α-hydroxy-5-cis,13-trans-prostadienoic acid

A solution of 7.16 g. (65 mmoles) of 1-octyne in 12 ml. of benzene is treated with 52 ml. of 1.2 M diisobutylaluminum hydride in hexane, and the solution is heated at 50° C. for 2 hours. The solution is cooled to 2° C. and treated during 10 minutes with 28.5 ml. of 2.1 M methyl lithium in ether. The resulting solution is stirred at ambient temperature for 20 minutes, cooled to 5° C., and treated with a solution of 20.1 g. (50 mmoles) of crude 4-tetrahydropyranyloxy-2-(6-carbotetrahydropyranyl-2-cis-hexenyl)cyclopent-2-en-1-one (Example 37) in 30 ml. of ether during 10 minutes. The mixture is then stirred at ambient temperature for 20 hours, diluted to 450 ml. with ether, and poured into a stirred mixture of 400 g. of ice and 90 ml. of 4NHCl. The organic phase is separated, and the aqueous phase is extracted with additional ether. The organic phase is extracted with additional ether. The organic extract is washed successively with ice-cold N/1 hydrochloric acid, water, and saturated sodium chloride solution. The extract is dried over magnesium sulfate and concentrated at reduced pressure to give an oil, max. = 1735 (carbonyl groups), 1035 (tetrahydropyranyloxy groups), and 965 cm$^{-1}$ (trans vinyl group). A solution of this crude oil, crude tetrahydropyran-2-yl 11α-tetrahydropyranyloxy-9-oxo-5-cis,13-trans-prostadienoate in one liter of glacial acid-tetrahydrofuran-water (4:2:1) is stirred at 45° C. for 3.5 hours. The cooled solution is treated with a solution prepared from one liter of water and 500 ml. of saturated sodium chloride solution and extracted with ether. The extract is washed successively with water and saturated sodium chloride solution and dried over magnesium sulfate. The crude product obtained after evaporation of the solvent is purified by chromatography on silica gel to give an oil, ν max. = 1740 (ketone carbonyl group), 1710 (acid carbonyl group), and 965 cm$^{-1}$ (trans vinyl group).

EXAMPLE 256≧295

Treatment of the 4-oxycyclopentenones listed in Table 17 below with the lithio methyldiisobutyl(1-transalkenyl)alanates, prepared from the 1-alkynes listed in Table 17, diisobutylaluminum hydride and methyl lithium, followed by deblocking the 11α-hydroxy and carboxylate groups all by the procedures described in Example 255, above, furnishes the product 9-oxo-11α-hydroxy-5-cis, 13-transprostadienoic acids of the table.

TABLE 17

| Example | Starting 4-oxy-cyclopentenone of Example | Starting 1-alkyne | Product 9-oxo-11α-hydroxy-5-cis,13-trans-prostadienoic acid |
|---|---|---|---|
| 256 | 45 | 1-octyne | 9-oxo-11α-hydroxy-5-cis,13-trans-prostadienoic acid |
| 257 | 37 | 1-nonyne | 9-oxo-11α-hydroxy-20-methyl-5-cis,13-trans-prostadienoic acid |
| 258 | 37 | 1-hexyne | 9-oxo-11α-hydroxy-19,20-dinor-5-cis,13-trans-prostadienoic acid |
| 259 | 37 | 8-chloro-1-octyne(ex. 122) | 9-oxo-11α-hydroxy-20-chloro-5-cis,13-trans-prostadienoic acid |
| 260 | 37 | 5-chloro-1-pentyne | 9-oxo-11α-hydroxy-17-chloro-18,19,20-trinor-5-cis,-13-trans-prostadienoic acid |
| 261 | 37 | 1-heptyne | 9-oxo-11α-hydroxy-20-nor-5-cis,13-trans-prostadienoic acid |
| 262 | 37 | cis-5-octen-1-yne (Ex. 121) | 9-oxo-11α-hydroxy-5-cis,13-trans,17-cis-prostatrienoic acid |
| 263 | 37 | 5-methyl-1-hexyne | 9-oxo-11α-hydroxy-17-methyl-19,20-dinor-5-cis,13-trans-prostadienoic acid |
| 264 | 38 | 1-heptyne | 9-oxo-11α-hydroxy-4,20-bisnor-5-cis,13-trans-prostadienoic acid |
| 265 | 38 | 1-octyne | 9-oxo-11α-hydroxy-4-nor-5-cis,13-trans-prostadienoic acid |
| 266 | 38 | 8-chloro-1-octyne | 9-oxo-11α-hydroxy-4-nor-20-chloro-5-cis,13-trans-prostadienoic acid |
| 267 | 39 | 1-octyne | 9-oxo-11α-hydroxy-4a-homo-5-cis,13-trans-prostadienoic acid |
| 268 | 39 | 1-nonyne | 9-oxo-11α-hydroxy-4a-homo-20-methyl-5-cis,13-trans-prostadienoic acid |
| 269 | 39 | 4-methyl-1-pentyne | 9-oxo-11α-hydroxy-4a-homo-16-methyl-18,19,20-trinor-5-cis,13-trans-prostadienoic acid |
| 270 | 39 | 8-chloro-1-octyne | 9-oxo-11α-hydroxy-4a-homo-20-chloro-5-cis,13-trans-prostadienoic acid |
| 271 | 39 | cis-5-octen-1-yne | 9-oxo-11α-hydroxy-4a-homo-5-cis,13-trans,17-cis-prostatrienoic acid |
| 272 | 40 | 1-decyne | 9-oxo-11α-hydroxy-4a,4b-bishomo-20-ethyl-5-cis,13-trans-prostadienoic acid |
| 273 | 40 | 1-octyne | 9-oxo-11α-hydroxy-4a,4b-bishomo-5-cis,13-trans-prostadienoic acid |
| 274 | 40 | 1-pentyne | 9-oxo-11α-hydroxy-4a,4b-bishomo-18,19,20-trinor-5-cis,13-trans-prostadienoic acid |
| 275 | 40 | 5-methyl-1-hexyne | 9-oxo-11α-hydroxy-4a,4b-bishomo-17-methyl-19,20-dinor-5-cis,13-trans-prostadienoic acid |
| 276 | 40 | 8-chloro-1-octyne | 9-oxo-11α-hydroxy-4a,4b-bishomo-20-chloro-5-cis,13-trans-prostadienoic acid |
| 277 | 40 | cis-5-octen-1-yne | 9-oxo-11α-hydroxy-4a,4b-bishomo-5-cis,13-trans,17-cis-prostatrienoic acid |
| 278 | 41 | 1-octyne | 9-oxo-11α-hydroxy-4-methyl-5-cis,13-trans-prostadienoic acid |
| 279 | 41 | 5-chloro-1-pentyne | 9-oxo-11α-hydroxy-4-methyl-17-chloro-18,19,20-trinor-5-cis,13-trans-prostadienoic acid |
| 280 | 41 | 1-dodecyne | 9-oxo-11α-hydroxy-4-methyl-20-n-butyl-5-cis,13-trans-prostadienoic acid |
| 281 | 42 | 1-octyne | 9-oxo-11α-hydroxy-4(R)-methyl-5-cis,13-trans-prostadienoic acid |
| 282 | 42 | 1-nonyne | 9-oxo-11α-hydroxy-4(R),20-dimethyl-5-cis,13-trans-prostadienoic acid |
| 283 | 42 | 1-pentyne | 9-oxo-11α-hydroxy-4(R)-methyl-18,19,20-trinor-5-cis,13-trans-prostadienoic acid |
| 284 | 42 | cis-5-octen-1-yne | 9-oxo-11α-hydroxy-4(R)-methyl-5-cis,13-trans,17-cis-prostatrienoic acid |
| 285 | 43 | 1-octyne | 9-oxo-11α-hydroxy-4-ethyl-5-cis,13-trans-prostadienoic acid |
| 286 | 43 | 8-chloro-1-octyne | 9-oxo-11α-hydroxy-4-ethyl-20-chloro-5-cis,13-trans-prostadienoic acid |
| 287 | 43 | 1-decyne | 9-oxo-11α-hydroxy-4-ethyl-20-ethyl-5-cis,13-trans-prostadienoic acid |
| 288 | 43 | 1-heptyne | 9-oxo-11α-hydroxy-4-ethyl-20-nor-5-cis,13-trans-prostadienoic acid |
| 289 | 43 | cis-5-octem-1-yne | 9-oxo-11α-hydroxy-4-ethyl-5-cis,13-trans,17-cis-prostatrienoic acid |
| 290 | 44 | cis-5-octem-1-yne | 9-oxo-11α-hydroxy-4-propyl-5-cis,13-trans,17-cis-prostatrienoic acid |
| 291 | 44 | 5-chloro-1-pentyne | 9-oxo-11α-hydroxy-4-propyl-17-chloro-18,19,20-trinor-5-cis,13-trans-prostadienoic acid |
| 292 | 44 | 1-octyne | 9-oxo-11α-hydroxy-4-propyl-5-cis,13-trans-prostadienoic acid |
| 293 | 44 | 5-methyl-1-hexyne | 9-oxo-11α-hydroxy-4-propyl-17-methyl-19,20-dinor-5-cis,13-trans-prostadienoic acid |
| 294 | 44 | 1-heptyne | 9-oxo-11α-hydroxy-4-propyl-20-nor-5-cis,13-trans-prostadienoic acid |
| 295 | 44 | 1-nonyne | 9-oxo-11α-hydroxy-4-propyl-20-methyl-5-cis,13-trans-prostadienoic acid |

EXAMPLE 296

Preparation of
9α,11α,16-trihydroxy-5-cis,13-trans-prostadienoic acid

To a stirred solution of 459 mg. of 9-oxo-11α,16-dihydroxy-5-cis,13-trans-prostadienoic acid (Example 149) in 4.0 ml. of tetrahydrofuran is added 5.2 ml. of a 0.65M solution of lithium perhydro-9b-boraphenalyl hydride in tetrahydrofuran at −78° C. under nitrogen. The solution is stirred at −78° C. for 45 minutes and at ambient temperatures for 15 minutes. The solution is diluted with 10 ml. of water and extracted with ether. The extract is back-extracted with N/4 sodium bicarbonate solution. The combined aqueous phases are acidified with 4N hydrochloric acid, saturated with sodium chloride, and extracted with ether. The extract is washed with saturated sodium chloride solution, dried over magnesium sulfate, and concentrated. The residue is purified by thin layer chromatography on silica gel to give a colorless oil, $\nu$ max. = 3310 (hydroxyl groups), 1705 (acid carbonyl group), and 970 cm$^{-1}$ (trans-vinyl group).

EXAMPLES 297–447

Reduction of the 9-oxo derivative listed in Table 18 below with lithium perhydro-9β-boraphenyalyl hydride by the method described in Example 296 furnishes the product 9α-hydroxy-5-cis,13-trans-prostadienoic acids of the table.

TABLE 18

| Example | Starting 9-oxo-5-cis,13-trans-prostadienoic acid of Example | Product 9α-hydroxy-5-cis,13-trans-prostadienoic acid |
|---|---|---|
| 297 | 150 | 9α,11α,16-trihydroxy-20-methyl-5-cis,13-trans-prostadienoic acid |
| 298 | 151 | 9α,11α,16-trihydroxy-20-ethyl-5-cis,13-trans-prostadienoic acid |
| 299 | 152 | 9α,11α,16-trihydroxy-20-nor-5-cis,13-trans-prostadienoic acid |
| 300 | 153 | 9α,11α,16-trihydroxy-19,20-dinor-5-cis,13,trans-prostadienoic acid |
| 301 | 154 | 9α,11α,16-trihydroxy-19-methyl-5-cis,13-trans-prostadienoic acid |
| 302 | 155 | 9α,11α,16-trihydroxy-17-ethyl-20-nor-5-cis,13-trans-prostadienoic acid |
| 303 | 156 | 9α,11α,16-trihydroxy-20-methyl-5-cis,13-trans,18-cis-prostatrienoic acid |
| 304 | 157 | 9α,11α,16-trihydroxy-18,19,20-trinor-5-cis,13-trans-prostadienoic acid |
| 305 | 158 | 9α,11α-dihydroxy-15-hydroxymethyl-5-cis,13-trans-prostadienoic acid |
| 306 | 159 | 9α,11α-dihydroxy-15-hydroxymethyl-20-nor-5-cis,13-trans-prostadienoic acid |
| 307 | 160 | 9α,11α,17-trihydroxy-5-cis,13-trans-prostadienoic acid |
| 308 | 161 | 9α,11α,18-trihydroxy-19,20-dinor-5-cis,13-trans-prostadienoic acid |
| 309 | 162 | 9α,11α,19-trihydroxy-20-nor-5-cis,13-trans-prostdienoic acid |
| 310 | 163 | 9α,11α,20-trihydroxy-cis,13-trans-prostadienoic acid |
| 311 | 164 | 9α,11α-dihydroxy-20-hydroxymethyl-5-cis,13-trans-prostadienoic acid |
| 312 | 165 | 9α,11α,17-trihydroxy-16-methyl-19,20-dinor-5-cis,13-trans-prostadienoic acid |
| 313 | 166 | 9α,11α,16-trihydroxy-4-methyl-5-cis,13-trans-prostadienoic acid |
| 314 | 167 | 9α,11α,16-trihydroxy-4,20-dimethyl-5-cis,13-trans-prostadienoic acid |
| 315 | 168 | 9α,11α,17-trihydroxy-4-methyl-16-ethyl-18,19,20-trinor-5-cis,13-trans-prostadienoic acid |
| 316 | 169 | 9α,11α,16-trihydroxy-4,20-dimethyl-5-cis,13-trans,18-cis-prostatrienoic acid |
| 317 | 170 | 9α,11α-dihydroxy-15-hydroxymethyl-4-methyl-5-cis,13-trans-prostadienoic acid |
| 318 | 171 | 9α,11α-dihydroxy-15-hydroxymethyl-4(R)-methyl-5-cis,13-trans-prostadienoic acid |
| 319 | 172 | 9α,11α,16-trihydroxy-4(R)-methyl-5-cis,13-trans-prostadienoic acid |
| 320 | 173 | 9α,11α,16-trihydroxy-4(R)-methyl-20-ethyl-5-cis,13-trans-prostadienoic acid |
| 321 | 174 | 9α,11α,20-trihydroxy-4(R)-methyl-5-cis,13-trans-prostadienoic acid |
| 322 | 175 | 9α,11α,17-trihydroxy-4(R)-methyl-19,20-dinor-5-cis,13-trans-prostadienoic acid |
| 323 | 176 | 9α,11α,16-trihydroxy-4(R),20-dimethyl-5-cis,13-trans,18-cis-prostatrienoic acid |
| 324 | 177 | 9α,11α,16-trihydroxy-4-ethyl-5-cis,13-trans-prostadienoic acid |
| 325 | 178 | 9α,11α,16-trihydroxy-4-ethyl-17-methyl-19,20-dinor-5-cis,13-trans-prostadienoic acid |
| 326 | 179 | 9α,11α-dihydroxy-4-ethyl-20-(-62 -hydroxyethyl)-5-cis,13-trans-prostadienoic acid |
| 327 | 180 | 9α,11α-dihydroxy-4-ethyl-15-hydroxymethyl-5-cis,13-trans-prostadienoic acid |
| 328 | 181 | 9α,11α,16-trihydroxy-4-ethyl-20-methyl-5-cis,13-trans,18-cis-prostatrienoic acid |
| 329 | 182 | 9α,11α,16-trihydroxy-4-propyl-5-cis,13-trans-prostadienoic acid |
| 330 | 183 | 9α,11α,17-trihydroxy-4-propyl-16-ethyl-19,20-dinor-5-cis,13-trans-prostadienoic acid |
| 331 | 184 | 9α,11α,16-trihydroxy-4-propyl-19-methyl-5-cis,13-trans-prostadienoic |
| 332 | 185 | 9α,11α,20-trihydroxy-4-propyl-5-cis,13-trans-prostadienoic acid |
| 333 | 186 | 9α,11α-dihydroxy-15-hydroxymethyl-4-propyl-5-cis,13-trans-prostadienoic acid |
| 334 | 187 | 9α,11α-dihydroxy-15-hydroxymethyl-4-propyl-19,20-dinor-5-cis,13- |

TABLE 18-continued

| Example | Starting 9-oxo-5-cis,13-trans-prostadienoic acid of Example | Product 9α-hydroxy-5-cis,13-trans-prostadienoic acid |
|---|---|---|
| 335 | 188 | trans-prostadienoic acid 9α,11α,16-trihydroxy-4-propyl-20-methyl-5-cis,13-trans,18-cis-prostatrienoic acid |
| 336 | 189 | 9α,11α,17-trihydroxy-4-propyl-5-cis,13-trans-prostadienoic acid |
| 337 | 190 | 9α,11α,16-trihydroxy-4-nor-5-cis,13-trans-prostadienoic acid |
| 338 | 191 | 9α,11α,16-trihydroxy-4,20-dinor-5-cis,13-trans-prostadienoic acid |
| 339 | 192 | 9α,11α,17-trihydroxy-4,19,20-trinor-18-methyl-5-cis,13-trans-prostadienoic acid |
| 340 | 193 | 9α,11α,19-trihydroxy-4,20-dinor-5-cis,13-trans-prostadienoic acid |
| 341 | 194 | 9α,11α-dihydroxy-15-hydroxymethyl-4-nor-5-cis,13-trans-prostadienoic acid |
| 342 | 195 | 9α,11α-dihydroxy-15-hydroxymethyl-4,20-dinor-5-cis,13-trans-prostadienoic acid |
| 343 | 196 | 9α,11α,16-trihydroxy-4a-homo-5-cis,13-trans-prostadienoic acid |
| 344 | 197 | 9α,11α,16-trihydroxy-4a-homo-20-methyl-5-cis,13-trans-prostadienoic acid |
| 345 | 198 | 9α,11α-17-trihydroxy-4a-homo-methyl-18,19,20-trinor-5-cis,13-trans-prostadienoic acid |
| 346 | 199 | 9α,11α-dihydroxy-4a-homo-15-hydroxymethyl-4-cis,13-trans-prostadienoic acid |
| 347 | 200 | 9α,11α-dihydroxy-4a-homo-15-hydroxymethyl-19,20-dinor-5-cis,13-trans-prostadienoic acid |
| 348 | 201 | 9α,11α,16-trihydroxy-4a-homo-20-methyl-5-cis,13-trans,18-cis-prostatrienoic acid |
| 349 | 202 | 9α,11α,19-trihydroxy-4a-homo-20-nor-5-cis,13-trans-prostadienoic acid |
| 350 | 203 | 9α,11α,16-trihydroxy-4a,4b-bishomo-5-cis,13-trans-prostadienoic acid |
| 351 | 203A | 9α,11α,17-trihydroxy-4a,4b-bishomo-5-cis,13-trans-prostadienoic acid |
| 352 | 203B | 9α,11α,16-trihydroxy-4a,4b-bishomo-20-ethyl-5-cis,13-trans-prostadienoic acid |
| 353 | 203C | 9α,11α,17-trihydroxy-4a,4b-bishomo-18,19,20-trinor-5-cis,13-trans-prostadienoic acid |
| 354 | 203D | 9α,11α,16-trihydroxy-4a,4b-bishomo-19-methyl-5-cis,13-trans-prostadienoic acid |
| 355 | 203E | 9α,11α-dihydroxy-4a,4b-bishomo-20-(γ-hydroxypropyl)-5-cis,13-trans-prostadienoic acid |
| 356 | 203F | 9α,11α,16-trihydroxy-4a,4b-bishomo-20-methyl-5-cis,13-trans-18-cis-prostatrienoic acid |
| 357 | 203G | 9α,11α-dihydroxy-15-hydroxymethyl-4a,4b-bishomo-5-cis,13-trans-prostadienoic acid |
| 358 | 203H | 9α,11α-dihydroxy-15-hydroxymethyl-4a,4b-bishomo-20-nor-5-cis,13-trans-prostadienoic acid |
| 359 | 206 | 9α,16-dihydroxy-20-methyl-5-cis,13-trans-prostadienoic acid |
| 360 | 207 | 9α,17-dihydroxy-5-cis,13-trans-prostadienoic acid |
| 361 | 208 | 9α,20-dihydroxy-5-cis,13-trans-prostadienoic acid |
| 362 | 209 | 9α,16-dihydroxy-17-methyl-19,20-dinor-5-cis,13-trans-prostadienoic acid |
| 363 | 210 | 9α,17-dihydroxy-16-methyl-19,20-dinor-5-cis,13-trans-prostadienoic acid |
| 364 | 211 | 9α-hydroxy-15-hydroxymethyl-5-cis,13-trans-prostadienoic acid |
| 365 | 212 | 9α-hydroxy-15-hydroxymethyl-20-nor-5-cis,13-trans-prostadienoic acid |
| 366 | 213 | 9α,16-dihydroxy-20-methyl-5-cis,13-trans,18-cis-prostatrienoic acid |
| 367 | 214 | 9α,16-dihydroxy-4-methyl-5-cis,13-trans-prostadienoic acid |
| 368 | 215 | 9α,19-dihydroxy-4-methyl-20-nor-5-cis,13-trans-prostadienoic acid |
| 369 | 216 | 9α,17-dihydroxy-4,16-dimethyl-18,19,20-trinor-5-cis,13-trans-prostadienoic acid |
| 370 | 217 | 9α-hydroxy-15-hydroxymethyl-4-methyl-5-cis,13-trans-prostadienoic acid |
| 371 | 218 | 9α,16-dihydroxy-4(R)-methyl-5-cis,13-trans-prostadienoic acid |
| 372 | 219 | 9α,16-dihydroxy-4(R),19-dimethyl-5-cis,13-trans-prostadienoic acid |
| 373 | 220 | 9α,16-dihydroxy-4(R)-methyl-17-ethyl-20-nor-5-cis,13-trans-prostadienoic acid |
| 374 | 221 | 9α,16-dihydroxy-4(R),20-dimethyl-5-cis,13-trans-prostadienoic acid |
| 375 | 222 | 9α-hydroxy-15-hydroxymethyl-4(R)-methyl-5-cis,13-trans-prostadienoic acid |
| 376 | 223 | 9α,16-dihydroxy-4(R),20-dimethyl-5-cis,13-trans-18-cis-prostatrienoic acid |
| 377 | 224 | 9α,16-dihydroxy-4-ethyl-20-methyl-5-cis,13-trans,18-cis-prostatrienoic acid |
| 378 | 225 | 9α,16-dihydroxy-4-ethyl-5-cis,13-trans-prostadienoic acid |
| 379 | 226 | 9α,16-dihydroxy-4,20-diethyl-5-cis,13-trans-prostadienoic acid |
| 380 | 227 | 9α,16-dihydroxy-4-ethyl- |

TABLE 18-continued

| Example | Starting 9-oxo-5-cis,13-trans-prostadienoic acid of Example | Product 9α-hydroxy-5-cis,13-trans-prostadienoic acid |
|---|---|---|
| 381 | 228 | 20-nor-5-cis,13-trans-prostadienoic acid |
| 381 | 228 | 9α-hydroxy-15-hydroxymethyl-4-ethyl-5-cis,13-trans-prostadienoic acid |
| 382 | 229 | 9α-hydroxy-20-(β-hydroxyethyl)-4-ethyl-5-cis,13-trans-prostadienoic acid |
| 383 | 230 | 9α,17-dihydroxy-4,16-diethyl-19,20-dinor-5-cis,13-trans-prostadienoic acid |
| 384 | 231 | 9α,16-dihydroxy-4-propyl-5-cis,13-trans-prostadienoic acid |
| 385 | 232 | 9α,16-dihydroxy-4-propyl-20-ethyl-5-cis,13-trans-prostadienoic acid |
| 386 | 233 | 9α-16-dihydroxy-4-propyl-19,20-dinor-5-cis,13-trans-prostadienoic acid |
| 387 | 234 | 9α,17-dihydroxy-4-propyl-16-ethyl-18,19,20-trinor-5-cis,13-trans-prostadienoic acid |
| 388 | 235 | 9α-hydroxy-15-hydroxymethyl-4-propyl-5-cis,13-trans-prostadienoic acid |
| 389 | 236 | 9α,16-dihydroxy-4-propyl-20-methyl-5-cis,13-trans,18-cis-prostatrienoic acid |
| 390 | 237 | 9α,16-dihydroxy-4-nor-20-methyl-5-cis,13-trans,18-cis-prostatrienoic acid |
| 391 | 238 | 9α,16-dihydroxy-4-nor-5-cis,13-trans-prostadienoic acid |
| 392 | 239 | 9α,16-dihydroxy-4,20-dinor-5-cis,13-trans-prostadienoic acid |
| 393 | 240 | 9α,17-dihydroxy-4,19,20-trinor-5-cis,13-trans-prostadienoic acid |
| 394 | 241 | 9α-hydroxy-15-hydroxymethyl-4,20-dinor-5-cis,13-trans-prostadienoic acid |
| 395 | 242 | 9α,16-dihydroxy-4a-homo-5-cis,13-trans-prostadienoic acid |
| 396 | 243 | 9α,16-dihydroxy-20-methyl-4a-homo-5-cis,13-trans-prostadienoic acid |
| 397 | 244 | 9α,16-dihydroxy-4a-homo-18,19,20-trinor-5-cis,13-trans-prostadienoic acid |
| 398 | 245 | 9α,16-dihydroxy-4a-homo-17-ethyl-20-nor-5-cis,13-trans-prostadienoic acid |
| 399 | 246 | 9α-hydroxy-15-hydroxymethyl-4a-homo-5-cis,13-trans-prostadienoic acid |
| 400 | 247 | 9α,16-dihydroxy-4a-homo-20-methyl-5-cis,13-trans,18-cis-prostatrienoic acid |
| 401 | 248 | 9α,16-dihydroxy-4a,4b-bishomo-5-cis,13-trans-prostadienoic acid |
| 402 | 249 | 9α,16-dihydroxy-4a,4b-bishomo-20-ethyl-5-cis,13-trans-prostadienoic acid |
| 403 | 250 | 9α,17-dihydroxy-4a,4b-bishomo-5-cis,13-trans-prostadienoic acid |
| 404 | 251 | 9α,16-dihydroxy-4a,4b-bishomo-19-methyl-5-cis,13-trans-prostadienoic acid |
| 405 | 252 | 9α-hydroxy-15-hydroxymethyl-4a,4b-bishomo-5-cis,13-trans-prostadienoic acid |
| 406 | 253 | 9α,18-dihydroxy-4a,4b-bishomo-19,20-dinor-5-cis,13-trans-prostadienoic acid |
| 407 | 254 | 9α,16-dihydroxy-4a,4b-bishomo-20-methyl-5-cis,13-trans,18-cis-prostatrienoic acid |
| 408 | 256 | 9α,11α-dihydroxy-5-cis,13-trans-prostadienoic acid |
| 409 | 257 | 9α,11α-dihydroxy-20-methyl-5-cis,13-trans-prostadienoic acid |
| 410 | 258 | 9α,11α-dihydroxy-19,20-dinor-5-cis,13-trans-prostadienoic acid |
| 411 | 259 | 9α,11α-dihydroxy-20-chloro-5-cis,13-trans-prostadienoic acid |
| 412 | 260 | 9α,11α-dihydroxy-17-chloro-18,19,20-trinor-5-cis,13-trans-prostadienoic acid |
| 413 | 261 | 9α,11α-dihydroxy-20-nor-5-cis,13-trans-prostadienoic acid |
| 414 | 262 | 9α,11α-dihydroxy-5-cis,13-trans,17-cis-prostatrienoic acid |
| 415 | 263 | 9α,11α-dihydroxy-17-methyl-19,20-dinor-5-cis,13-trans-prostadienoic acid |
| 416 | 264 | 9α,11α-dihydroxy-4,20-bisnor-5-cis,13-trans-prostadienoic acid |
| 41 | 265 | 9α,11α-dihydroxy-4-nor-5-cis,13-trans-prostadienoic acid |
| 418 | 266 | 9α,11α-dihydroxy-4-nor-20-chloro-5-cis,13-trans-prostadienoic acid |
| 419 | 267 | 9α,11α-dihydroxy-4a-homo-5-cis,13-trans-prostadienoic acid |
| 420 | 268 | 9α,11α-dihydroxy-4a-homo-20-methyl-5-cis,13-trans-prostadienoic acid |
| 421 | 269 | 9α,11α-dihydroxy-4a-homo-16-methyl-18,19,20-trinor-5-cis,13-trans-prostadienoic acid |
| 422 | 270 | 9α,11α-dihydroxy-4a-homo-20-chloro-5-cis,13-trans-prostadienoic acid |
| 423 | 271 | 9α,11α-dihydroxy-4a-homo-5-cis,13-trans,17-cis-prostatrienoic acid |
| 424 | 272 | 9α,11α-dihydroxy-4a,4b-bishomo-20-ethyl-5-cis,3-trans-prostadienoic acid |
| 425 | 273 | 9α,11α-dihydroxy-4a,4b,bishomo-5-cis,13-trans-prostadienoic acid |
| 426 | 274 | 9α,11α-dihydroxy-4a,4b-bishomo-18,19,20-trinor-5-cis,13-trans-prostadienoic acid |
| 427 | 275 | 9α,11α-dihydroxy-4a,4b-bishomo-17-methyl-19,20-dinor-5-cis,13-trans-prostadienoic acid |

TABLE 18-continued

| Example | Starting 9-oxo-5-cis,13-trans-prostadienoic acid of Example | Product 9α-hydroxy-5-cis,13-trans-prostadienoic acid |
|---|---|---|
| 428 | 276 | 9α,11α-dihydroxy-4a,4b-bishomo-20-chloro-5-cis,13-trans-prostadienoic acid |
| 429 | 277 | 9α,11α-dihydroxy-4a,4b-bishomo-5-cis,13-trans-17-cis-prostatrienoic acid |
| 430 | 278 | 9α,11α-dihydroxy-4-methyl-5-cis,13-trans-prostadienoic acid |
| 431 | 279 | 9α,11α-dihydroxy-4-methyl-17-chloro-18,19,20-trinor-5-cis,13-trans-prostadienoic acid |
| 432 | 280 | 9α,11α-dihydroxy-4-methyl-20-n-butyl-5-cis,13-trans-prostadienoic acid |
| 433 | 281 | 9α,11α-dihydroxy-4(R)-methyl-5-cis,13-trans-prostadienoic acid |
| 434 | 282 | 9α,11α-dihydroxy-4(R),20-dimethyl-5-cis,13-trans-prostadienoic acid |
| 435 | 283 | 9α,11α-dihydroxy-4(R)-methyl-18,19,20-trinor-5-cis,13-trans-prostadienoic acid |
| 436 | 284 | 9α,11α-dihydroxy-4(R)-methyl-5-cis,13-trans,17-cis-prostatrienoic acid |
| 437 | 285 | 9α,11α-dihydroxy-4-ethyl-5-cis,13-trans-prostadienoic acid |
| 438 | 286 | 9α,11α-dihydroxy-4-ethyl-20-chloro-5-cis,13-trans-prostadienoic acid |
| 439 | 287 | 9α,11α-dihydroxy-4-ethyl-20-ethyl-5-cis,13-trans-prostadienoic acid |
| 440 | 288 | 9α,11α-dihydroxy-4-ethyl-20-nor-5-cis,13-trans-prostadienoic acid |
| 441 | 289 | 9α,11α-dihydroxy-4-ethyl-5-cis,13-trans,17-cis-prostatrienoic acid |
| 442 | 290 | 9α,11α-dihydroxy-4-propyl-5-cis,13-trans-17-cis-prostatrienoic acid |
| 443 | 291 | 9α,11α-dihydroxy-4-propyl-17-chloro-18,19,20-trinor-5-cis,13-trans-prostadienoic acid |
| 444 | 292 | 9α,11α-dihydroxy-4-propyl-5-cis,13-trans-prostadienoic acid |
| 445 | 293 | 9α,11α-dihydroxy-4-propyl-17-methyl-19,20-dinor-5-cis,13-trans-prostadienoic acid |
| 446 | 294 | 9α,11α-dihydroxy-4-propyl-20-nor-5-cis,13-trans-prostadienoic acid |
| 447 | 295 | 9α,11α-dihydroxy-4-propyl-20-methyl-5-cis,13-trans-prostadeinoic acid |

EXAMPLE 448

Preparation of 9-oxo-16-hydroxy-5-cis-10,13-trans-prostatrienoic acid

A solution of 1.52 g. (4.3 mmoles) of 9-oxo-11α,16-dihydroxy-5-cis,13-trans-prostadienoic acid (Example 149) in 80 ml. of 0.5NHCl in 1:1 THF-H$_2$O is allowed to stand at room temperature under nitrogen for 67 hours. The solution is treated with brine and extracted with ether. The extract is washed with brine and dried over magnesium sulfate. The residue remaining after evaporation of the solvent is purified by partition chromatography on Celite to give an oil, ν max (film) 1700 (ketone and acid carbonyl groups), 1580 (conjugated olefin), and 967 cm$^{-1}$ (trans-olefin).

EXAMPLES 449–550

Treatment of the 9-oxo-11α-hydroxy-5-cis,13-trans-prostadienoic acids listed in Table 19 below with dilute acid in accordance with the method described in Example 448 furnishes the product 9-oxo-5-cis,10,13-trans-prostatrienoic acids of the table.

TABLE 19

| Example | Starting 9-oxo-11α-hydroxy-5-cis,13-trans-prostadienoic acid of Example | Product 9-oxo-5-cis-10,13-trans-prostatrienoic acid |
|---|---|---|
| 449 | 150 | 9-oxo-16-hydroxy-20-methyl-5-cis,10,13-trans-prostatrienoic acid |
| 450 | 151 | 9-oxo-16-hydroxy-20-ethyl-5-cis,10,13-trans-prostatrienoic acid |
| 451 | 152 | 9-oxo-16-hydroxy-20-non-5-cis,10,13-trans-prostatrienoic acid |
| 452 | 153 | 9-oxo-16-hydroxy-19,20-dinor-5-cis,10,13-trans-prostatrienoic acid |
| 453 | 154 | 9-oxo-16-hydroxy-19-methyl-5-cis,10,13-trans-prostatrienoic acid |
| 454 | 155 | 9-oxo-16-hydroxy-17-ethyl-20-nor-5-cis,-10,13-trans-prostatrienoic acid |
| 455 | 156 | 9-oxo-16-hydroxy-20-methyl-5-cis,10,13-trans,18-cis-prostatetraenoic acid |
| 456 | 157 | 9-oxo-16-hydroxy-18,19,-20-trinor-5-cis,10,13-trans-prostatrienoic acid |
| 457 | 158 | 9-oxo-15-hydroxymethyl-5-cis,10,13-trans-prostatrienoic acid |
| 458 | 159 | 9-oxo-15-hydroxymethyl-20-nor-10,13-trans-prostatrienoic acid |
| 459 | 160 | 9-oxo-17-hydroxy-5-cis,-10,13-trans-prostatrienoic acid |
| 460 | 161 | 9-oxo-18-hydroxy-19,20-dinor-5-cis,10,13-trans-prostatrienoic acid |
| 461 | 162 | 9-oxo-19-hydroxy-20-nor-5-cis,10,13-trans-prostatrienoic acid |
| 462 | 163 | 9-oxo-20-hydroxy-5-cis,-10,13-trans-prostatrienoic acid |
| 463 | 164 | 9-oxo-20-hydroxymethyl-5-cis,10,13-trans-prostatrienoic acid |
| 464 | 165 | 9-oxo-17-hydroxy-16-methyl-19,20-dinor-5-cis,10,13-trans-prostatrienoic acid |
| 465 | 166 | 9-oxo-16-hydroxy-4-methyl-5-cis,10,13-trans-prostatrienoic acid |
| 466 | 167 | 9-oxo-16-hydroxy-4,20-dimethyl-5-cis,10,13-trans-prostatrienoic acid |
| 467 | 168 | 9-oxo-17-hydroxy-4-methyl-16-ethyl-18,19,- |

TABLE 19-continued

| Example | Starting 9-oxo-11α-hydroxy-5-cis,13-trans-prostadienoic acid of Example | Product 9-oxo-5-cis-10,13-trans-prostatrienoic acid |
|---|---|---|
| | | 20-trinor-5-cis,10,13-trans-prostatrienoic acid |
| 468 | 169 | 9-oxo-16-hydroxy-4,20-dimethyl-5-cis,10,13-trans,18-cis-prostatetraenoic acid |
| 469 | 170 | 9-oxo-15-hydroxymethyl-4-methyl-5-cis,10,13-trans-prostatrienoic acid |
| 470 | 171 | 9-oxo-15-hydroxymethyl-4(R)-methyl-5-cis,10,13-trans-prostatrienoic acid |
| 471 | 172 | 9-oxo-16-hydroxy-4(R)-methyl-5-cis,10,13-trans-prostatrienoic acid |
| 472 | 173 | 9-oxo-16-hydroxy-4(R)-methyl-20-ethyl-5-cis,10,13-trans-prostatrienoic acid |
| 473 | 174 | 9-oxo-20-hydroxy-4(R)-methyl-5-cis,10,13-trans-prostatrienoic acid |
| 474 | 175 | 9-oxo-17-hydroxy-4(R)-methyl-19,20-dinor-5-cis,10,13-trans-prostatrienoic acid |
| 475 | 176 | 9-oxo-16-hydroxy-4(R),20-dimethyl-5-cis,10,13-trans,18-cis-prostatetraenoic acid |
| 476 | 177 | 9-oxo-16-hydroxy-4-ethyl-5-cis,10,13-trans-prostatrienoic acid |
| 477 | 178 | 9-oxo-16-hydroxy-4-ethyl-17-methyl-19,20-dinor-5-cis,10,13-trans-prostatrienoic acid |
| 478 | 179 | 9-oxo-4-ethyl-20-(β-hydroxyethyl)-5-cis,10,13-trans-prostatrienoic acid |
| 479 | 180 | 9-oxo-4-ethyl-15-hydroxymethyl-5-cis,10,13-trans-prostatrienoic acid |
| 480 | 181 | 9-oxo-16-hydroxy-4-ethyl-20-methyl-5-cis,10,13-trans,18-cis,-prostatetraenoic acid |
| 481 | 182 | 9-oxo-16-hydroxy-4-propyl-5-cis,10,13-trans-prostatrienoic acid |
| 482 | 183 | 9-oxo-17-hydroxy-4-propyl-16-ethyl-19,20-dinor-5-cis,10,13-trans-prostatrienoic acid |
| 483 | 184 | 9-oxo-16-hydroxy-4-propyl-19-methyl-5-cis,10,13-trans-prostatrienoic acid |
| 484 | 185 | 9-oxo-20-hydroxy-4-propyl-5-cis,10,13-trans-prostatrienoic acid |
| 485 | 186 | 9-oxo-15-hydroxymethyl-4-propyl-5-cis,10,13-trans-prostatrienoic acid |
| 486 | 187 | 9-oxo-15-hydroxymethyl-4-propyl-19,20-dinor-5-cis,10,13-trans-prostatrienoic acid |
| 487 | 188 | 9-oxo-16-hydroxy-4-propyl-20-methyl-5-cis,10,13-trans,18-cis-prostatetraenoic acid |
| 488 | 189 | 9-oxo-17-hydroxy-4-propyl-5-cis,10,13-trans-prostatrienoic acid |
| 489 | 190 | 9-oxo-16-hydroxy-4-nor-5-cis,10,13-trans-prostatrienoic acid |
| 490 | 191 | 9-oxo-16-hydroxy-4,20-dinor-5-cis,10,13-trans-prostatrienoic acid |
| 491 | 192 | 9-oxo-17-hydroxy-4,19,20-trinor-16-methyl-5-cis,10,13-trans-prostatrienoic acid |
| 492 | 193 | 9-oxo-19-hydroxy-4,20-dinor-5-cis,10,13-trans-prostatrienoic acid |
| 493 | 194 | 9-oxo-15-hydroxymethyl-4-nor-5-cis,10,13-trans-prostatrienoic acid |
| 494 | 195 | 9-oxo-15-hydroxymethyl-4,20-dinor-5-cis,10,13-trans-prostatrienoic acid |
| 495 | 196 | 9-oxo-16-hydroxy-4a-homo-5-cis,10,13-trans-prostatrienoic acid |
| 496 | 197 | 9-oxo-16-hydroxy-4a-homo-20-methyl-5-cis,10,13-trans-prostatrienoic acid |
| 497 | 198 | 9-oxo-17-hydroxy-4a-homo-16-methyl-18,19,20-trinor-5-cis,10,13-trans-prostatrienoic acid |
| 498 | 199 | 9-oxo-4a-homo-15-hydroxymethyl-5-cis,10,13-trans-prostatrienoic acid |
| 499 | 200 | 9-oxo-4a-homo-15-hydroxymethyl-19,20-dinor-5-cis,10,13-trans-prostatrienoic acid |
| 500 | 201 | 9-oxo-16-hydroxy-4a-homo-20-methyl-5-cis,10,13-trans,18-cis-prostatetraenoic acid |
| 501 | 202 | 9-oxo-19-hydroxy-4a-homo-20-nor-5-cis,10,13-trans-prostatrienoic acid |
| 502 | 203 | 9-oxo-16-hydroxy-4a,4b-bishomo-5-cis,10,13-trans-prostatrienoic acid |
| 503 | 203A | 9-oxo-17-hydroxy-4a,4b-bishomo-5-cis,10,13-trans-prostatrienoic acid |
| 504 | 203B | 9-oxo-16-hydroxy-4a,4b-bishomo-20-ethyl-5-cis,10,13-trans-prostatrienoic acid |
| 505 | 203C | 9-oxo-17-hydroxy-4a,4b-bishomo-18,19,20-trinor-5-cis,10,13-trans-prostatrienoic acid |
| 506 | 203D | 9-oxo-16-hydroxy-4a,4b-bishomo-19-methyl-5-cis,10,13-trans-prostatrienoic acid |
| 507 | 203E | 9-oxo-4a,4b-bishomo-20-(γ-hydroxypropyl)-5-cis,10,13-trans-prostatrienoic acid |
| 508 | 203F | 9-oxo-16-hydroxy-4a,4b-bishomo-20-methyl-5-cis,10,13-trans,18-cis-prostatetraenoic acid |
| 509 | 203G | 9-oxo-15-hydroxymethyl-4a,4b-bishomo-5-cis,10,13-trans-prostatrienoic acid |
| 510 | 203H | 9-oxo-15-hydroxymethyl-4a,4b-bishomo-20-nor-5-cis,10,13-trans- |

TABLE 19-continued

| Example | Starting 9-oxo-11α-hydroxy-5-cis,13-trans-prostadienoic acid of Example | Product 9-oxo-5-cis-10,13-trans-prostatrienoic acid |
|---|---|---|
| 511 | 256 | prostatrienoic acid 9-oxo-5-cis,10,13-trans-prostatrienoic acid |
| 512 | 257 | 9-oxo-20-methyl-5-cis,-10,13-trans-prostatrienoic acid |
| 513 | 258 | 9-oxo-19,20-dinor-5-cis,10,13-trans-prostatrienoic acid |
| 514 | 259 | 9-oxo-20-chloro-5-cis,-10,13-trans-prostatrienoic acid |
| 515 | 260 | 9-oxo-17-chloro-18,19,-20-trinor-5-cis,10,13-trans-prostatrienoic acid |
| 516 | 261 | 9-oxo-20-nor-5-cis,10,-13-trans-prostatrienoic acid |
| 517 | 262 | 9-oxo-5-cis,10,13-trans,17-cis-prostatrienoic acid |
| 518 | 263 | 9-oxo-17-methyl-19,20-dinor-5-cis,10,13-trans-prostatrienoic acid |
| 519 | 264 | 9-oxo-4,20-bisnor-5-cis-10,13-trans-prostatrienoic acid |
| 520 | 265 | 9-oxo-4-nor-5-cis,10,-13-trans-prostatrienoic acid |
| 521 | 266 | 9-oxo-4-nor-20-chloro-5-cis,10,13-trans-prostatrienoic acid |
| 522 | 267 | 9-oxo-4a-homo-5-cis,10,-13-trans-prostatrienoic acid |
| 523 | 268 | 9-oxo-4a-homo-20-methyl-5-cis,10,13-trans-prostatrienoic acid |
| 524 | 269 | 9-oxo-4a-homo-16-methyl-18,19,20-trinor-5-cis,-10,13-trans-prostatrienoic acid |
| 525 | 270 | 9-oxo-4a-homo-20-chloro-5-cis,10,13-trans-prostatrienoic acid |
| 526 | 271 | 9-oxo-4a-homo-5-cis,-10,13-trans,17-cis-prostatetraenoic acid |
| 527 | 272 | 9-oxo-4a,4b-bishomo-20-ethyl-5-cis,10,13-trans-prostatrienoic acid |
| 528 | 273 | 9-oxo-4a,4b-bishomo-5-bis,10,13-trans-prostatrienoic acid |
| 529 | 274 | 9-oxo-4a,4b-bishomo-18,19,20-trinor-5-cis,-10,13-trans-prostatrienoic acid |
| 530 | 275 | 9-oxo-4a,4b-bishomo-17-methyl-19,20-dinor-5-cis,10,13-trans-prostatrienoic acid |
| 531 | 276 | 9-oxo-4a,4b-bishomo-20-chloro-5-cis,10,13-trans-prostatrienoic acid |
| 532 | 277 | 9-oxo-4a,4b-bishomo-5-cis,10,13-trans,17-cis-prostatetraenoic acid |
| 533 | 278 | 9-oxo-4-methyl-5-cis,-10,13-trans-prostatrienoic acid |
| 534 | 279 | 9-oxo-4-methyl-17-chloro-18,19,20-trinor-5-cis,10,13-trans-prostatrienoic acid |
| 535 | 280 | 9-oxo-4-methyl-20-n-butyl-5-cis,10,13-trans-prostatrienoic acid |
| 536 | 281 | 9-oxo-4(R)-methyl-5-cis,10,13-trans-prostatrienoic acid |
| 537 | 282 | 9-oxo-4(R),20-dimethyl-5-cis,10,13-trans-prostatrienoic acid |
| 538 | 283 | 9-oxo-4(R)-methyl-18,-19,20-trinor-5-cis,10,-13-trans-prostatrienoic acid |
| 539 | 284 | 9-oxo-4(R)-methyl-5-cis,10,13-trans,17-cis-prostatetraenoic acid |
| 540 | 285 | 9-oxo-4-ethyl-5-cis,10,-13-trans-prostatrienoic acid |
| 541 | 286 | 9-oxo-4-ethyl-20-chloro-5-cis,10,13-trans-prostatrienoic acid |
| 542 | 287 | 9-oxo-4-ethyl-20-ethyl-5-cis,10,13-trans-prostatrienoic acid |
| 543 | 288 | 9-oxo-4-ethyl-20-nor-5-cis,10,13-trans-prostatrienoic acid |
| 544 | 289 | 9-oxo-4-ethyl-5-cis,10,-13-trans,17-cis-prostatetraenoic acid |
| 545 | 290 | 9-oxo-4-propyl-5-cis,-10,13-trans,17-cis-prostatetraenoic acid |
| 546 | 291 | 9-oxo-4-propyl-17-chloro-18,19,20-trinor-5-cis,10,13-trans-prostatrienoic acid |
| 547 | 292 | 9-oxo-4-propyl-5-cis,-10,13-trans-prostatrienoic acid |
| 548 | 293 | 9-oxo-4-propyl-17-methyl-19,20-dinor-5-cis,10,13-trans-prostatrienoic acid |
| 549 | 294 | 9-oxo-4-propyl-20-nor-5-cis,10,13-trans-prostatrienoic acid |
| 550 | 295 | 9-oxo-4-propyl-20-methyl-5-cis,10,13-trans-prostatrienoic acid |

EXAMPLE 551

Preparation of 9α/β,11,16-trihydroxy-5-cis,13-trans-prostadienoic acid

To a stirred, ice cold solution of 355 mg. 9-oxo-11α,16-dihydroxy-9-oxo-5-cis,13-trans-prostadienoic acid (Example 149) in 50 ml. of ethanol is added 409 mg. of sodium borohydride in small portions during 1 minute. The mixture is stirred at 0° C. for 5 minutes and at ambient temperature for 1.5 hour. The bulk of the ethanol is evaporated at room temperature, and the residue is treated with ether followed by dilute hydrochloric acid while cooling in an ice bath. The organic phase is separated and washed with water and saturated sodium chloride solution. The solution is dried over magnesium sulfate and concentrated. The residue is purified by thin layer chromatography on silica gel to give an oil, which is a mixture of 9α- and 9β-hydroxy derivatives, ν max. 3310 (hydroxyl groups), 1705 (acid carbonyl group), and 970 cm$^{-1}$ (trans-vinyl group).

EXAMPLES 552–559

Treatment of the 9-oxo derivatives listed in the table below with sodium borohydride in accordance with the procedure described in Example 551 is productive of the 9α/β-hydroxy derivatives of the table. Each of these products represents a mixture of 9α- and 9β-hydroxy compounds.

TABLE 20

| Example | Starting 9-oxo derivatives of Example | Product 9α/β-hydroxy mixture |
|---|---|---|
| 552 | 160 | 9α/β,11α,17-trihydroxy-5-cis,13-trans-prostadienoic acid |
| 553 | 163 | 9α/β,11α,20-trihydroxy-5-cis,13-trans-prostadienoic acid |
| 554 | 171 | 9α/β,11α-dihydroxy-15-hydroxymethyl-4(R)methyl-5-cis,13-trans-prostadienoic acid |
| 555 | 199 | 9α/β,11α-dihydroxy-15-hydroxymethyl-4a-homo-5-cis,13-trans-prostadienoic acid |
| 556 | 205 | 9α/β,16-dihydroxy-5-cis,13-trans-prostadienoic acid |
| 557 | 208 | 9α/β,20-dihydroxy-5-cis,13-trans-prostadienoic acid |
| 558 | 255 | 9α/β,11α-dihydroxy-5-cis,13-trans-prostadienoic acid |
| 559 | 262 | 9α/β,11α-dihydroxy-5-cis,13-trans,17-cis-prostatrienoic acid |

EXAMPLES 560-586

Treatment of the prostadienoic acids listed in Table 21 below with the indicated diazoalkane in the following manner provides the product prostadienoate esters of the table.

An ethereal solution containing a molar excess of diazoalkane is added to a solution of prostadienoic acid in ether (or acetone). After 2 to 4 hours the solution is carefully evaporated under vacuum and the residual prostadienoate ester is purified in the usual way by chromatography on silica gel.

EXAMPLE 587

Preparation of 2-methylhexanol

To a stirred solution of 27 g. (170 mmoles) of ethyl 2-methylhexanoate in 300 ml. of toluene at −75° is added dropwise 225 ml. of 0.91 M diisobutylaluminum hydride in toluene during 45 minutes. The solution is then stirred at −75° for 2 hours and is treated dropwise with 400 ml. of saturated sodium bisulfate solution. The mixture is warmed to room temperature and filtered. The aqueous layer is basified with 10 N sodium hydroxide and extracted with ether. The extract is washed to neutrality with brine, dried over magnesium sulfate, and concentrated to give a liquid, i.r. (film) 1715 cm$^{-1}$ (aldehyde group).

EXAMPLE 588

Preparation of 2,2-Dimethylpentanol

To a refluxing solution of 2.4 M n-butyl-magnesium chloride (1.07 moles) in tetrahydrofuran is added dropwise 153 g. (1.0 moles) of isobutyraldehyde cyclohexylimine [G. Stork and S. R. Dowd, J. Amer. Chem. Soc., 85, 2178 (1963)]. The stirred mixture is heated at reflux until evolution of butane ceases. To the stirred refluxing solution is added 123 g. (1.0 moles) of n-propyl bromide dropwise. The stirred mixture is heated at reflux temperature overnight, cooled, and slowly treated with a solution of 150 ml. of concentrated hydrochloric acid and 350 ml. of water. The resulting mixture is heated at reflux for 4 hours, cooled, saturated with sodium chloride, and extracted with ether. The extract is washed with sodium bicarbonate solution and brine, dried over sodium sulfate, and concentrated.

The residue is distilled to provide 39.9 g. of colorless liquid, boiling point 28.5°-30° (5 mm.).

TABLE 21

| Example | Starting prostadienoic acid of Example | Diazoalkane | Product alkyl prostadienoate |
|---|---|---|---|
| 560 | 149 | diazomethane | methyl 9-oxo-11α,16-dihydroxy-5-cis,13-trans-prostadienoate |
| 561 | 149 | diazopentane | pentyl 9-oxo-11α,16-dihydroxy-5-cis,13-trans-prostadienoate |
| 562 | 149 | diazoheptane | heptyl 9-oxo-11α,16-dihydroxy-5-cis, 13-trans-prostadienoate |
| 563 | 149 | diazodecane | decyl 9-oxo-11α,16-dihydroxy-5-cis,13-trans-prostadienoate |
| 564 | 160 | diazodecane | decyl 9-oxo-11α,17-dihydroxy-5-cis,13-trans-prostadienoate |
| 565 | 163 | diazoheptane | heptyl 9-oxo-11α,dihydroxy-5-cis,13-trans-prostadienoate |
| 566 | 158 | diazopentane | pentyl 9-oxo-11α-hydroxy-15-hydroxymethyl-5-cis,13-trans- |
| 567 | 172 | diazoheptane | heptyl 9-oxo-11α,16-dihydroxy-4(R)-methyl-5-cis,13-trans-prostadienoate |
| 568 | 156 | diazodecane | decyl 9-oxo-11α,16-dihydroxy-20-methyl-5-cis,13-trans,18-cis-prostatrienoate |
| 569 | 206 | diazodecane | decyl 9-oxo-16-hydroxy-20-methyl-5-cis, 13-trans-prostadienoate |
| 570 | 253 | diazodecane | decyl 9-oxo-18-hydroxy-4a,4b-bishomo-19,20-dinor-5-cis,13-trans-prostadienoate |
| 571 | 255 | diazodecane | decyl 9-oxo-11α-hydroxy-5-cis,13-trans-prostadienoate |
| 572 | 255 | diazopentane | pentyl 9-oxo-11α-hydroxy-5-cis, 13-trans-prostadienoate |
| 573 | 266 | diazoheptane | heptyl 9-oxo-11α-hydroxy-4-nor-20-chloro-5-cis,13-trans-prostadienoate |
| 574 | 272 | diazoheptane | heptyl 9-oxo-11α-hydroxy-4a,4b-bishomo-20-ethyl-5-cis,13-trans-prostadienoate |
| 575 | 289 | diazodecane | decyl 9-oxo-11α-hydroxy-4-ethyl-5-cis,13-trans,17-cis-prostatrienoate |
| 576 | 296 | diazodecane | decyl 9α,11α,16α-trihydroxy-5-cis,13-trans-prostadienoate |
| 577 | 296 | diazoheptane | heptyl 9α,11α,16α-trihydroxy-5-cis,13-trans-prostadienoate |
| 578 | 296 | diazopentane | pentyl 9α,11α,16α-trihydroxy-5-cis,13-trans-prostadienoate |
| 579 | 296 | diazomethane | methyl 9α,11α,16α-trihydroxy-5-cis,13-trans-prostadienoate |
| 580 | 298 | diazodecane | decyl 9α,11α,16α-trihydroxy-20-ethyl-5-cis,13-trans-prostadienoate |
| 581 | 314 | diazodecane | decyl 9α,11α,16α-trihydroxy-4,20-dimethyl-5-cis,13-trans-prostadienoate |
| 582 | 408 | diazodecane | decyl 9α,11α-dihydroxy-5-cis,13-trans-prostadienoate |
| 583 | 448 | diazodecane | decyl 9-oxo-16-hydroxy-5-cis,10,13-trans-prostatrienoate |
| 584 | 448 | diazoheptane | heptyl 9-oxo-16-hydroxy-5-cis,10,13-trans-prostatrienoate |
| 585 | 448 | diazopentane | pentyl 9-oxo-16-hydroxy-5-cis,10,13-trans-prostatrienoate |
| 586 | 511 | diazodecane | decyl 9-oxo-5-cis,10,13-trans-prostatrienoate |

EXAMPLES 589 and 590

The alkyl halides of Table 22 below are converted to the product aldehydes of the table by the procedure described in Example 588.

TABLE 22

| Example | Starting alkyl halide | Product aldehyde |
|---|---|---|
| 589 | n-butyliodide | 2,2-dimethylhexanal |
| 590 | trans-crotyl bromide | 2,2-dimethyl-4-trans-hexenal |

EXAMPLES 591–599

The starting aldehydes or ketones of Table 23 below are converted to the product 1-alkyn-4-ols of the table by the procedure described in Example 87.

TABLE 23

| Example | Starting aldehyde or ketone | Product 1-alkyn-4-ol |
|---|---|---|
| 591 | trans-2-hexenal | 4-hydroxy-5-trans-nonen-1-yne |
| 592 | 2,2-dimethylhexanal | 5,5-dimethyl-4-hydroxy-1-nonyne |
| 593 | 2,2-dimethy-4-trans-hexenal | 5,5-dimethyl-4-hydroxy-7-trans-nonen-1-yne |
| 594 | 2,2-dimethylpentanal | 5,5-dimethyl-4-hydroxy-1-octyne |
| 595 | 2-methylpentanal | 5-methyl-4-hydroxy-1-octyne |
| 596 | 2-methylhexanal | 5-methyl-4-hydroxy-1-nonyne |
| 597 | 2-hexanone | 4-hydroxy-4-methyl-1-octyne |
| 598 | trans-3-hexen-2-one[a] | 4-hydroxy-4-methyl-5-trans-octen-1-yne |
| 599 | trans-2-pentenal[b] | 4-hydroxy-5-trans-octen-1-yne |

[a] G. Sturtz, Bull. Soc. Chim. Fr., 1967, 2477.
[b] R. I. Hoaglin and D. M. Hirsh, U.S. Pat. No. 2,628,257; Chim. Abstr., 48, 1423e (1954).

EXAMPLE 600

Preparation of 4-Methyl-4-trimethylsilyloxy-1-octyne

To a stirred solution of 75.4 g. (0.537 moles) of 4-hydroxy-4-methyl-1-octyne (Example 597), 104.9 g. (1.54 moles) of imidazole, and 325 ml. of dimethylformamide is added 65.2 g. (0.60 moles) of chlorotrimethylsilane. After standing overnight the mixture is poured into 800 ml. of hexane. The mixture is washed thoroughly with water followed by sodium bicarbonate solution and brine. The solution is dried over magnesium sulfate, filtered, and evaporated to give a liquid, p.m.r. spectrum, $\delta$ 1.26 (singlet, 3, $CH_3$), 1.92 (triplet, 1, HC≡), 2.30 (doublet, 2, $CH_2$).

EXAMPLES 601–604

The 1-alkyn-4-ols of Table 24 are converted to the product trimethylsilyl ethers of the table by treatment with chlorotrimethylsilane according to the procedure described in Example 600.

TABLE 24

| Example | Starting 1-alkyn-4-ol | Product trimethylsilyl ether |
|---|---|---|
| 601 | 5,5-dimethyl-4-hydroxy-1-nonyne | 5,5-dimethyl-4-trimethylsilyloxy-1-nonyne |
| 602 | 5,5-dimethyl-4-hydroxy-7-trans-nonen-1-yne | 5,5-dimethyl-4-trimethylsilyloxy-7-trans-nonen-1-yne |
| 603 | 5,5-dimethyl-4-hydroxy-1-octyne | 5,5-dimethyl-4-trimethylsilyloxy-1-octyne |
| 604 | 4-hydroxy-4-methyl-5-trans-octen-1-yne | 4-methyl-4-trimethylsilyloxy-5-trans-octen-1-yne |

EXAMPLE 605

Preparation of 1-Iodo-4-hydroxy-4-methyl-trans-1-octene

To a stirred solution of 400 ml. of 0.5 M bis-(3-methyl-2-butyl)borane in glyme, prepared from sodium borohydride, 2-methyl-2-butene, and boronitrifluoride etherate as in Example 123, is added 63.7 (0.30 moles) of 4-methyl-4-trimethylsilyloxy-1-octyne (Example 600) at −10°. The solution is stirred at ambient temperature for 2.5 hours, cooled to −10°, and treated during 30 minutes with 158 g. (2.1 moles) of solid trimethylamine oxide with cooling. The mixture is stirred at ambient temperature for 2 hours and then poured into a stirred, ice-cold solution of 15% aqueous sodium hydroxide; the stirred mixture is treated immediately with a solution of 426 g. (1.68 moles) of iodine in 1100 ml. of tetrahydrofuran. After 4 hours the mixture is extracted with ether. The extract is washed successively with water, aqueous sodium thiosulfate, and brine and dried over magnesium sulfate. The extract is concentrated, and the residue is subjected to chromatography on silica gel with hexane to provide an oil, p.m.r. ($CDCl_3$): $\delta$ 1.18 (singlet, 4-$CH_3$ group).

EXAMPLES 606–610

The 4-trimethylsilyloxy-1-alkynes of Table 25 are converted to the 4-hydroxy-1-iodo-trans-1-octenes of the Table by the procedure described in Example 605.

TABLE 25

| Ex. | Starting 4-trimethylsilzloxy-1-octyne of Example | Product 4-hydroxy-1-iodo-trans-1-octene |
|---|---|---|
| 606 | 601 | 1-iodo-5,5-dimethyl-4-hydroxy-trans-1-nonene |
| 607 | 602 | 1-iodo-5,5-dimethyl-4-hydroxy-trans,trans-1,7-nonadiene |
| 608 | 603 | 1-iodo-5,5-dimethyl-4-hydroxy-trans-1-octene |
| 609 | 600 | 1-iodo-4-methyl-4-hydroxy-trans-1-octene |
| 610 | 604 | 1-iodo-4-methyl-4-hydroxy-trans,trans-1,5-octadiene |

EXAMPLE 611

Preparation of 1-Iodo-4-methyl-4-trimethylsilyloxy-trans-1-octene

To a stirred mixture of 24.5 g. (55.6 mmoles) of 1-iodo-4-hydroxy-4-methyl-trans-1-octene (Example 605), 13.6 g. (200 mmoles) of imidazole, and 75 ml. of dimethylformamide is added 10.9 g. (100 mmoles) of chlorotrimethylsilane. After standing overnight the mixture is poured into 250 ml. of hexane. The mixture is washed thoroughly with water followed by brine and dried over magnesium sulfate. After removal of the solvent, the product is distilled to give a colorless liquid, boiling point 67.5°–68° (0.07 mm.).

EXAMPLES 612–616

The 1-iodo-4-hydroxy-trans-1-alkenes of Table 26 are converted to the product trimethylsilyl ethers of the table according to the procedure described in Example 611.

TABLE 26

| Ex. | Starting 1-iodo-4-Hydroxy-trans-1-alkene Example | Product trimethylsilyl ether |
|---|---|---|
| 612 | 606 | 1-iodo-5,5-dimethyl-4-trimethylsilyloxy-trans-1-nonene |
| 613 | 607 | 1-iodo-5,5-dimethyl-4-trimethylsilyloxy-trans,trans-1,7-nonadiene |
| 614 | 608 | 1-iodo-5,5-dimethyl-4-trimethylsilyloxy-trans-1-octene |
| 615 | 609 | 1-iodo-4-methyl-4-trimethylsilyloxy-trans-1-octene |
| 616 | 610 | 1-iodo-4-methyl-4-trimethylsilyloxy-trans,trans-1,5-octadiene |

EXAMPLE 617

Preparation of 4-Benzoyloxy-1-octyne

To a stirred solution of 63. g. (0.50 moles) of 1-octyn-4-ol (Example 87) in 500 ml. of pyridine is added 77 g. (0.55 moles) of benzoyl chloride. After stirring for 1.5 hours the mixture is treated with 10 ml. of water, allowed to stand for 15 minutes, and concentrated. A solution of the residue in ether is washed successively with ice-cold hydrochloric acid, water, sodium bicarbonate solution, and brine. The solution is dried over magnesium sulfate, filtered through Celite, and concentrated to give an oil, max. 3240 (terminal acetylene) and 1730 cm$^{-1}$ (benzoyloxy group).

EXAMPLE 618

Stereoselective Hydrolysis of Racemic 4-benzoyloxy-1-octyne by Rhizopus arrhizus An agar slant of R. arrhizus (MUMF 1638) is used to inoculate 7 shake flasks (250 ml. Erlenmeyer). Each flask contains 50 ml. of a medium consisting of 2% Edamine, 2% glucose, and 0.72% corn steep liquor in water with pH adjusted to 7.0. A total of 14 such flasks are incubated on a rotary shaker at 28 C. After 72 hours incubation, 50 mg. of Racemic 4-benzoyloxy-1-octyne (Example 617) in 0.1 ml. of acetone is added to each flask. After 28 hours the flasks are harvested and worked up by extraction of the whole mash with an equal volume of chloroform. The combined extracts are dried over magnesium sulfate and concentrated. The resulting oil is chromatographed on a column of silica gel with hexane progressively enriched in ethyl acetate.

From fractions 3-6 is obtained 150 mg. of colorless oil, identical to 4-benzoyloxy-1-octyne, $[\alpha]_D^{25} = 5 \pm 1.0°$ (C=0.91, ethyl acetate). This compound has the (S)-configuration.

From fractions 13-20 is obtained 75 mg. of colorless oil, identical to 4-hydroxy-1-octyne, $[\alpha]_D^{25} = -17° \pm 1.0°$ (C=0.77, ethyl acetate). This compound has the (R)-configuration.

The strain of R. arrhizus utilized in this experiment is a higher fungus which grows steadily on a variety of artificial media at 20°-25° C. In this study of the taxonomic aspects of the culture, Petri dishes of potato-dextrose, malt extract, and cornmeal agars were inoculated and incubated at ambient room temperature for 10 days. Observations of cultural and morphological characteristics are recorded in the description below: Colonies on Petri dishes of Potato-dextrose agar growing rapidly, covering the agar surface in 3-5 days and producing a thick, loose mat of grayish mycelium. Colony surface characterized by abundant black sporangia. Colony reverse grayish white. Colonies on Malt extract agar growing rapidly, covering the agar surface in 3-5 days. Mycelial mat thick, grayish-yellow. Colony surface becoming brownish-black from masses of sporangia. Colony reverse yellowish. Colonies on Cornmeal Agar very thin, whitish; spreading across agar surface. Cultures transparent with relatively few sporangia produced. Visibility of micromorphology is good on this medium. Rhizoids produced sparingly along stoloniferous hyphae. Generally two to three sporangiophores arose from rhizoids. Walls of sporangiophores olive brown, 14.0-20.0 μM in width at base, tapering slightly to apex; 0.5-1.5 mm. in length. Sporangiophores terminated by spherical sporangia, 130-225 μM in diameter. Columellae hemispherical, 3-50 μM high by 50-70 μM wide. Spores brownish when mature, 6.0-8.5 μM × 4.5-6.0 μM. Spore walls conspicuously marked by longitudinal striations.

EXAMPLE 619

Preparation of (S)-4-hydroxy-1-octyne

EXAMPLE 619

Preparation of (S)-4-hydroxy-1-octyne

A solution of 1.15 g. (5.0 mmoles) of (S)-4-benzoyloxy-1-octyne (Example 618) and 1.40 g. (25 mmoles) of potassium hydroxide in 50 ml. of 10:1 methanol-water is allowed to stand at room temperature for 24 hours. The bulk of the methanol is evaporated at room temperature, and the mixture is extracted with ether. The extract is washed with brine, dried over magnesium sulfate, and evaporated to give a colorless oil, identical to 4-hydroxy-1-octyne $[\alpha]_D^{25} = +17° \pm 1.0°$ (C=0.77, ethyl acetate). This compound has the (S)-configuration.

EXAMPLES 620-625

The starting 1-alkyn-4-ols of Table 27 below are converted to the triphenylmethoxy substituted 1-alkynes by the method of Example 93.

TABLE 27

| Example | Starting 1-alkyl-4-ol of Example | Product triphenylmethoxy substituted 1-alkyne |
|---|---|---|
| 620 | 591 | 4-triphenylmethoxy-5-trans-nonen-1-yne |
| 621 | 592 | 5-methyl-4-triphenylmethoxy-1-octyne |
| 622 | 596 | 5-methyl-4-triphenylmethoxy-1-nonyne |
| 623 | 599 | 4-triphenylmethoxy-5-trans-octen-1-yne |
| 624 | 618 | (R)-4-triphenylmethoxy-1-octyne |
| 625 | 619 | (S)-4-triphenylmethoxy-1-octyne |

EXAMPLES 626-629

The product triphenylmethoxy substituted 1-iodo-1-trans-alkenes of Table 28 below are prepared from the starting triphenylmethoxy substituted 1-alkynes of the Table by the procedure described in Example 123.

TABLE 28

| Ex. | Starting triphenylmethoxy substituted 1-alkyn of Example | Product triphenylmethoxy substituted 1-iodo-trans-1-alkene |
|---|---|---|
| 626 | 620 | 1-iodo-4-triphenylmethoxy-trans,trans-1,5-nonadiene |
| 627 | 621 | 1-iodo-5-methyl-4-triphenylmethoxy-trans-1-octene |
| 628 | 622 | 1-iodo-5-methyl-4-triphenylmethoxy- |

TABLE 28-continued

| Ex. | Starting triphenylmethoxy substituted 1-alkyn of Example | Product triphenylmethoxy substituted 1-iodo-trans-1-alkene |
|---|---|---|
|  |  | trans-1-nonene |
| 629 | 623 | 1-iodo-4-triphenylmethoxy-trans,trans-1,5-octadiene |
| 630 | 624 | (R)-1-iodo-4-triphenylmethoxy-1-trans-octene |
| 631 | 625 | (S)-1-iodo-4-triphenylmethoxy-1-trans-octene |

EXAMPLE 632

Preparation of 9-oxo-11α-tetrahydropyranyloxy-16-triphenylmethoxy-17-methyl-5-cis,13-trans-prostadienoic acid A solution of 3.89 g. (7.63 mmoles) of 1-iodo-5-methyl-4-triphenylmethoxy-trans-1-nonene (Example 627) in 60 ml. of dry ether is treated with 20.4 ml. (15.26 mmoles) of 0.75 M t-butyllithium in pentane at −78° under argon and stirred for 1 hour.

In a second flask a mixture of 1.00 g. (7.63 mmoles) of cuprous pentyne, 3.2 ml. (15.26 mmoles) of hexamethylphosphorous triamide, and 30 ml. of ether is stirred until it becomes clear. This solution is added to the solution of vinyllithium reagent, and the resulting solution is stirred at −78° for 1 hour.

To the vinyl cuprate reagent is added a solution of 2.99 g. (7.63 mmoles) of 4-tetrahydropyranyloxy-2-(6-carbotetrahydropyranyloxy-2-cis-hexenyl)cyclopent-2-en-1-one (Example 37) in 30 ml. of ether so that temperature is about −78°. The resulting mixture is stirred at −78° for 40 minutes, and then the temperature is allowed to rise to −15° during 40 minutes. The mixture is poured into 250 ml. of stirred, ice-cold saturated ammonium sulfate solution, and this mixture is stirred for 30 minutes. The organic phase is separated and washed successively with water and brine. The solution is dried over magnesium sulfate and concentrated to give crude tetrahydropyran-2-yl 9-oxo-11α-tetrahydropyranyloxy-16-triphenylmethoxy-17-methyl-5-cis,13-trans-prostadienoate as an oil.

The crude product is dissolved in 40 ml. of tetrahydrofuran, 50 ml. of acetic acid, and 10 ml. of water, and the resulting mixture is stirred at room temperature for 1 hour. An additional 10 ml. of acetic acid and 5 ml. of water is added, and this mixture is stirred for an additional 30 minutes. The mixture is diluted with water and extracted with ether. The extract is washed successively with water and brine and concentrated in vacuo.

The residue is subjected to column chromatography on 150 g. of acid-washed silica gel with 15% ethyl acetate in hexane to afford an oil, i.r. (film) 1735 (ketone group), 1710 (carboxyl group), and 967 cm$^{-1}$ trans-olefin group).

EXAMPLE 633

Preparation of 9-oxo-11α,16-dihydroxy-17-methyl-5-cis,13-trans-prostadienoic acid A solution of 530 mg. (0.765 mmoles) of 9-oxo-11α-tetrahydropyranyloxy-16-triphenylmethoxy-17-methyl-5-cis,13-trans-prostadienoic acid (Example 632) in 10 ml. of tetrahydrofuran, 20 ml. of acetic acid, and 6 ml. of water is heated at 45°-50° for 4 hours. The solution is diluted with water and extracted with ethyl acetate. The extract is washed successively with water and brine, dried over magnesium sulfate, and evaporated with the aid of toluene to remove acetic acid.

The residue is subjected to column chromatography on 25 g. of acid-washed silica gel with hexane progressively enriched in ethyl acetate to afford an oil, p.m.r. (acetone-d$_6$): 4.10 (11β-hydrogen atom.

EXAMPLES 634–642

The product 9-oxo-11α-hydroxy-5-cis,13-trans-prostadienoic acids of Table 29 below are obtained by the procedure described in Examples 632 and 633. In accordance with the process described therein, the starting triphenylmethoxy or trimethylsiloxy substituted 1-iodo-trans-1-alkenes listed in Table 29 are treated with t-butyl lithium to provide the corresponding trans-1-alkenyl lithium derivative which on treatment with cuprous pentene-hexamethylphosphorus triamide furnish the corresponding lithio 1-pentynyl-(trans-1-alkenyl)cuprates, which are then treated with the 4-oxycyclopent-2-en-1-ones listed in the Table. The resulting triphenylmethoxy (or trialkylsiloxy) substituted 9-oxo-11α-tetrahydropyranyloxy-5-cis,13-trans-prostadienoic acid tetrahydropyranyl ester is hydrolyzed to the corresponding triphenylmethoxy (or hydroxy) substituted 9-oxo-11α-tetrahydropyranyloxy-5-cis,13-trans-prostadienoic acid by the procedure of Example 632.

The product compounds of the table are prepared by final hydrolysis as described in Example 633.

TABLE 29

| Example | starting 4-oxy-cyclopent-2-en-1-one of Example | Starting oxy substituted 1-iodo-1-trans-alkene of Example | Product 9-oxo-5-cis,13-trans-prostadienoic acid |
|---|---|---|---|
| 634 | 37 | 615 | 9-oxo-11α,16-dihydroxy-16-methyl-5-cis,13-trans-prostadienoic acid |
| 635 | 42 | 614 | 9-oxo-11α,16-dihydroxy-4(R),17,17-trimethyl-5-cis,13-trans-prostadienoic acid |
| 636 | 37 | 613 | 9-oxo-11α16-dihydroxy-17,17,20-trimethyl-5-cis,13-trans,19-trans-prostatrienoic acid |
| 637 | 40 | 612 | 9-oxo-11α,16-dihydroxy-17,17,20-trimethyl-4a,4b-bishomo-5-cis,-13-trans-prostadienoic acid |
| 638 | 40 | 626 | 9-oxo-11α,16-dihydroxy-20-methyl-4a,4b-bishomo-5-cis,13-trans,17-trans-prostatrienoic acid |
| 639 | 42 | 627 | 9-oxo-11α,16-dihydroxy- |

TABLE 29-continued

| Example | starting 4-oxy-cyclo-pent-2-en-1-one of Example | Starting oxy substituted 1-iodo-1-trans-alkene of Example | Product 9-oxo-5-cis,13-trans-prostadienoic acid |
| --- | --- | --- | --- |
| | | | 4(R),17-dimethyl-5-cis,-13-trans-prostadienoic acid |
| 640 | 37 | 628 | 9-oxo-11α,16-dihydroxy-17,20-dimethyl-5-cis,13-trans-prostadienoic acid |
| 641 | 37 | 629 | 9-oxo-11α,16-dihydroxy-5-cis,13-trans,17-trans-prostatrienoic acid |
| 642 | 40 | 615 | 9-oxo-11α,16-dihydroxy-16-methyl-4a,4b-bishomo-5-cis,13-trans-prostadienoic acid |
| 642a | 37 | 614 | 9-oxo-11α,16-dihydroxy-17,17-dimethyl-5-cis,13-trans-prostadienoic acid |
| 642b | 37 | 612 | 9-oxo-11α,16-dihydroxy-17,17,20-trimethyl-5-cis,-13-trans-prostadienoic acid |
| 642c | 42 | 615 | 9-oxo-11α,16-hydroxy-4(R),16-dimethyl-5-cis,-13-trans prostadienoic acid |

EXAMPLE 643

Preparation of
9-Oxo-11α,16-dihydroxy-20-methyl-5-cis,13-trans-17-trans-prostatrienoic acid To a stirred solution of 11.6 g. (22.8 mmoles) of 1-iodo-4-triphenylmethoxy-1,5-trans,trans-nonadiene (Example 626) in 160 ml. of ether at −78° is added 57 ml. of 0.8 M t-butyllithium in pentane during 20 minutes. After 2.5 hours at −78° a solution of cuprous thiophenoxide in 240 ml. of ether at −78° [prepared according to the procedure of C. J. Sih, et al., J. Amer. Chem. Soc., 97, 865 (1975), from 2.13 g. (19.3 mmoles) of thiophenol, 8.4 ml. of 2.3 M n-butyllithium in hexane, and 7.60 g. (19.3 mmoles) of tetrakis-(tri-n-butylphosphine copper (I) iodide)] is added during 1 minute. The resulting solution is stirred at −78° for 45 minutes.

To the stirred cuprate reagent is added a solution of 7.05 g. (19.0 mmoles) of 4-(trimethylsiloxy)-2-(6-carbotrimethylsiloxy-2-cis-hexenyl)cyclopent-2-en-1-one (Example 45) in 160 ml. of ether during 25 minutes. After stirring at −78° for 10 minutes the solution is stirred at −40° for 2 hours. The stirred solution is colled to −60° and treated with a solution of 2.88 g. (38 mmoles) of acetic acid in 10 ml. of ether. The resulting mixture is poured into stirred, ice-cold 2.5 M ammonium sulfate (400 ml.). The organic phase is separated and washed successively with 2.5 M ammonium sulfate and brine, dried over magnesium sulfate, and concentrated.

The resulting residue is dissolved in 190 ml. of 4:2:1 acetic acid-tetrahydrofuran-water After stirring for 1 hour at room temperature the solution is heated at 45° for 20 hours. The resulting mixture is diluted with xylene, and volatile matter is evaporated under high vacuum.

The resulting mixture is subjected to column chromatography on acid-washed silica gel with hexane progressively enriched in ethyl acetate. Fractions which contain the title compound are combined and evaporated to give an oil, i.r. (film) 3300 (hydroxy groups), 1735 (cyclopentanone), 1705 (Carboxylic acid), and 970 cm$^{-1}$ (trans-olefin groups).

EXAMPLE 644

Preparation of
9-oxo-11α,16-dihydroxy-16-methyl-5-cis,13-trans,17-trans-prostatrienoic acid To a stirred solution of 3.90 g. (11.5 mmoles) of 1-iodo-4-methyl-4-trimethylsilyloxy-trans,trans-1,5-octadiene (Example 616) in 90 ml. of ether at −78° is added 29 ml. of 0.8 M t-butyllithium in pentane during 10 minutes. After 2.5 hours at −78° a solution of cuprous thiophenoxide in 120 ml. of ether at −78° [prepared according to the procedure of C. J. Sih, et al., J. Amer. Chem. Soc., 97, 865 (1975), from 1.07 g. (9.7 mmoles) of thiophenol, 4.2 ml. of 2.3 M n-butyllithium in hexane, and 3.80 g. (9.7 mmoles) of tetrakis-(tri-n-butylphosphine copper (I) iodide)] is added during 15 minutes. The resulting solution is stirred at −78° for 45 minutes.

To the stirred cuprate reagent is added a solution of 3.54 g. (9.6 mmoles) of 4-(trimethylsiloxy)-2-(6-carbotrimethoxylsiloxy-2-cis-hexenyl)cyclopent-2-en-1-one (Example 45) in 120 ml. of ether during 25 minutes. After stirring at −78° for 10 minutes the solution is stirred at −40° for 2 hours. The stirred solution is cooled to −60° and treated with a solution of 1.15 g. (19.2 mmoles) of acetic acid in 5 ml. of ether. The resulting mixture is poured into a stirred, ice-cold solution of 2.5 M ammonium sulfate (200 ml.) containing 5 ml. of 4N hydrochloric acid. The organic phase is separated and washed successively with 2.5 M ammonium sulfate and brine, dried over magnesium sulfate, and concentrated.

The resulting residue is dissolved in 100 ml. of 4:2:1 acetic acid-tetrahydrofuran-water. After stirring for 30 minutes at room temperature the solution is diluted with 100 ml. of xylene and concentrated under high vacuum at 10°.

The resulting mixture is subjected to column chromatography on acid-washed silica gel with hexane progressively enriched in ethyl acetate. Fractions which contain the desired product are combined and evaporated to give an oil, i.r. (film) 1735 (ketone group), 1705 (carboxyl group), and 970 cm$^{-1}$ (trans-olefin groups).

EXAMPLES 645 and 646

Conjugate addition of the cuprate, obtained by treatment of the 1-iodo-1-alkene indicated in the Table 30 below with t-butyllithium followed by cuprous thiophenoxide reagent, to (R)-4-tetrahydropyranyloxy-2-(6-carbomethoxy-2-cis-hexenyl)cyclopent-2-en-1-one [C. J. Sih, et al., J. Amer. Chem. Soc., 97, 865 (1975)] according to the procedure described in Example 643 followed by removal of the protecting groups according to the method described in Example 643 is productive of the prostadienoate esters of the table.

TABLE 30

| Example | Starting 1-iodo-trans-1-alkene of Example | Product Prostadinoate ester |
|---|---|---|
| 645 | 630 | methyl 9-oxo-11(R),-16(R)-dihydroxy-5-cis,13-trans-prostadienoate |
| 646 | 631 | methyl 9-oxo-11(R),-16(S)-dihydroxy-5-cis,13-trans-prostadienoate |

EXAMPLE 647

Preparation of Methyl 9-oxo-16-hydroxy-16-methyl-5-cis,13-trans-prostadienoate

Treatment by the procedure described in Example 643 of 2-(6-carbomethoxy-2-cis-hexenyl)cyclopent-2-en-1-one (Example 82) with lithio phenylthio(4-trimethylsilyloxy-4-methyl-trans-1-octenyl)cuprate, prepared from 1-iodo-4-trimethylsilyloxy-4-methyl-trans-1-octene (Example 615) also as described in Example 643, is productive of methyl 9-oxo-16-trimethylsilyloxy-16-methyl-5-cis,13-trans-prostadienoate, which on treatment as described in Example 643 with acetic acid-tetrahydrofuran-water provides the subject prostadienoate which is purified by chromatography on silica gel to provide an oil, i.r. (film) 1735 (ester and ketone carbonyl groups) and 970 cm$^{-1}$ (trans olefin group).

EXAMPLE 648

Preparation of 9-oxo-16-hydroxy-16-methyl-5-cis,13-trans-prostadienoic acid

Saponification of methyl 9-oxo-16-hydroxy-16-methyl-5-cis,13-trans-prostadienoate (Example 647) by the procedure described in Example 205 provides the subject compound as an oil, i.r. 1735 (ketone) and 1705 cm$^{-1}$ (carboxylic acid).

EXAMPLE 649-658

The product 9-oxo-5-cis,13-trans-prostadienoic acids of Table 31 below are prepared by treatment by the procedure described in Example 647 of the cyclopentenone methyl esters listed in Table 31 with the appropriate lithio phenylthio (1-trans-alkenyl)cuprate prepared by the procedure described in Example 643 from the corresponding 1-iodo-1-trans-alkene listed in Table 31, followed by protecting group removal with acetic acid-tetrahydrofuran-water, followed by saponification by the procedure of Example 648 of the resulting hydroxy substituted methyl 9-oxo-5-cis,13-trans-prostadienoate.

TABLE 31

| Example | Starting cyclopentenone of Example | Starting 1-iodo-trans-1-alkene of Example | Product 9-oxo-5-cis,13-trans-prostadienoic acid |
|---|---|---|---|
| 649 | 82 | 626 | 9-oxo-16-hydroxy-20-methyl-5-cis,13-trans,17-trans,prostatrienoic acid |
| 650 | 81 | 615 | 9-oxo-16-hydroxy-16-methyl-4a,4b-bishomo-5-cis,13-trans-prostadienoic acid |
| 651 | 82 | 627 | 9-oxo-16-hydroxy-17-methyl-5-cis,13-trand-prostadienoic acid |
| 652 | 84 | 626 | 9-oxo-16-hydroxy-4(R),20-dimethyl-5-cis,13-trans,17-trans-prostatrienoic acid |
| 653 | 82 | 614 | 9-oxo-16-hydroxy-17,17-dimethyl-5-cis,13-trans-prostadienoic acid |
| 654 | 82 | 616 | 9-oxo-16-hydroxy-16-methyl-5-cis,13-trans,17-trans-prostatrienoic acid |
| 655 | 84 | 612 | 9-oxo-16-hydroxy-4(R),17,17,20--tetramethyl-5-cis,13-trans-prostadienoic acid |
| 656 | 81 | 628 | 9-oxo-16-hydroxy-17,20-dimethyl-4a,4b-bishomo-5-cis,13-trans-prostadienoic acid |
| 657 | 81 | 613 | 9-oxo-16-hydroxy-17,17,20-trimethyl-4a,4b-bishomo-5-cis,13-trans,19-trans-prostatrienoic acid |
| 658 | 82 | 629 | 9-oxo-16-hydroxy-5-cis,13-trans,-17-trans-prostatrienoic acid |

EXAMPLES 659-669

By the procedure of Example 296 the 9-oxo-prostadienoic acids of Table 32 below are treated with lithium perhydro-9b-boraphenalyl hydride to provide the product 9α-hydroxy-prostadienoic acids of the Table.

TABLE 32

| Ex. | Starting 9-oxo-prostadienoic acid of Example | Product 9α-hydroxyprostadienoic acid |
|---|---|---|
| 659 | 634 | 9α,11α,16-trihydroxy-16-methyl-5-cis,13-trans-prostadienoic acid |
| 660 | 635 | 9α,11α,16-trihydroxy-4(R),17,17-trimethyl-5-cis,13-trans-prostadienoic acid |
| 661 | 636 | 9α,11α,16-trihydroxy-17,17,20-trimethyl-5-cis,13-trans,19-trans-prostatrienoic acid |
| 662 | 637 | 9α,11α,16-trihydroxy-17,17,20-trimethyl-4a,4b-bishomo-5-cis,13-trans-prostadienoic acid |
| 663 | 638 | 9α,11α,16-trihydroxy-20-methyl-4a,4b-bishomo-5-cis,13-trans,17-trans-prostatrienoic acid |

TABLE 32-continued

| Ex. | Starting 9-oxo-prostadienoic acid of Example | Product 9α-hydroxyprostadienoic acid |
|---|---|---|
| 664 | 639 | 9α,11α,16-trihydroxy-4(R),17-dimethyl-5-cis,-13-trans-prostadienoic acid |
| 665 | 640 | 9α,11α,16-trihydroxy-17,20-dimethyl-5-cis,13-trans-prostadienoic acid |
| 666 | 641 | 9α,11α,16-trihydroxy-5-cis,13-trans,17-trans-prostatrienoic acid |
| 667 | 642 | 9α,11α,16-trihydroxy-16-methyl-4a,4b,bishomo-5-cis,13-trans-prostatrienoic acid |
| 668 | 643 | 9α,11α,16-trihydroxy-20-methyl-5-cis,13-trans,17-trans-prostatrienoic acid |
| 669 | 644 | 9α,11α,16-trihydroxy-16-methyl-5-cis,13-trans,-17-trans-prostatrienoic acid |

EXAMPLE 670

Preparation of
9α-hydroxy-11α-tetrahydropyranyloxy-16-triphenylmethoxy-17-methyl-5-cis,13-trans-prostadienoic acid To a stirred solution of 215 mg. (0.31 mmoles) of 9-oxo-11α-tetrahydropyranyloxy-16-triphenylmethoxy-17-methyl-5-cis,13-trans-prostadienoic acid (Example 632) in 4 ml. of tetrahydrofuran at −78° is added 2.0 ml. of 1.0 M lithium tris-(s-butyl)borohydride in 1:1 pentane-tetrahydrofuran. The resulting solution is stirred at −78° for 1 hour and then treated with water. The mixture is acidified and extracted with ethyl acetate.

The residue obtained after evaporation of the solvent is dissolved in 3 ml. of tetrahydrofuran, and the resulting solution is treated successively with 1 ml. of 2.5 N sodium hydroxide and 0.8 ml. of 30% hydrogen peroxide. After 20 minutes at 0° the solution is diluted with water, acidified with 4 N hydrochloric acid, and extracted with ethyl acetate. The extract is washed successively with water and brine, dried over magnesium sulfate, and concentrated to give an oil, i.r. (film) 3380 (9α-hydroxyl group) and 1710 cm$^{-1}$ (carboxyl group).

EXAMPLE 671

Preparation of
9α,11α,16-trihydroxy-17-methyl-5-cis,13-trans-prostadienoic acid

A stirred solution of 230 mg. (0.31 mmoles) of 9α-hydroxy-11α-tetrahydropyranyloxy-16-triphenylmethoxy-17-methyl-5-cis,13-trans-prostadienoic acid (Example 670) in 8 ml. of acetic acid, 4 ml. of tetrahydrofuran, and 4 ml. of water is heated at 45°–50° for 4 hours. The solution is diluted with water and extracted with ethyl acetate. The extract is washed successively with water and brine, dried over magnesium sulfate, and concentrated.

The residue is subjected to column chromatography on acid-washed silica gel with hexane progressively enriched in ethyl acetate to give an oil, p.m.r. (acetone-d$_6$): δ 4.17 (9β-hydrogen atom).

EXAMPLE 672

Preparation of
9β,11α,16-trihydroxy-5-cis,13-trans-prostadienoic acid

To a stirred, ice-cold solution of 350 mg. (1.0 mmole) of 9-oxo-11α,16-dihydroxy-5-cis,13-trans-prostadienoic acid (Example 149) in 40 ml. of methanol is added a partial solution of 1.1 g. (29 mmoles) of sodium borohydride in 90 ml. of cold methanol in portions during 10 minutes. After stirring at 0° for 1.5 hours, the mixture is stirred at ambient temperature for 30 minutes. The mixture is concentrated at reduced pressure, diluted with water, and acidified with hydrochloric acid. The mixture is extracted with ethyl acetate, and the extract is washed successively with water and brine, dried over magnesium sulfate, and concentrated.

The crude product is subjected to preparative layer chromatography on silica gel with the solvent system chloroform-ethanol-acetic acid (90:3.5:5.5), and the zone containing the 9β-hydroxy isomer is eluted with ethyl acetate-ethanol mixture to provide an oil, p.m.r. (acetone-d$_6$) : δ 3.98 (9α-hydrogen atom).

EXAMPLES 673–684

By the procedure of Example 672 the 9-oxo-prostadienoic acids of Table 33 below are treated with sodium borohydride to provide the product mixture of 9α- and 9β-hydroxy-prostadienoic acids which are then separated into the pure components, one of which is the 9β-hydroxy isomer. These products are indicated in the Table.

TABLE 33

| Ex. | Starting 9-oxo-prostadienoic acid of Example | Product 9β-hydroxy-prostadienoic acid |
|---|---|---|
| 673 | 634 | 9β,11α,16-trihydroxy-16-methyl-5-cis,13-trans-prostadienoic acid |
| 674 | 635 | 9β,11α,16-trihydroxy-4(R),17,17-trimethyl-5-cis,13-trans-prostadienoic acid |
| 675 | 636 | 9β,11α,16-trihydroxy-17,17,20-trimethyl-5-cis,13-trans,14-trans-prostatrienoic acid |
| 676 | 637 | 9β,11α,16-trihydroxy-17,17,20-methyl-4a,4b-bishomo-5-cis,13-trans-prostadienoic acid |
| 677 | 638 | 9β,11α,16-trihydroxy-20-methyl-4a,4b-bishomo-5-cis,13-trans,17-trans-prostatrienoic acid |
| 678 | 639 | 9β,11α,16-trihydroxy-4(R),17-dimethyl-5-cis,13-trans-prostadienoic acid |
| 679 | 640 | 9β,11α,16-trihydroxy-17,20-dimethyl-5-cis,13-trans-prostadienoic acid |
| 680 | 641 | 9β,11α,16-trihydroxy-5-cis,13-trans,17-trans-prostatrienoic acid |
| 681 | 642 | 9β,11-60 ,16-trihydroxy-16-methyl-4a-4b-bishomo-5-cis,13-trans-prostadienoic acid |
| 682 | 643 | 9β,11α,16-trihydroxy-20-methyl-5-cis,13-trans,-17-trans-prostatrienoic acid |
| 683 | 633 | 9β,11α,16-trihydroxy-17-methyl-5-cis,13-trans-prostadienoic acid |
| 684 | 644 | 9β,11α,16-trihydroxy-16-methyl-5-cis,13-trans,-17-trans-prostatrienoic acid |

EXAMPLE 685

Preparation of n-decyl
9-oxo-11α,16-dihydroxy-5-cis,13-trans-prostadienoate

A solution of 80 mg. (0.226 mmoles) of 9-oxo-11α,16-dihydroxy-5-cis,13-trans-prostadienoic acid (Example 149), 0.6 ml. of n-decyl alcohol, and 50 mg. of triethylamine in 1.5 ml. of methylene chloride is maintained at room temperature for 5 minutes. To this solution is added 50 mg. of p-toluenesulfonyl chloride. After 30 minutes an additional 10 mg. of the sulfonyl chloride is added, and after stirring for an additional 15 minutes the solution is diluted with ether and washed with water. The solution is dried over magnesium sulfate and concentrated. The residue is subjected to column chromatography on acid-washed silica gel with hexane progressively enriched in ethyl acetate to give an oil, i.r. (film) 1740 cm$^{-1}$ (ester and cyclopentanone carbonyl groups).

EXAMPLES 686-699

The prostadienoate esters of Table 34 below are prepared from the corresponding prostadienoic acids of the table and the indicated alcohol by the procedure described in Example 685.

TABLE 34

| Example | Starting Prostadienoic acid of Example | Alcohol | Product Prostadienoate Ester |
|---|---|---|---|
| 686 | 633 | methanol | Methyl 9-oxo-11α,16-dihydroxy-17-methyl-5-cis,13-trans-prostadienoate |
| 687 | 643 | ethanol | ethyl 9-oxo-11α,16-20-methyl-5-cis,13-trans,17-trans-prostatrienoate |
| 688 | 634 | n-propanol | propyl 9-oxo-11α,16-dihydroxy-16-methyl-5-cis,13-trans-prostadienoate |
| 689 | 664 | methanol | methyl 9α,11α16-trihydroxy-4(R),17-dimethyl-5-cis,13-trans,prostadienoate |
| 690 | 673 | n-butanol | butyl 9β,11α,16-trihydroxy-16-methyl-5-cis,13-trans-prostadienoate |
| 691 | 636 | n-octanol | octyl 9-oxo-11α,16-dihydroxy-17,17,20-trimethyl-5-cis,13-trans,19-trans-prostatrienoate |
| 692 | 637 | ethanol | ethyl 9-oxo-11α,16-dihydroxy-17,17,20-trimethyl-4a,4b-bishomo-5-cis,13-trans-prostadienoate |
| 693 | 635 | n-butanol | butyl 9-oxo-11α,16-dihydroxy-4(R),17,17-trimethyl-5-cis,13-trans-prostadienoate |
| 694 | 638 | methanol | methyl 9-oxo-11α,16-dihydroxy-20-methyl-4a,4b-bishomo-5-cis,13-trans,17-trans-prostatrienoate |
| 695 | 639 | ethanol | ethyl 9-oxo-11α,16-dihydroxy-4(R),17-dimethyl-5-cis,13-trans-prostadienoate |
| 696 | 644 | n-decanol | decyl 9-oxo-11α,16-dihydroxy-17,20-dimethyl-cis,13-trans,17-trans-prostatrienoate |
| 697 | 640 | n-decanol | decy; 9-oxo-11α,16-dihydroxy-17,20-dimethyl-5-cis,13-trans-prostadienoate |
| 698 | 641 | n-butanol | butyl 9-oxo-11α,16-dihydroxy-5-cis,13-trans,17-trans-prostatrienoate |
| 699 | 642 | ethanol | ethyl 9-oxo-11α,16-dihydroxy-16-methyl-4a,4b-bishomo-5-cis,13-trans-prostadienoate |

EXAMPLES 700-704

Treatment of the listed prostaglandin acids of Table 35 below with diazomethane in the usual manner (see Examples 560-586) is productive of the product methyl ester of the table. Use of other diazoalkenes would provide the appropriate alternative alkyl esters.

TABLE 35

| Example | Starting Acid of Example | Product Methyl Ester |
|---|---|---|
| 700 | 633 | methyl 9-oxo-11α,16-dihydroxy-17-methyl-5-cis,13-trans-prostadienoate |
| 701 | 634 | methyl 9-oxo-11α,16-dihydroxy-16-methyl-5-cis,13-trans-prostadienoate |
| 702 | 640 | methyl 9-oxo-11α,16-dihydroxy-17,20-dimethyl-5-cis,13-trans-prostadienoate |
| 703 | 642 | methyl 9-oxo-11α,16-dihydroxy-16-methyl-4a,4b-bishomo-5-cis,13-trans-prostadienoate |
| 704 | 644 | methyl 9-oxo-11α,16-dihydroxy-16-methyl-5-cis,13-trans,17-trans-prostadienoate |

Other compounds are 1-9-oxo-16α-hydroxy-16,20-dimethyl-5-cis, 13-trans-prostadienoic acid; dl-9-oxo-16α-hydroxy-16,20-dimethyl-5-cis,13-trans-prostadienoic; 1-9-oxo-16β-hydroxy-16,20-dimethyl-5-cis,13-trans-prostadienoic acid and dl-9-oxo-16β-hydroxy-16,20-dimethyl-5-cis,13-trans-prostadienoic acid.

Additional compounds are 1-9-oxo-11α,16β-dihydroxy-16-methyl-5-cis,13-trans,17-trans prostatrienoic acid; 1-9-oxo-11α,16α,-dihydroxy-16-methyl-5-cis,13-trans,17-trans prostatrienoic acid; dl-9-oxo-11α,16α-dihydroxy-16-methyl-5-cis,13-trans,17-trans prostatrienoic acid; and dl-9-oxo-11α,16β-dihydroxy-16-methyl-5-cis,13-trans,17-trans prostatrienoic acid.

We claim:

1. An optically active compound of the formula:

which depicts the absolute configuration of the naturally (nat.) occurring prostaglandins wherein $R_3$ is selected from the group consisting of hydroxy and $C_1$-$C_5$ alkoxy; and $R_2$ is selected from the group consisting of a moiety of the formula

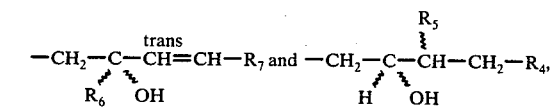

wherein $R_4$ is selected from the group consisting of $C_1$-$C_4$ alkyl and $R_5$ is selected from the group consisting of hydrogen and methyl and $R_6$ is selected from the group consisting of hydrogen and methyl and $R_7$ is selected from the group consisting of $C_2$-$C_3$ alkyl; with the proviso that when $R_5$ is methyl, then $R_4$ must be hydrogen; the racemic mixture thereof; the mirror image thereof; and the pharmacologically acceptable cationic salts thereof when $R_3$ is hydroxy.

2. A compound according to claim 1 wherein $R_3$ is as previously defined; and $R_2$ is selected from the group consisting of a moiety of the formula $$-CH_2-\underset{\underset{OH}{\diagup}\overset{R_6}{\diagdown}}{C}-\overset{trans}{CH=CH}-R_7$$

wherein $R_7$ and $R_6$ are as previously defined.

3. A compound according to claim 1, wherein $R_3$ is as previously defined; and $R_2$ is selected from the group consisting of a moiety of the formula $$-CH_2-\underset{\underset{H}{\diagup}\overset{H}{\diagdown}}{C}-\overset{R_5}{\underset{}{C}}H-CH_2-R_4$$

wherein $R_4$ and $R_5$ are as previously defined.

4. A compound according to claim 2, wherein $R_3$ is as previously defined; and $R_2$ is as previously defined, wherein $R_6$ is methyl.

5. A compound according to claim 3, wherein $R_3$ is as previously defined; and $R_2$ is as previously defined, wherein $R_5$ is methyl.

6. The compound according to claim 2, nat.-9-oxo-11α,16-dihydroxy-5-cis,13-trans,17-trans-prostatrienoic acid.

7. The compound according to claim 2, dl-9-oxo-11α,16-dihydroxy-5-cis,13-trans,17-trans-prostatrienoic acid.

8. The compound according to claim 2, nat.-9-oxo-11α,16-dihydroxy-20-methyl-5-cis,13-trans,17-trans-prostatrienoic acid.

9. The compound according to claim 2, dl-9-oxo-11α,16-dihydroxy-20-methyl-5-cis,13-trans-17-trans-prostatrienoic acid.

10. The compound according to claim 2, nat.-methyl 9-oxo-11α,16-dihydroxy-5-cis,13-trans,17-trans-prostatrienoate.

11. The compound according to claim 2, dl-methyl 9-oxo-11α,16-dihydroxy-5-cis,13-trans,17-trans-prostatrienoate.

12. The compound according to claim 3, nat.-9-oxo-11α,16-dihydroxy-5-cis,13-trans-prostadienoic acid.

13. The compound according to claim 3, dl-9-oxo-11α,16-dihydroxy-5-cis-13-trans-prostadienoic acid.

14. The compound according to claim 3, nat.-9-oxo-11α,16-dihydroxy-20-methyl-5-cis,13-trans-prostadienoic acid.

15. The compound according to claim 3, dl-9-oxo-11α,16-dihydroxy-20-methyl-5-cis,13-trans-prostadienoic acid.

16. The compound according to claim 3, nat.-9-oxo-11α,16-dihydroxy-20-ethyl-5-cis,13-trans-prostadienoic acid.

17. The compound according to claim 3, dl-9-oxo-11α,16-dihydroxy-20-ethyl-5-cis,13-trans-prostadienoic acid.

18. The compound according to claim 3, nat.-methyl 9-oxo-11α,16-dihydroxy-5-cis,13-trans-prostadienoate.

19. The compound according to claim 3, dl-methyl 9-oxo-11α,16-dihydroxy-5-cis,13-trans-prostadienoate.

20. The compound according to claim 3, nat.-pentyl 9-oxo-11α,16-dihydroxy-5-cis,13-trans-prostadienoate.

21. The compound according to claim 3, dl-pentyl 9-oxo-11α,16-dihydroxy-5-cis,13-trans-prostadienoate.

22. The compound according to claim 4, nat.-9-oxo-11α,16-dihydroxy-16-methyl-5-cis,13-trans,17-trans-prostatrienoic acid.

23. The compound according to claim 4, dl-9-oxo-11α,16-dihydroxy-16-methyl-5-cis,13-trans,17-trans-prostatrienoic acid.

24. The compound according to claim 4, nat.-methyl 9-oxo-11α,16-dihydroxy-16-methyl-5-cis,13-trans,17-trans-prostatrienoate.

25. The compound according to claim 4, dl-methyl 9-oxo-11α,16-dihydroxy-16-methyl-5-cis,13-trans-17-trans-prostatrienoate.

26. The compound according to claim 3, nat.-9-oxo-11α-hydroxy-17-methyl-19,20-dinor-5cis,13-trans-prostadienoic acid.

27. The compound according to claim 3, dl-9-oxo-11α-hydroxy-17-methyl-19,20-dinor-5cis,13-trans-prostadienoic acid.

28. An optically acitve compound of the formula:

$$\underset{OH}{R_6}\diagdown\underset{\underset{CH=CH-R_2}{trans}}{\diagup}\overset{CH_2-CH=CH-CH_2-CH_2-CH_2-\overset{O}{\overset{\|}{C}}-R_3}{}$$

which depicts the absolute configuration of the naturally (nat.) occurring prostaglandins, wherein $R_3$ is selected from the group consisting of hydroxy and $C_1-C_5$ alkoxy; $R_6$ is selected from the group consisting of a moiety of the formula:

$$\underset{}{\overset{OH}{\diagdown}\underset{}{\diagup}\overset{H}{\diagup}}C\diagdown \quad and \quad \underset{}{\overset{H}{\diagdown}\underset{}{\diagup}\overset{OH}{\diagup}}C\diagdown ;$$

wherein $R_2$ is selected from the group consisting of a moiety of the formula $$-CH_2-\underset{\underset{R_5}{\diagup}\overset{}{\diagdown}OH}{C}-\overset{trans}{CH=CH}-R_7 \text{ and } -CH_2-\underset{\underset{H}{\diagup}\overset{}{\diagdown}OH}{C}-\overset{R_5}{\underset{}{C}}H-CH_2-R_4,$$

wherein $R_4$ is selected from the group consisting of $C_1-C_4$ alkyl and $R_5$ is selected from the group consisting of hydrogen and methyl and $R_7$ is selected from the group consisting of $C_2-C_3$ alkyl; with the proviso that when $R_2$ is $$-CH_2-\underset{\underset{H}{\diagup}\overset{}{\diagdown}OH}{C}-\overset{R_5}{\underset{}{C}}H-CH_2-R_4$$

and $R_5$ is methyl, then $R_4$ must be hydrogen; the racemic mixture thereof; the mirror image thereof; and the pharmacologically acceptable cationic salts thereof when $R_3$ is hydroxy.

29. A compound according to claim 28, wherein $R_2$ and $R_3$ are as previously defined; and $R_6$ is a moiety of the formula

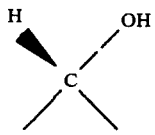

30. A compound according to claim 28, wherein $R_2$ and $R_3$ are as previously defined; and $R_6$ is a moiety of the formula

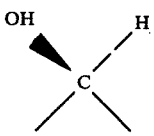

31. A compound according to claim 29, wherein $R_6$ and $R_3$ are as previously defined; and $R_2$ is selected from the group consisting of a moiety of the formula

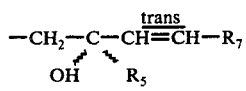

wherein $R_7$ and $R_5$ are as previously defined.

32. A compound according to claim 29, wherein $R_6$ and $R_3$ are as previously defined; and $R_2$ is selected from the group consisting of a moiety of the formula

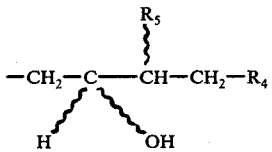

wherein $R_4$ and $R_5$ are as previously defined.

33. A compound according to claim 31, wherein $R_6$ and $R_3$ are as previously defined; and $R_2$ is as previously defined, wherein $R_5$ is methyl.

34. A compound according to claim 32, wherein $R_6$ and $R_3$ are as previously defined; and $R_2$ is as previously defined, wherein $R_5$ is methyl.

35. The compound according to claim 29, nat.-methyl 9α,11α,16-trihydroxy-20-methyl-5-cis,13-trans,17-trans-prostatrienoate.

36. The compound according to claim 29, dl-methyl 9α,11α,16-trihydroxy-20-methyl-5-cis,13-trans,17-trans-prostatrienoate.

37. The compound according to claim 30, nat.-9β,-11α,16-trihydroxy-5-cis,13-trans-prostadienoic acid.

38. The compound according to claim 30, dl-9β,-11α,16-trihydroxy-5-cis,13-trans-prostadienoic acid.

39. The compound according to claim 30, nat.-9β,-11α,16-trihydroxy-16-methyl-5-cis,13-trans-17-trans-prostatrienoic acid.

40. The compound according to claim 30, dl-9β,11α,16-trihydroxy-16-methyl-5-cis,13-trans,17-trans-prostatrienoic acid.

41. The compound according to claim 30, nat.-methyl 9α,11α,16-trihydroxy-16-methyl-5-cis,13-trans,17-trans-prostatrienoate.

42. The compound according to claim 30, dl-methyl 9α,11α,16-trihydroxy-16-methyl-5-cis,13-trans-prostatrienoate.

43. The compound according to claim 31, nat.-9α,-11α,16-trihydroxy-20-methyl-5-cis,13-trans,17-trans-prostatrienoic acid.

44. The compound according to claim 31, dl-9α,1-1α,16-trihydroxy-20-methyl-5-cis,13-trans,17-trans-prostatrienoic acid.

45. The compound according to claim 31, nat.-methyl 9α,11α,16-trihydroxy-17-methyl-5-cis,13-trans,17-trans-prostatrienoate.

46. The compound according to claim 31, dl-methyl 9α,11α,16-trihydroxy-17-methyl-5-cis,13-trans,17-trans-prostatrienoate.

47. The compound according to claim 32, nat.-9α,1-1α,16-trihydroxy-5-cis,13-trans-prostadienoic acid.

48. The compound according to claim 32, dl-9α,1-1α,16-trihydroxy-5-cis-13-trans-prostadienoic acid.

49. The compound according to claim 32, nat.-pentyl-9α,11α,16-trihydroxy-5-cis,13-trans-prostadienoate.

50. The compound according to claim 32, dl-pentyl 9α,11α,16-trihydroxy-5-cis,13-trans-prostadienoate.

51. The compound according to claim 32, nat.-methyl 9α,11α,16-trihydroxy-5-cis,13-trans-prostadienoate.

52. The compound according to claim 32, dl-methyl 9α,11α,16-trihydroxy-5-cis,13-trans-prostadienoate.

53. The compound according to claim 33, nat.-9α,1-1α,16-trihydroxy-16-methyl-5-cis,13-trans,17-trans-prostatrienoic acid.

54. The compound according to claim 33, dl-9α,1-1α,16-trihydroxy-16-methyl-5-cis,13-trans,17-trans-prostatrienoic acid.

55. The compound according to claim 32, nat.-9α,1-1α-dihydroxy-17-methyl-19,20-dinor-5-cis,13-trans-prostadienoic acid.

56. The compound according to claim 32, dl-9α,11α-dihydroxy-17-methyl-19,20-dinor-5-cis,13-trans-prostadienoic acid.

57. The optically active compound, nat.-9-oxo-11α,17-dihydroxy-5-cis,13-trans-prostadienoic acid.

58. The racemic compound, dl-9-oxo-11α,17-dihydroxy-5-cis,13-trans-prostadienoic acid.

59. A compound according to claim 4 wherein $R_3$ is hydroxy, $R_7$ is ethyl, 1-9-oxo-11α,16α-dihydroxy-16-methyl-5-cis,13-trans,17-trans prostatrienoic acid.

60. A compound according to claim 4 wherein $R_3$ is hydroxy, $R_7$ is ethyl, 1-9-oxo-11α,16β-dihydroxy-16-methyl-5-cis13-trans,17-trans prostatrienoic acid.

61. A compound according to claim 4 wherein $R_3$ is hydroxy, $R_7$ is ethyl, dl-9-oxo-11α,16α-dihydroxy-16-methyl-5-cis,13-trans prostatrienoic acid.

62. A compound according to claim 4 wherein $R_3$ is hydroxy, $R_7$ is ethyl, dl-9-oxo-11α,16β-dihydroxy-16-methyl-5-cis,13-trans prostatrienoic acid.

* * * * *